(12) United States Patent
Van Ingelgem et al.

(10) Patent No.: US 8,574,210 B2
(45) Date of Patent: Nov. 5, 2013

(54) TAMPON WITH IMPROVED ABSORPTION CAPACITY

(75) Inventors: Werner Van Ingelgem, Zele (BE); Rudolf Pollack, Grosspostwitz (DE); Steven Smet, Zele (BE)

(73) Assignee: Ontex Hygieneartikel Deutschland GmbH, Grosspostwitz (DE)

( * ) Notice: Subject to any disclaimer, the term of this patent is extended or adjusted under 35 U.S.C. 154(b) by 843 days.

(21) Appl. No.: 12/526,031

(22) PCT Filed: Feb. 5, 2008

(86) PCT No.: PCT/EP2008/051418
§ 371 (c)(1),
(2), (4) Date: Aug. 5, 2009

(87) PCT Pub. No.: WO2008/095937
PCT Pub. Date: Aug. 14, 2008

(65) Prior Publication Data
US 2010/0121251 A1 May 13, 2010

(30) Foreign Application Priority Data
Feb. 9, 2007 (EP) ..................... 07447009

(51) Int. Cl.
*A61F 13/15* (2006.01)
*A61F 13/20* (2006.01)
(52) U.S. Cl.
USPC ..................... 604/385.17; 604/904
(58) Field of Classification Search
USPC .................. 604/385.17, 385.18, 904
See application file for complete search history.

(56) References Cited

U.S. PATENT DOCUMENTS

| 435,491 | A | 9/1890 | Fredigké |
| 1,731,665 | A | 10/1929 | Huebsch |
| 1,941,717 | A | 1/1934 | Rabell |
| 1,964,911 | A | 7/1934 | Haas |
| 2,425,004 | A | 8/1947 | Rabell |
| 2,444,528 | A | 7/1948 | Popper et al. |
| 2,499,414 | A | 3/1950 | Rabell |

(Continued)

FOREIGN PATENT DOCUMENTS

| DE | 3 934 153 | 4/1991 |
| DE | 4 304 505 | 8/1994 |

(Continued)

OTHER PUBLICATIONS

European Search Report dated Jan. 20, 2011 from European patent Application No. EP 10169007.1.

(Continued)

*Primary Examiner* — Michele M Kidwell
(74) *Attorney, Agent, or Firm* — Knobbe, Martens, Olson & Bear LLP

(57) ABSTRACT

The present invention relates to a tampon (1) having an insertion end (11), a withdrawal end (14) and a tampon body in between whereby said tampon body essentially consists of liquid absorbing material and has an outer circumferential surface which is provided with longitudinal grooves (4, 4') that are separated from each other by longitudinal ribs (3, 3'), wherein at least one tampon groove (4) is defined an outer longitudinal path (2) on the surface of the tampon that diverges from the longitudinal path of the groove below the surface of the tampon. It also relates to a press, press jaw and process for its manufacture.

7 Claims, 41 Drawing Sheets

(56) References Cited

U.S. PATENT DOCUMENTS

| | | | |
|---|---|---|---|
| 2,652,056 | A | 9/1953 | Lay |
| 2,706,986 | A | 4/1955 | Carrier |
| 2,798,260 | A | 7/1957 | Niepmann et al. |
| 2,965,101 | A | 12/1960 | Schirmer et al. |
| 3,011,495 | A | 12/1961 | Brecht |
| 3,013,558 | A | 12/1961 | Leupold |
| 3,101,713 | A | 8/1963 | Sargent |
| 3,138,159 | A | 6/1964 | Schmidt |
| 3,148,680 | A | 9/1964 | Roberts et al. |
| 3,196,873 | A | 7/1965 | Beltzinger et al. |
| 3,397,695 | A | 8/1968 | Voss |
| 3,431,909 | A | 3/1969 | Krusko |
| 3,610,243 | A | 10/1971 | Jones, Sr. |
| 3,643,661 | A | 2/1972 | Crockford |
| 3,696,812 | A | 10/1972 | Jaycox |
| 3,834,389 | A | 9/1974 | Dulle |
| 3,981,305 | A | 9/1976 | Ring |
| 4,077,409 | A | 3/1978 | Murray et al. |
| 4,109,354 | A | 8/1978 | Ronc |
| 4,175,561 | A | 11/1979 | Hirschman |
| 4,276,881 | A | 7/1981 | Lilaonitkul |
| 4,291,696 | A | 9/1981 | Ring |
| 4,294,253 | A | 10/1981 | Friese |
| 4,305,391 | A | 12/1981 | Jackson |
| 4,328,804 | A | 5/1982 | Shimatani |
| 4,361,151 | A | 11/1982 | Fitzgerald |
| 4,405,323 | A | 9/1983 | Auerbach |
| 4,479,791 | A | 10/1984 | Sprague |
| 4,726,805 | A | 2/1988 | Sanders, III |
| 4,755,166 | A | 7/1988 | Olmstead |
| 4,787,895 | A | 11/1988 | Stokes et al. |
| 4,816,100 | A | 3/1989 | Friese |
| 4,891,042 | A | 1/1990 | Melvin et al. |
| 4,911,687 | A | 3/1990 | Stewart et al. |
| 4,960,417 | A | 10/1990 | Tarr et al. |
| 5,165,152 | A | 11/1992 | Kramer et al. |
| 5,346,468 | A | 9/1994 | Campion et al. |
| 5,374,258 | A | 12/1994 | Lloyd et al. |
| 5,531,674 | A | 7/1996 | Frayman |
| 5,542,914 | A | 8/1996 | Van Iten |
| 5,592,725 | A | 1/1997 | Brinker |
| 5,895,408 | A | 4/1999 | Pagan |
| 5,911,712 | A | 6/1999 | Leutwyler et al. |
| 6,177,608 | B1 | 1/2001 | Weinstrauch |
| 6,206,867 | B1 | 3/2001 | Osborn et al. |
| 6,310,269 | B1 | 10/2001 | Friese et al. |
| 6,358,235 | B1 | 3/2002 | Osborn et al. |
| 6,433,246 | B1 | 8/2002 | Nguyen et al. |
| D485,354 | S | 1/2004 | Carlin et al. |
| 6,719,743 | B1 | 4/2004 | Wada |
| 6,748,634 | B2 | 6/2004 | Nguyen et al. |
| 6,889,409 | B2 | 5/2005 | Friese et al. |
| 6,939,340 | B1 | 9/2005 | Berges |
| 6,953,456 | B2 | 10/2005 | Fuchs et al. |
| 7,070,585 | B2 | 7/2006 | Jensen |
| 7,087,045 | B2* | 8/2006 | Jensen ............ 604/385.17 |
| 7,338,483 | B2 | 3/2008 | Carlin et al. |
| 7,967,803 | B2* | 6/2011 | Van Ingelgem et al. . 604/385.17 |
| 2001/0014348 | A1 | 8/2001 | Schoelling |
| 2002/0151859 | A1 | 10/2002 | Schoelling |
| 2002/0157222 | A1 | 10/2002 | Friese et al. |
| 2003/0097108 | A1 | 5/2003 | Hasse et al. |
| 2003/0176844 | A1 | 9/2003 | Randall et al. |
| 2003/0208180 | A1 | 11/2003 | Fuchs et al. |
| 2004/0030316 | A1 | 2/2004 | Gubernick et al. |
| 2004/0199137 | A1 | 10/2004 | Lamb |
| 2005/0113783 | A1 | 5/2005 | Carlin et al. |
| 2005/0113787 | A1 | 5/2005 | Carlin |
| 2005/0113788 | A1 | 5/2005 | Carlin |
| 2005/0113789 | A1* | 5/2005 | Jensen ............ 604/385.18 |
| 2005/0113807 | A1 | 5/2005 | Carlin |
| 2005/0177090 | A1 | 8/2005 | Jensen |
| 2005/0193536 | A1 | 9/2005 | Ingelgem et al. |
| 2005/0256511 | A1 | 11/2005 | Chase et al. |
| 2005/0277904 | A1 | 12/2005 | Chase et al. |
| 2006/0111662 | A1 | 5/2006 | Karapasha et al. |
| 2006/0167429 | A1 | 7/2006 | Denti et al. |
| 2006/0167430 | A1 | 7/2006 | Denti et al. |
| 2006/0241556 | A1 | 10/2006 | Lochte et al. |
| 2007/0083182 | A1 | 4/2007 | Schoelling |
| 2008/0154176 | A1 | 6/2008 | Van Ingelgem et al. |
| 2008/0195029 | A1 | 8/2008 | Van Ingelgem et al. |
| 2008/0200892 | A1 | 8/2008 | Van Ingelgem et al. |
| 2009/0024103 | A1 | 1/2009 | Van Ingelgem et al. |
| 2012/0089111 | A1* | 4/2012 | Magnusson et al. ..... 604/385.17 |

FOREIGN PATENT DOCUMENTS

| | | | |
|---|---|---|---|
| DE | 4 325 220 | 2/1995 | |
| DE | 103 06 678 | 8/2004 | |
| DE | 20320992 | 8/2005 | |
| DE | 10 2005 050514 | 4/2007 | |
| EP | 0355 396 | 2/1990 | |
| EP | 0 422 660 | 4/1991 | |
| EP | 0 639 363 | 2/1995 | |
| EP | 1 108 408 | 6/2001 | |
| EP | 1 459 720 | 9/2004 | |
| EP | 1 481 656 | 12/2004 | |
| EP | 1498093 | 1/2005 | |
| EP | 1 547 554 A1 * | 5/2005 | ............. A61F 13/22 |
| EP | 1 547 554 | 6/2005 | |
| EP | 1 547 555 | 6/2005 | |
| EP | 1683503 | 7/2006 | |
| EP | 1 695 680 | 8/2006 | |
| EP | 1704841 | 9/2006 | |
| GB | 2120945 | 12/1983 | |
| WO | WO 00/53141 | 9/2000 | |
| WO | WO 02/49686 | 6/2002 | |
| WO | WO 02/076357 | 10/2002 | |
| WO | WO 02/078586 | 10/2002 | |
| WO | WO 2005/063162 | 7/2005 | |
| WO | WO 2007/088057 | 8/2007 | |
| WO | WO 2009/129910 | 10/2009 | |

OTHER PUBLICATIONS

Office Action dated Oct. 13, 2011 from U.S. Appl. No. 11/816,908, filed Aug. 22, 2007.

Final Office Action for U.S. Appl. No. 11/813,970 dated Mar. 17, 2011.

Final Office Action for U.S. Appl. No. 12/278,228 dated Mar. 22, 2011.

International Search Report for International application No. PCT/EP2009/067047, dated Feb. 17, 2010 by European Patent Office.

International Search Report for International application No. PCT/EP2009/065089, dated Jun. 9, 2010 by European Patent Office.

International Search Report for International application No. PCT/EP2009/063998, dated Mar. 11, 2010 by European Patent Office.

International Search Report for PCT/EP2008/051418 dated Jul. 31, 2008.

Search Report dated Jun. 4, 2004 from European Patent Application No. 03447303.

Search Report dated Apr. 11, 2006 from International Patent Application No. PCT/EP2006/000407.

Partial Search Report dated Aug. 17, 2005 from European Patent Application No. 05447004.

Search Report dated Nov. 10, 2005 from European Patent Application No. 05447065.

Search Report dated Apr. 28, 2006 from International Patent Application No. PCT/EP2006/001598.

Partial Search Report dated Nov. 14, 2005 from European Patent Application No. 05447042.

Search Report dated Jun. 29, 2007 from International Patent Application No. PCT/EP2007/000872.

Search Report dated Jun. 5, 2008 from International Patent Application No. PCT/EP2008/051418.

Office Action dated Jan. 23, 2007 from U.S. Appl. No. 11/021,671, filed Dec. 22, 2004.

(56) References Cited

OTHER PUBLICATIONS

Office Action dated Jul. 11, 2007 from U.S. Appl. No. 11/021,671, filed Dec. 22, 2004.
Office Action dated Mar. 6, 2008 from U.S. Appl. No. 11/021,671, filed Dec. 22, 2004.
Office Action dated Nov. 28, 2008 from U.S. Appl. No. 11/021,671, filed Dec. 22, 2004.
Office Action dated Jun. 24, 2009 from U.S. Appl. No. 11/021,671, filed Dec. 22, 2004.
Office Action dated Mar. 18, 2010 from U.S. Appl. No. 11/021,671, filed Dec. 22, 2004.
Office Action dated Sep. 21, 2010 from U.S. Appl. No. 11/813,970, filed Feb. 8, 2008.
Office Action dated Sep. 21, 2009 from U.S. Appl. No. 11/909,250, filed Sep. 20, 2007.
Office Action dated Apr. 16, 2010 from U.S. Appl. No. 11/909,250, filed Sep. 20, 2007.
Office Action dated Sep. 30, 2009 from U.S. Appl. No. 11/816,908, filed Aug. 22, 2007.
Office Action dated May 13, 2010 from U.S. Appl. No. 11/816,908, filed Aug. 22, 2007.
Office Action dated Sep. 22, 2010 from U.S. Appl. No. 12/278,228, filed Aug. 4, 2008.

* cited by examiner

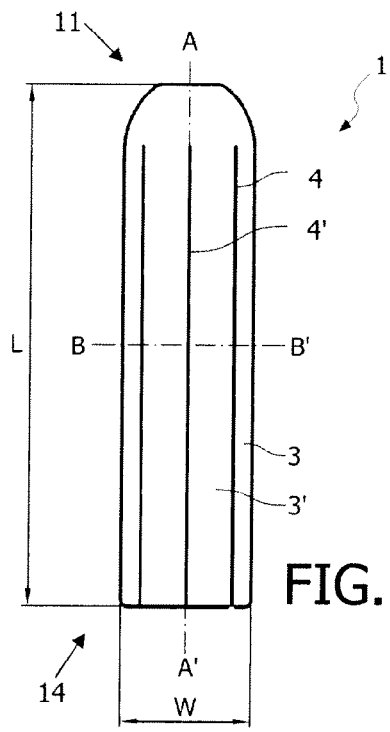
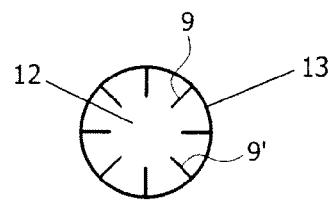
FIG. 1A  FIG. 1B
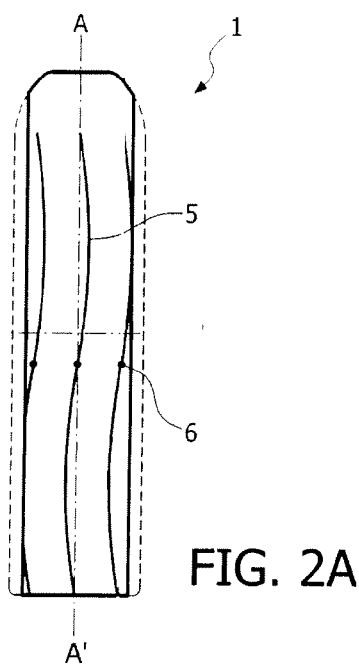
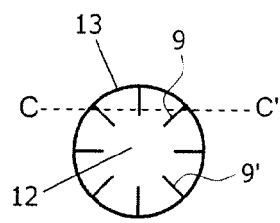
FIG. 2A  FIG. 2B

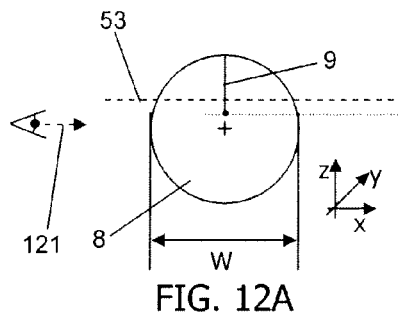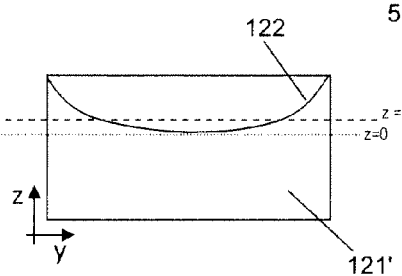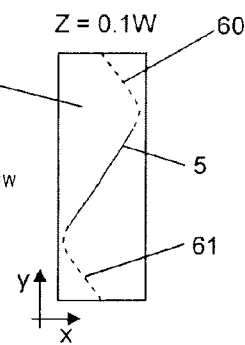
FIG. 12A  FIG. 12B  FIG. 12C
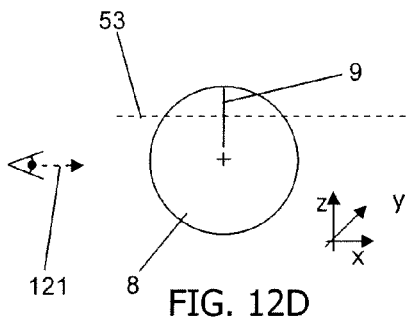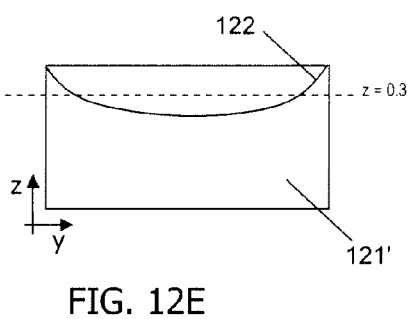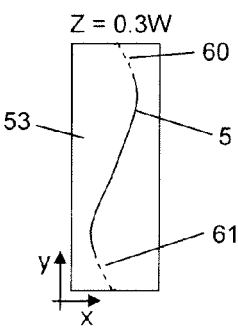
FIG. 12D  FIG. 12E  FIG. 12F
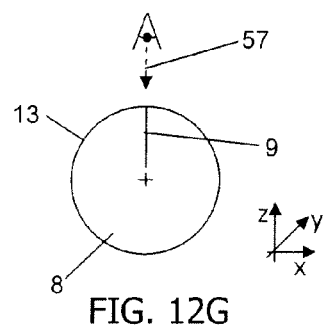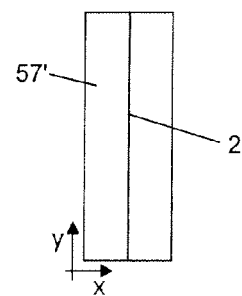
FIG. 12G  FIG. 12H

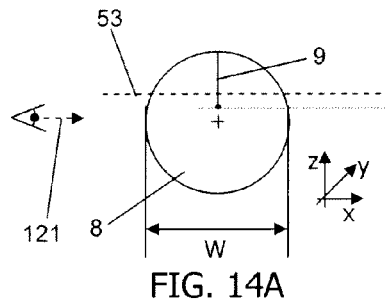 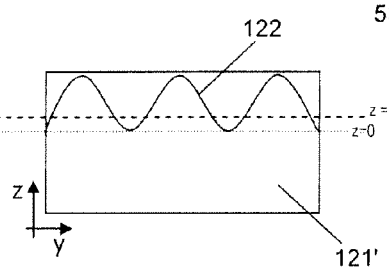 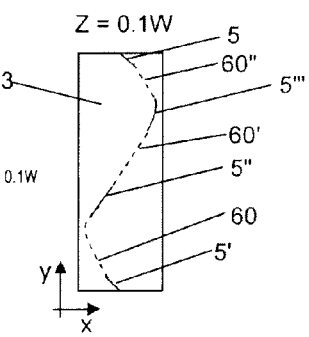
FIG. 14A    FIG. 14B    FIG. 14C
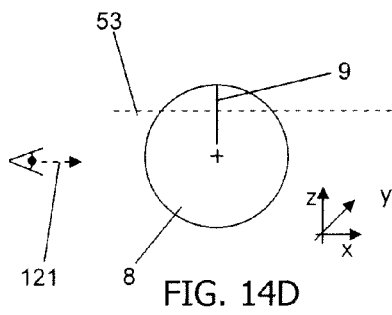 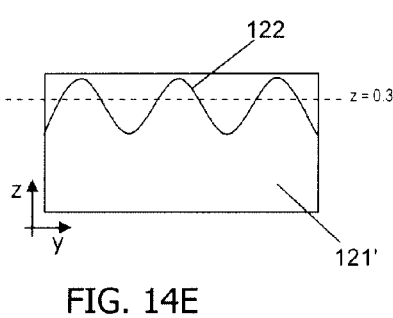 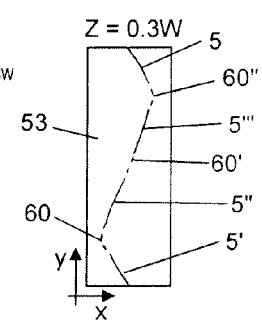
FIG. 14D    FIG. 14E    FIG. 14F
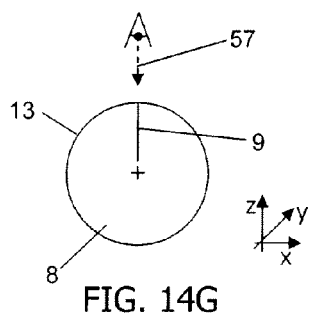 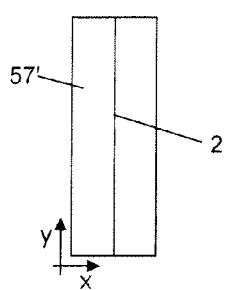
FIG. 14G    FIG. 14H

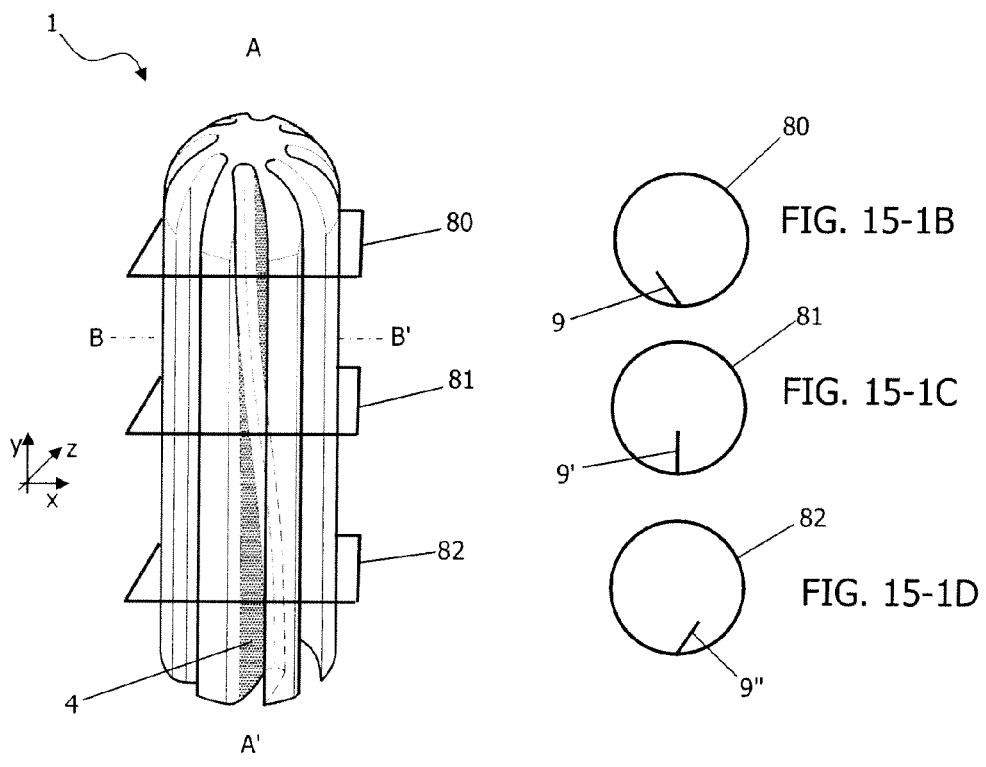
FIG. 15-1A
FIG. 15-1B
FIG. 15-1C
FIG. 15-1D
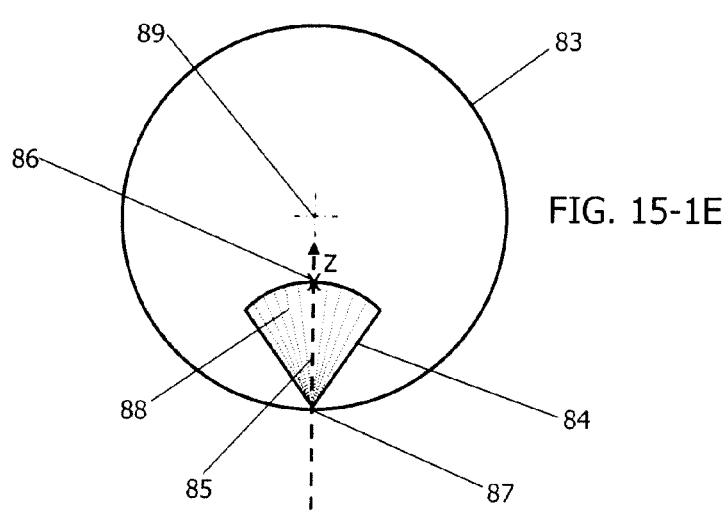
FIG. 15-1E

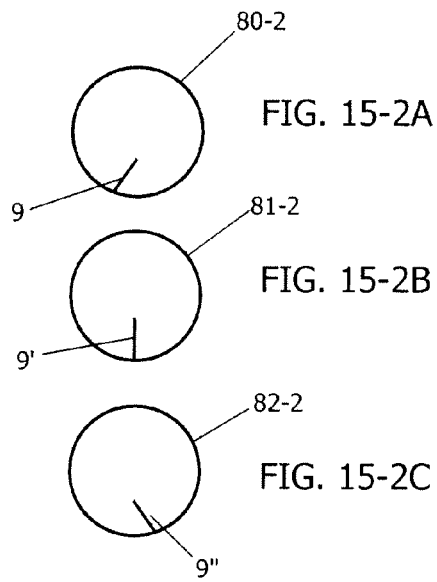
FIG. 15-2A
FIG. 15-2B
FIG. 15-2C
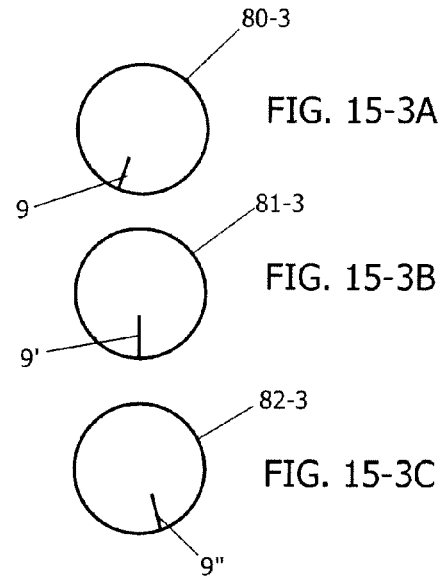
FIG. 15-3A
FIG. 15-3B
FIG. 15-3C
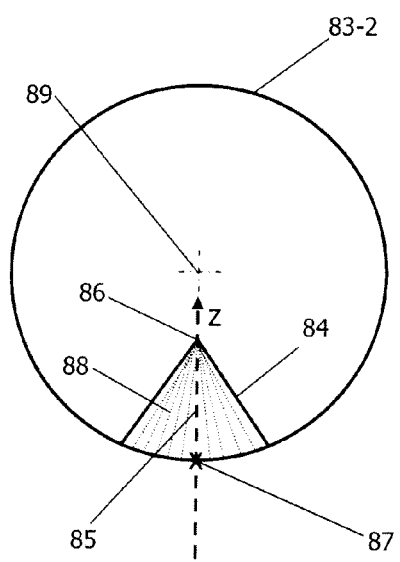
FIG. 15-2D
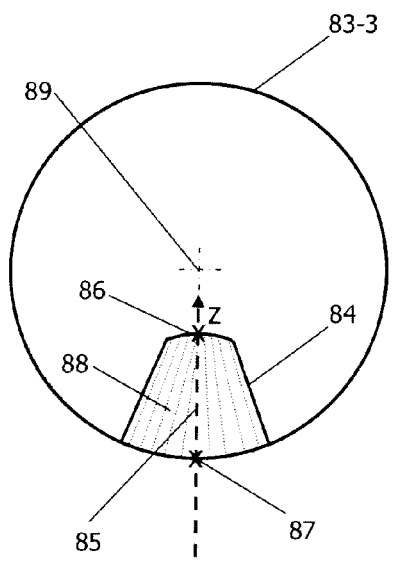
FIG. 15-3D

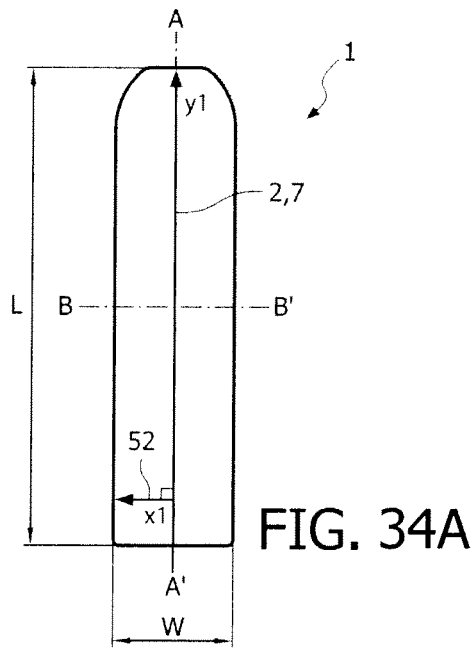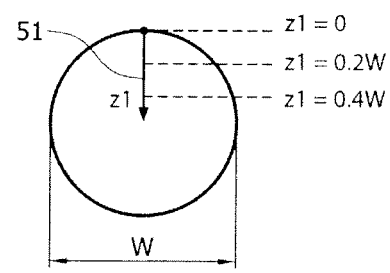
FIG. 34A          FIG. 34B
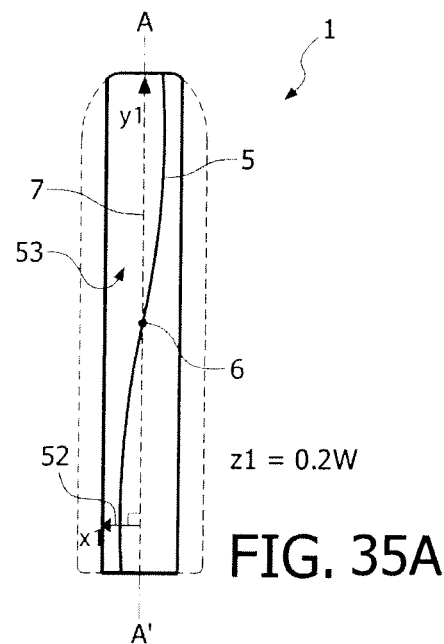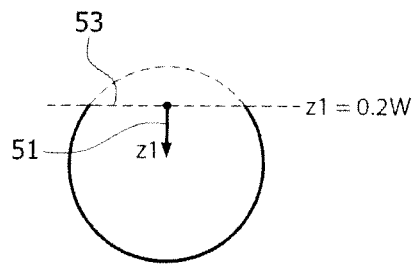
FIG. 35A          FIG. 35B

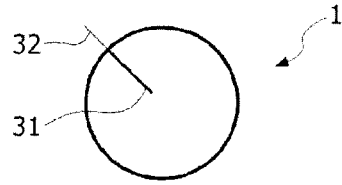
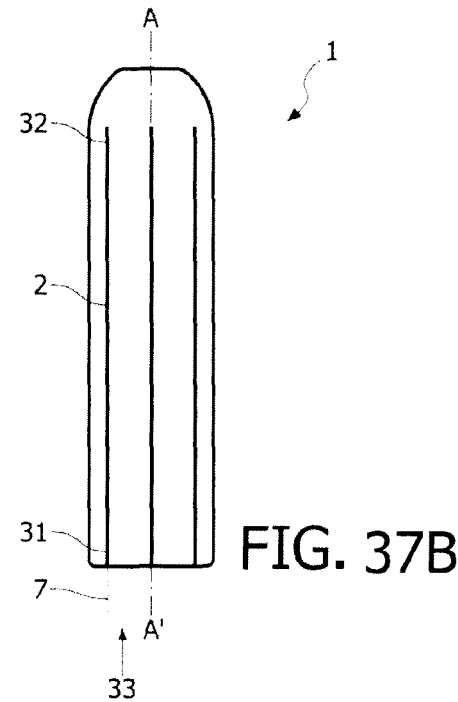
FIG. 37A        FIG. 37B
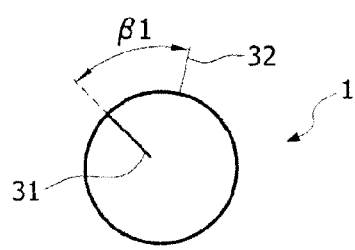
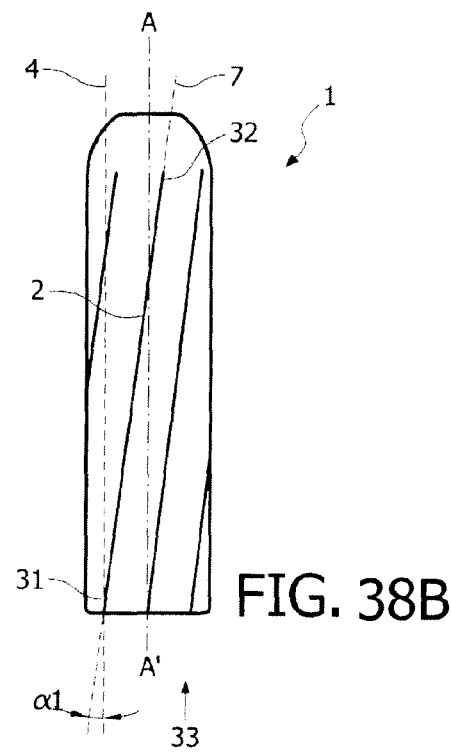
FIG. 38A        FIG. 38B

TAMPON WITH IMPROVED ABSORPTION CAPACITY

CROSS-REFERENCE TO RELATED APPLICATIONS

This application is the U.S. National Phase under 35 U.S.C. §371 of International Application PCT/EP2008/051418, filed Feb. 5, 2008, which claims priority to EP 07447009.7, filed Feb. 9, 2007.

FIELD OF THE INVENTION

The present invention relates to a tampon suitable for feminine hygiene and/or medical purposes.

BACKGROUND TO THE INVENTION

Intravaginal tampons are in common use by women for the retention of fluids or menses discharged along the walls of the vagina during the menstrual cycle. The menstrual discharge, comprising endometrial cells, secretions and blood, is intermittent and takes place over hours and days. The blood and other matter exude following the line of gravity. Sometimes the flow is light, sometimes heavy. Intravaginal tampons are usually formed of absorbent materials such as cotton, rayon cellulose wading, synthetic sponge, cellulose fluff, synthetic fibres or combinations of these materials and compressed or moulded usually to a generally cylindrical configuration of a size to fit within the vaginal tract.

Tampons having an insertion end, a withdrawal end, a withdrawal cord and a central section extending therebetween are well known in the art. From the prior art, cylindrical shaped tampons are known having ribs defined by grooves, said ribs extending outwards. Such tampons are known for example from WO 02/078586, EP 0 422 660, US 2002/0157222, U.S. Pat. No. 5,592,725, U.S. Pat. No. 5,895,408, EP 1 108 408, US 2003/0208180, WO 00/53141 and EP 0 639 363. For instance, WO 02/078586 and WO 02/076357 disclose tampons having inclined shaped grooves. The outer surface of the tampons provided with inclined shaped, pressed longitudinal grooves describing a straight path in the longitudinal direction of said tampon. EP 1 459 720 describes a vaginal tampon having sinusoidal grooves along the outer surface, separated by longitudinal ribs.

However, a disadvantage of tampons known in the art is that its absorption of fluid is generally insufficient and relatively slow, such that by-pass and leakage problems may occur after the tampon has been put into use.

In view hereof, there is a need in the art for a tampon, which overcomes one or more of these problems of the prior art. There is a need in the art for a tampon having improved absorption capacity compared to tampons known in the prior art.

The present invention aims to provide a tampon having improved absorption capacity compared to typical inclined-grooved or straight groove tampons known in the prior art. It is further an aim of the invention to provide a tampon that is soft to the touch and therefore comfortable to insert into the body cavity.

The advantages of the present tampons will become clear to the persons skilled in the art from the description and the accompanying figures provided below.

SUMMARY OF THE INVENTION

Reference is made in the description below to the drawings which exemplify particular embodiments of the invention; they are not at all intended to be limiting. The skilled person may adapt the products and method and substitute components and features according to the common practices of the person skilled in the art.

With reference to FIG. 1, the present invention relates to a tampon 1 in particular for feminine hygiene having a longitudinal body showing in compressed condition a length L in the axial direction of the tampon body and a width W in the transversal direction of the tampon body, whereby said tampon essentially consists of compressed absorbent fibrous material and has an outer circumferential surface 13 which is at least partially provided with longitudinal grooves that are separated from each other by longitudinal ribs 3, 3'.

The present tampon is in particular characterized in that at least one tampon groove 4 is defined an outer longitudinal path 2 on the surface of the tampon that diverges from the longitudinal path of the groove below the surface of the tampon. When the outer longitudinal path 2 is at least partly divergent from the longitudinal path of the groove below the surface of the tampon, it at least partly deviates therefrom. The divergence can be any form, for example, in appearance, shape, inclination, amplitude, form, size, frequency, scale. For example, the groove below the surface may be inclined to the outer longitudinal path 2. Alternatively, the groove below the surface may adopt a wave-shaped (curved) pattern, a saw tooth pattern etc, having one, two or more points of inflection or crossing, compared to a different path of the surface of the tampon. Alternatively, the groove below the surface may adopt an undulating pattern, a saw tooth pattern etc, having a greater amplitude compared with a similar pattern on the surface of the tampon. Generally any divergence which increases the length of the groove below the surface compared with the outer longitudinal path 5 is envisaged. Alternatively, any divergence which increases the length of the outer longitudinal path 5 compared with the inner longitudinal path 2 is envisaged.

More in particular, the present tampon is characterized in that the at least one tampon groove 4 is defined by a plurality of inner longitudinal paths 5, each tracing the longitudinal path of a groove at a given depth, and an outer longitudinal path 2 on the surface of the tampon, and whereby the outer longitudinal path 2 at least partially diverges from at least one inner longitudinal path 5.

The present tampon is in additionally or independently characterized in that at least one tampon groove 4 is defined by a plurality of inner longitudinal paths 5 below the surface of the tampon (FIGS. 2A, 2B), whereby at least two inner longitudinal paths 5 are different or divergent. This compares with the prior art where the longitudinal path of each groove below the surface of the tampon is unchanging, from the core to the surface. The plurality of inner longitudinal paths thus may change (in shape or path or otherwise) in the direction from the core 12 to the surface 13 of the tampon. The change may be gradual or abrupt. The groove of a tampon of the present invention may be defined by a plurality of inner longitudinal paths 5 below the surface of the tampon, the path of each inner longitudinal path 5 being across an x-y plane at a depth z, whereby at the inner longitudinal paths of at least two x-y planes are divergent. The path of the groove between successive x-y planes in the z-direction may change in a plurality of ways. For example, the shape (from sinusoidal to sawtooth), the amplitude of undulations (e.g. from gentle to pronounced wave), and/or inclination (e.g. from aligned with the central axis to inclined with the central axis). Although it is mentioned that at least two inner longitudinal paths 5 are divergent, it may in practice be the case that the majority of inner longitudinal paths are divergent from each other e.g.

55%, 60%, 70%, 80%, 90% or more consecutive inner longitudinal paths are divergent. Preferably the divergent paths gives rise to a path length in an x-y plane that decreases as the x-y plane rises towards the surface of the tampon i.e. as z increases. Alternative and equally preferably, the divergent paths give rise to a path length in an x-y plane that increases as the x-y plane rises towards the surface of the tampon i.e. as z increases.

When the outer longitudinal path 2 is at least partly divergent from the inner longitudinal path 5, it at least partly deviates therefrom. The divergence can be any form, for example, in appearance, shape, inclination, amplitude, form, size, frequency, scale. For example, the inner longitudinal path 5 may be inclined to the outer longitudinal path 2. Alternatively, the inner longitudinal path 5 may adopt a wave-shaped (curved) pattern, a saw tooth pattern etc, having one, two or more points of inflection or crossing, compared to a different path of the surface of the tampon. Alternatively, the inner longitudinal path 5 may adopt an undulating pattern, a saw tooth pattern etc, having a greater amplitude compared with a similar pattern on the surface of the tampon. Generally any divergence which increases the length of the inner longitudinal path 2 compared with the outer longitudinal path 5 is envisaged. Alternatively, any divergence which increases the length of the outer longitudinal path 5 compared with the inner longitudinal path 2 is envisaged.

Similarly, when an inner longitudinal path 5 of a groove is at least partly divergent from another inner longitudinal path 5 of the same groove, it at least partly deviates therefrom. The divergence can be any form, for example, in appearance, shape, inclination, amplitude, form, size, frequency, scale. For example, one inner longitudinal path 5 may be inclined to another inner longitudinal path 5. Alternatively, one inner longitudinal path 5 may adopt a wave-shaped (curved) pattern, a saw tooth pattern etc, having one, two or more points of inflection or crossing, compared to another inner longitudinal path 5. Alternatively, the inner longitudinal path 5 may adopt an undulating patter, a saw tooth pattern etc, having a greater amplitude compared with a similar pattern of another inner longitudinal path 5 in the same groove. Generally any divergence which increases the length of the one inner longitudinal path 5 compared with another inner longitudinal path 5 is envisaged. Alternatively, any divergence which decreases the length of one inner longitudinal path 5 compared with another inner longitudinal path 5 is envisaged.

The present tampon is a new configuration, a departure from the tampons known in the art that provides a non-uniform groove profile from the innermost point of the groove to the surface of the tampon. The present configuration gives a tampon several important advantages. Longer grooves of the present tampons substantially improve the tampons' absorptive capacity by making available more surface area for absorption, while maintaining a more comfortable insertion and wearing. The internal groove configuration of the present tampon thus gives substantially more expansion and absorption capacity to the tampon, compared to tampons having uniform groove paths. This is the case even for inclined-shaped groove tampons, without any negative manufacturing effects. The effect can be modulated (i.e. increased or reduced) according to the extent by which the inner longitudinal path changes in the direction from the core to the surface of the tampon. The tampon advantageously requires less tampon material to achieve the same absorption. Therefore, they are easier and cheaper to manufacture. In addition, grooves following the herein defined curved path permit a purposeful enlargement of the effective product surface. The grooves following the herein defined paths enlarge the surface of the tampon and provide longer distances for the body fluid to traverse before leakage around the tampon occurs. This improvement can results from any depth of groove. However, it is preferred that the groove has a depth of at least about 1 mm, and preferably of more than about 3 mm, preferably about 3 mm to about 6 mm.

The invention may further summarized by the following embodiments.

One embodiment of the invention is a tampon (1) having an insertion end (11), a withdrawal end (14) and a tampon body in between whereby said tampon body essentially consists of liquid absorbing material and has an outer circumferential surface which is provided with longitudinal grooves (4, 4') that are separated from each other by longitudinal ribs (3, 3'), wherein at least one tampon groove (4) is defined an outer longitudinal path (2) on the surface of the tampon that diverges from the longitudinal path of the groove below the surface of the tampon.

Another embodiment of the invention is a tampon (1) as described above, wherein the tampon groove (4) is defined by a plurality of inner longitudinal paths (5) below the surface of the tampon, each tracing the longitudinal path of a groove at a given depth, and an outer longitudinal path (2) on the surface of the tampon, and whereby the outer longitudinal path (2) at least partially diverges from at least one inner longitudinal path (5).

Yet another embodiment of the invention is a tampon (1) as described above, wherein at least two inner longitudinal paths (5) diverge from each other.

Yet another embodiment of the invention is a tampon (1) as described above, wherein the majority of inner longitudinal paths diverge from each other.

Yet another embodiment of the invention is a tampon (1) as described above, wherein the lengths of said majority of inner longitudinal paths (5) of a groove decrease or decrease gradually, in the direction from the core (12) to the surface of the tampon.

Yet another embodiment of the invention is a tampon (1) as described above, wherein at least one of the inner longitudinal paths (5) of a groove is undulated.

Yet another embodiment of the invention is a tampon (1) as described above, wherein at least two of said inner longitudinal paths (5) are undulated, and the amplitudes of said undulations decrease in the direction from the core (12) to the surface of the tampon.

Yet another embodiment of the invention is a tampon (1) as described above, wherein at least two of said inner longitudinal paths (5) are undulated, and the amplitudes of said undulations increase in the direction from the core (12) to the surface of the tampon.

Yet another embodiment of the invention is a tampon (1) as described above, wherein the frequency of said undulations decease in the direction from the core (12) to the surface of the tampon.

Yet another embodiment of the invention is a tampon (1) as described above, wherein the frequency of said undulations increase in the direction from the core (12) to the surface of the tampon.

Yet another embodiment of the invention is a tampon (1) as described above, wherein the at least two inner longitudinal paths (5) are inclined.

Yet another embodiment of the invention is a tampon (1) as described above, wherein said inclination gradually decreases as the inner longitudinal paths (5) aligns with a longitudinal axis (A-A') of the tampon in the direction from the core (12) to the surface of the tampon.

Yet another embodiment of the invention is a tampon (1) as described above, wherein said inclination gradually increases as the inner longitudinal paths (5) diverges from a longitudinal axis (A-A') of the tampon in the direction from the core (12) to the surface of the tampon.

Yet another embodiment of the invention is a tampon (1) as described above, wherein said majority of inner longitudinal paths (5) are straight lines.

Yet another embodiment of the invention is a tampon (1) as described above, wherein the inner longitudinal path (5) is defined as the longitudinal path of a groove across an x-y plane (53) of a tampon perpendicular to the z-axis, wherein y-axis is parallel to the longitudinal axis (A-A') of the tampon, the z-axis lies along a radius of the tampon and the x-axis is perpendicular to the y and z axes, and the plurality of inner longitudinal paths (5) shows the function:

$$x=((y \cdot a)/z)+b$$

wherein a is different from zero and is constant, b is an offset which can be constant or can change in proportion to the value of z,
wherein y corresponds to a value along the y-axis,
wherein x corresponds to a value along the x-axis
wherein z corresponds to a value along the z-axis, and z has a smaller value towards the core (12) of the tampon compared with the surface (13).

Yet another embodiment of the invention is a tampon (1) as described above, wherein at least one of the inner longitudinal paths (5) is curved having one or more points of inflection (6) which inflection point defines a convex part and a concave part.

Yet another embodiment of the invention is a tampon (1) as described above, wherein the majority of inner longitudinal paths (5) are curved and divergent.

Yet another embodiment of the invention is a tampon (1) as described above, wherein the longitudinal path (5) is defined as the path of a groove across an x-y plane (53) of a tampon perpendicular to the z-axis, wherein y-axis is parallel to the longitudinal axis (A-A') of the tampon, the z-axis lies along a radius of the tampon and the x-axis is perpendicular to the y and z axes, and the plurality of inner longitudinal paths (5) shows the function:

$$x=((a \cdot y-m)/z)+b$$

wherein m is an odd positive whole number which is different from 1,
wherein a is a constant, different from zero, b is an offset which can be constant or can change in proportion to the value of z,
wherein y corresponds to a value along the y-axis,
wherein x corresponds to a value along the x-axis,
wherein z corresponds to a value along the z-axis.

Yet another embodiment of the invention is a tampon (1) as described above, wherein the longitudinal path (5) is defined as the path of a groove across an x-y plane (53) of a tampon perpendicular to the z-axis, wherein y-axis is parallel to the longitudinal axis (A-A') of the tampon, the z-axis lies along a radius of the tampon and the x-axis is perpendicular to the y and z axes, and the plurality of inner longitudinal paths (5), shows the function:

$$x=a \cdot y^{-3}/z+b.$$

wherein a is a constant, different from zero, b is an offset which can be constant or can change in proportion to the value of z,
wherein y corresponds to a value along the y-axis,
wherein x corresponds to a value along the x-axis,
wherein z corresponds to a value along the z-axis.

Yet another embodiment of the invention is a tampon (1) as described above, wherein the value of x is comprised between $-\frac{1}{2}$ W and $+\frac{1}{2}$ W.

Yet another embodiment of the invention is a tampon (1) as described above, wherein the value of y is comprised between $-\frac{1}{2}$ L and $+\frac{1}{2}$ L.

Yet another embodiment of the invention is a tampon (1) as described above, wherein the value of z is comprised between 0.01 W and 0.45 W.

Yet another embodiment of the invention is a tampon (1) as described above, wherein the outer longitudinal path (2) is parallel to the longitudinal axis (A-A') of the tampon, so giving rise to tampons with a straight groove appearance.

Yet another embodiment of the invention is a tampon (1) as described above, wherein the outer longitudinal path (2) is inclined to the longitudinal axis (A-A') of the tampon, so giving rise to tampons with an inclined groove appearance.

Yet another embodiment of the invention is a tampon (1) as described above, wherein the angle of inclination is between 10 to 50 deg or −10 to −50 deg.

Yet another embodiment of the invention is a tampon (1) as described above, the at least two inner longitudinal paths (5) are displaced from each other.

Yet another embodiment of the invention is a tampon (1) as described above, wherein the majority of the inner longitudinal paths (5) is displaced, where the displacement increases gradually in the direction from the core (12) to the surface of the tampon.

Yet another embodiment of the invention is a tampon (1) as described above, where in inner longitudinal path (5) is defined as the path of a groove across an x-y plane (53) of a tampon perpendicular to the z-axis, wherein y-axis is parallel to the longitudinal axis (A-A') of the tampon, the z-axis lies along a radius of the tampon and the x-axis is perpendicular to the y and z axes, wherein the majority of inner longitudinal paths (5), and the majority of inner longitudinal paths (5) is gradually displaced along the x-axis as z changes.

Yet another embodiment of the invention is a tampon (1) as described above, wherein the inner longitudinal paths (5) towards the core of a tampon, are incomplete.

Yet another embodiment of the invention is a tampon (1) as described above, wherein said inner longitudinal paths (5) become incomplete gradually at the proximal and/or distal ends, giving rise to a barrel-shaped tampon upon expansion.

Yet another embodiment of the invention is a tampon (1) as described above, wherein the at least two inner longitudinal paths (5) diverge from each other in appearance, shape, inclination, and/or amplitude.

Yet another embodiment of the invention is a tampon (1) as described above, in which the tampon is provided with a finger recess and said finger recess optionally at the withdrawal end.

Yet another embodiment of the invention is a tampon (1) as described above, wherein said finger recess is at the withdrawal end.

Yet another embodiment of the invention is a tampon (1) as described above, wherein the tampon is provided with a dome shaped insertion end.

Yet another embodiment of the invention is a tampon (1) as described above, in which the tampon is provided with a mushroom shaped insertion end.

Yet another embodiment of the invention is a tampon (1) as described above, in which the tampon is provided with a rivet shaped insertion end.

Yet another embodiment of the invention is a tampon (1) as described above, wherein the tampon is provided with a constricted withdrawal end.

Yet another embodiment of the invention is a tampon (1) as described above, in which the tampon is provided with a conical shaped withdrawal end.

Yet another embodiment of the invention is a tampon (1) as described above, having a withdrawal cord which extends from said withdrawal end.

Yet another embodiment of the invention is a tampon (1) as described above, in which the ribs touch each other so as to form an essentially smooth cylindrical surface.

Yet another embodiment of the invention is a tampon (1) as described above, provided with one or more markings on the surface.

Yet another embodiment of the invention is a tampon (1) as described above, wherein said marking one or more of alpha numerals, graphic illustrations, patterns, solid colours and photographic illustrations.

Yet another embodiment of the invention is a tampon (1) as described above, wherein said marking is information.

Yet another embodiment of the invention is a tampon (1) as described above, provided with one or more chemical, biochemical or biological indicators that are capable of changing colour.

Yet another embodiment of the invention is a tampon (1) as described above, wherein a chemical, biochemical or biological indicator is capable of colour change according to the presence of a disease or condition detectable by a colour change reaction.

Yet another embodiment of the invention is a tampon (1) as described above, wherein a condition is anaemia and a chemical indicator detects iron or haemoglobin.

Yet another embodiment of the invention is a tampon (1) as described above, wherein a condition is diabetes and a chemical indicator detects glucose.

Yet another embodiment of the invention is a tampon (1) as described above, wherein a condition is a sexually transmitted disease and a chemical indicator detects antigens towards said sexually transmitted disease.

Yet another embodiment of the invention is a tampon (1) as described above, wherein the tampon has a fibre core of highly compressed fibrous material and an outer circumferential surface which is provided with longitudinal ribs that extend radially outwards and that are defined by said longitudinal grooves.

Yet another embodiment of the invention is a tampon (1) as described above, wherein said longitudinal ribs are at least partially relatively uncompressed compared with the fibre core.

Yet another embodiment of the invention is a tampon (1) as described above, provided within an applicator.

In another aspect, the invention also provides a press for manufacturing the tampon of the invention, comprising press jaws 30 arranged around a press axis 69, each jaw including a penetrating segment 63 for penetrating the absorbing material, one or more pressing shoulders 64 and a pressing head 65, characterised in that at least one penetrating segment 63 is defined by a plurality of longitudinal paths (PS longitudinal paths) 70, where each path runs in the direction of the press axis 69, whereby at least two PS longitudinal paths at least partly diverge from each other.

The press and jaws are further summarized in the following embodiments.

One embodiment of the invention is a press suitable for the manufacture of a tampon as defined above.

Another embodiment of the invention is a press as described above, comprising press jaws (30) arranged around a press axis (69), each jaw including a penetrating segment (63) for penetrating the absorbing material, one or more pressing shoulders (64) and a pressing head (65), characterised in that at least one penetrating segment (63) is defined by a plurality of longitudinal paths (PS longitudinal paths) (70), where each path runs in the direction of the press axis (69), whereby at least two PS longitudinal paths at least partly diverge from each other.

Yet another embodiment of the invention is a press as described above, where a PS longitudinal path at the base of the penetrating segment, known as the PS outer longitudinal path, is at least partly divergent from a PS longitudinal path towards the extremity (67) of the penetrating segment.

Yet another embodiment of the invention is a press as described above, wherein the lengths of the majority of PS longitudinal paths (70) decrease in the direction from the extremity (67) of the penetrating segment (63) to the pressing head (65).

Yet another embodiment of the invention is a press as described above, wherein the lengths of said majority of PS longitudinal paths (70) increase in the direction from the extremity (67) of the penetrating segment (63) to the pressing head (65).

Yet another embodiment of the invention is a press as described above, wherein the at least two PS longitudinal paths (70) are undulated.

Yet another embodiment of the invention is a press as described above, wherein the majority of PS longitudinal paths (70) are undulated and divergent, and the amplitudes of said undulations decrease gradually in the direction from the extremity (67) of the penetrating segment (63) to the pressing head (65).

Yet another embodiment of the invention is a press as described above, wherein the majority of PS longitudinal paths (70) are undulated and divergent, and the amplitudes of said undulations increase gradually in the direction from the extremity (67) of the penetrating segment (63) to the pressing head (65).

Yet another embodiment of the invention is a press as described above, wherein said majority of PS longitudinal paths (70) are undulated and divergent, and the frequency of said undulations decease gradually in the direction from the extremity (67) of the penetrating segment (63) to the pressing head (65).

Yet another embodiment of the invention is a press as described above, wherein said majority of PS longitudinal paths (70) are undulated and divergent, and the frequency of said undulations increase gradually in the direction from the extremity (67) of the penetrating segment (63) to the pressing head (65).

Yet another embodiment of the invention is a press as described above, wherein the at least two PS longitudinal paths (70) are curved having one or more points of inflection (6) which inflection point defines a convex part and a concave part.

Yet another embodiment of the invention is a press as described above, wherein the majority of PS longitudinal paths (70) are divergent and curved having one or more points of inflection (6) which inflection point defines a convex part and a concave part.

Yet another embodiment of the invention is a press as described above, wherein the PS longitudinal path (70) is defined as longitudinal midpath across an x-y plane (71) of a penetrating segment (63) which plane is perpendicular to the z-axis of the press jaw (60), wherein the y-axis is parallel to the longitudinal axis (68) of the pressing shoulder (64), the x-axis is perpendicular thereto, and the z-axis is along the direction of movement of the press jaw (60) and is perpendicular to both the x- and y-axes, and the plurality of PS longitudinal paths (70) shows the function:

$$x=((a \cdot y^{-m})/z)+b$$

wherein m is an odd positive whole number which is different from 1,
wherein a is a constant, different from zero,
b is an offset which is constant or changes in proportion to the value of z,
wherein y corresponds to a value along the y-axis,
wherein x corresponds to a value along the x-axis
wherein z corresponds to a value along the z-axis.

Yet another embodiment of the invention is a press as described above, wherein the PS longitudinal path (70) is defined as longitudinal midpath across an x-y plane (71) of a penetrating segment (63) which plane is perpendicular to the z-axis of the press jaw (60), wherein the y-axis is parallel to the longitudinal axis (68) of the pressing shoulder (64), the x-axis is perpendicular thereto, and the z-axis is along the direction of movement of the press jaw (60) and is perpendicular to both the x- and y-axes, and the plurality of PS longitudinal paths (70) shows the function:

$$x=a \cdot y^{-3}/z+b$$

wherein a is a constant, different from zero,
b is an offset which is constant or changes in proportion to the value of z,
wherein y corresponds to a value along the y-axis,
wherein x corresponds to a value along the x-axis
wherein z corresponds to a value along the z-axis.

Yet another embodiment of the invention is a press as described above, wherein the at least two PS longitudinal paths (70) are inclined.

Yet another embodiment of the invention is a press as described above, wherein the majority of the PS longitudinal paths (70) are divergent and inclined, and inclination decreases gradually as the PS longitudinal paths (70) align with the press axis (69) in the direction from the pressing head (65) to the extremity (67) of a penetrating segment (63).

Yet another embodiment of the invention is a press as described above, wherein the majority of the PS longitudinal paths (70) are divergent and inclined, and said inclination increases gradually as the PS longitudinal paths (70) diverges from the press axis (69) in the direction from the pressing head (65) to the extremity (67) of a penetrating segment (63).

Yet another embodiment of the invention is a press as described above, wherein the at least two PS longitudinal paths (70) are straight lines.

Yet another embodiment of the invention is a press as described above, wherein the majority of the PS longitudinal paths (70) are divergent and inclined, and said inclination decreases gradually as the PS longitudinal paths (70) align with press axis (69) in the direction from the pressing head (65) to the extremity (67) of a penetrating segment (63).

Yet another embodiment of the invention is a press as described above, wherein the majority of the PS longitudinal paths (70) are divergent and inclined, wherein said inclination increases gradually as the PS longitudinal paths (70) align with press axis (69) in the direction from the pressing head (65) to the extremity (67) of a penetrating segment (63).

Yet another embodiment of the invention is a press as described above, wherein angle of inclination is 10 to 50 deg or −10 to −50 deg.

Yet another embodiment of the invention is a press as described above, wherein the PS longitudinal path (70) is defined as longitudinal midpath across an x-y plane (71) of a penetrating segment (63) which plane is perpendicular to the z-axis of the press jaw (60), wherein the y-axis is parallel to the longitudinal axis (68) of the pressing shoulder (64), the x-axis is perpendicular thereto, and the z-axis is along the direction of movement of the press jaw (60) and is perpendicular to both the x- and y-axes, and the plurality of PS longitudinal paths (70) shows the function:

$$x=((y \cdot a)/z)+b$$

wherein a is different from zero and is constant, b is an offset which can be constant or can change in proportion to the value of z,
wherein y corresponds to a value along the y-axis,
wherein x corresponds to a value along the x-axis,
wherein z corresponds to a value along the z-axis.

Yet another embodiment of the invention is a press as described above, wherein the PS longitudinal path (70) at the base (66) of the penetrating segment, known as the PS outer longitudinal path, describes a straight line that is parallel to press axis (69), giving rise to pressed tampons with a non-inclined groove appearance.

Yet another embodiment of the invention is a press as described above, wherein the PS longitudinal path (70) at the base (66) of the penetrating segment known as the PS outer longitudinal path, describes a straight line that is inclined to press axis (69), giving rise to pressed tampons with an inclined groove appearance.

Yet another embodiment of the invention is a press as described above, wherein the majority of PS inner longitudinal paths (70) is gradually displaced in the direction from the pressing head (65) to the extremity (67) of a penetrating segment (63).

Yet another embodiment of the invention is a press as described above, wherein the PS longitudinal path (70) is defined as longitudinal midpath across an x-y plane (71) of a penetrating segment (63) which plane is perpendicular to the z-axis of the press jaw (60), wherein the y-axis is parallel to the longitudinal axis (68) of the pressing shoulder (64), the x-axis is perpendicular thereto, and the z-axis is along the direction of movement of the press jaw (60) and is perpendicular to both the x- and y-axes, and the majority of PS longitudinal paths (70) is gradually displaced along the x-axis as z changes.

Yet another embodiment of the invention is a press as described above, wherein impression depth of a penetrating segment (63) along the press axis (69) is variable.

Yet another embodiment of the invention is a press as described above, wherein said variation provides a profile with a dome shape one end, in a longitudinal cross-section of a press when the press jaws are closed, so producing a tampon domed at the insertion end.

Yet another embodiment of the invention is a press as described above, wherein said variation provides a mushroom-shaped profile in a longitudinal cross-section of a press when the press jaws are closed.

Yet another embodiment of the invention is a press as described above, wherein said variation provides a rivet-shaped profile in a longitudinal cross-section of a press when the press jaws are closed.

Yet another embodiment of the invention is a press as described above, wherein said variation provides a conical shape profile, in a longitudinal cross-section of a press when the press jaws are closed, so producing a tampon with a conical shape at the withdrawal end.

Yet another embodiment of the invention is a press as described above, wherein the wherein the PS longitudinal path (70) is incomplete towards the extremity (67) of the penetrating segment (63).

Yet another embodiment of the invention is a press as described above, wherein the wherein the PS longitudinal path (70) is incomplete at the longitudinal ends of the press jaw.

Yet another embodiment of the invention is a press as described above, wherein the PS longitudinal path (70) is defined as longitudinal midpath across an x-y plane (71) of a penetrating segment (63) which plane is perpendicular to the z-axis of the press jaw (60), wherein the y-axis is parallel to the longitudinal axis (68) of the pressing shoulder (64), the x-axis is perpendicular thereto, and the z-axis is along the direction of movement of the press jaw (60) and is perpendicular to both the x- and y-axes, and the PS longitudinal path (70) becomes incomplete as the value of z decreases.

Yet another embodiment of the invention is a press jaw suitable for the manufacture of a tampon as defined above.

Yet another embodiment of the invention is a press jaw as defined above, comprising a penetrating segment (63) for penetrating the absorbing material, one or more pressing shoulders (64) and a pressing head (65), characterised in that said penetrating segment (63) is defined by a plurality of longitudinal paths (PS longitudinal paths) (70), whereby at least two PS longitudinal paths are divergent from each other.

Yet another embodiment of the invention is a press jaw as defined above, whereby the majority of PS longitudinal paths are divergent, and diverge gradually in the direction from the extremity (67) of the penetrating segment (63) to the pressing head (65).

Yet another embodiment of the invention is a press jaw as defined above, further defined by the features of the press defined above.

Another embodiment of the invention relates to a process for producing a tampon of the invention, comprising the steps of:
 providing a tampon blank of fibrous material having a longitudinal axis;
 compressing in a press the tampon blank and forming longitudinal grooves at an outer circumferential surface of the tampon whereby at least one tampon groove is defined by a plurality of inner longitudinal paths 5 below the surface of the tampon whereby the inner longitudinal paths 5 change in the direction from the core 12 of the surface of the tampon.
 withdrawing said pressed tampon out of the press in a longitudinal direction of the tampon body.

Another embodiment of the invention relates to a process for manufacturing a tampon, comprising the use of one or more press jaws as described above.

Another embodiment of the invention relates to a process for manufacturing a tampon, comprising the use of as described above.

Another embodiment of the invention relates to a use of a press as above.

Another embodiment of the invention relates to a process for producing a tampon as described above, comprising the steps of:
 providing a tampon blank of fibrous material having a longitudinal axis;
 compressing in a press the tampon blank and forming longitudinal grooves at an outer circumferential surface of the tampon whereby at least one tampon groove is defined by a plurality of inner longitudinal paths (5) below the surface of the tampon whereby the inner longitudinal paths (5) change in the direction from the core (12) of the surface of the tampon.
 withdrawing said pressed tampon out of the press in a longitudinal direction of the tampon body.

Another embodiment of the invention is process as described above wherein the divergence of the inner longitudinal path (5) decreases gradually from the core (12) of the tampon towards surface (13) of the tampon.

Another embodiment of the invention is process as described above, wherein said inner longitudinal path (5) is as defined above.

Those skilled in the art will immediately recognise the many advantages of the present invention from the detailed description and accompanying figures provided below.

FIGURE LEGENDS

FIGS. 3A to 5F show a system for defining the path of the groove along a plane defined by the x- and y-axis, at a depth along the z-axis. In FIGS. 3-1A to 3-1F and FIGS. 3-2A to 3-2F, the inner longitudinal path is undulating; in FIGS. 4-1A to 4-1F and FIGS. 4-2A to 4-2F, the inner longitudinal path is inclined; in FIGS. 5-1A to 5-1F and FIGS. 5-2A to 5-2F, the inner longitudinal path is curved with a point of inflection.

Figures 1A, 3:
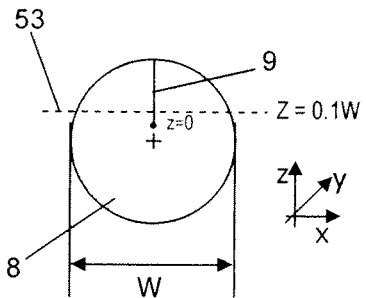
FIG. 1A shows an illustration of a tampon 1 of the invention, disposed with straight longitudinal grooves which flank longitudinal ribs.
Figures 1B, 3:
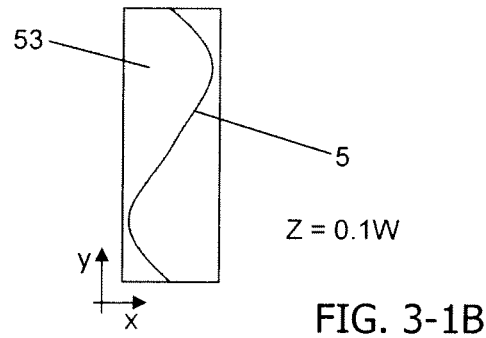
FIG. 1B shows a view of the tampon end on, across a transverse section along line B-B'.

FIGS. 3-1A and 3-1B depict an inner longitudinal path below the surface of the tampon, when, arbitrarily, z=0.1 W; at a deeper groove depth, the amplitude of curvature of the inner longitudinal path is increased compared with when z=0.3 W.

Figures 1C, 3:
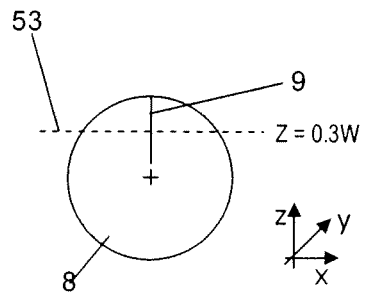
Figures 1D, 3:
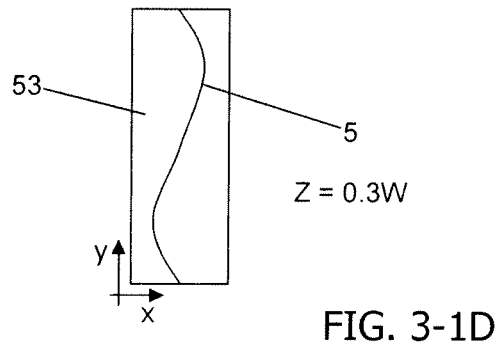

FIGS. 3-1C and 3-1D depict an inner longitudinal path below the surface of the tampon, when, arbitrarily, z=0.3 W, and the amplitude of curvature of the inner longitudinal path is reduced compared with when z=0.1 W.

Figures 1E, 3:
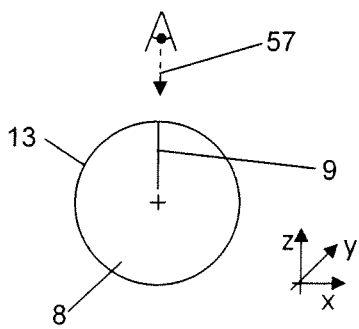
Figures 1F, 3:
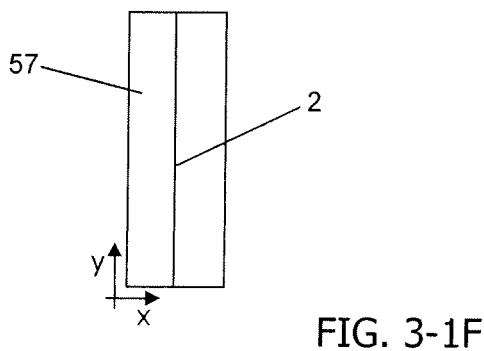

FIGS. 3-1E and 3-1F depict the path of the groove on the surface of the tampon which has no amplitude compared with the path of the groove below the surface.

Figures 2A, 3:
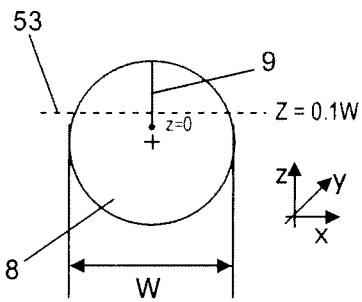
FIG. 2A shows a longitudinal cross-section of the tampon of FIG. 1A across line C-C' showing below the surface of the tampon closed longitudinal grooves describing a curved path, which path is known as the inner longitudinal path 5.
Figures 2B, 3:
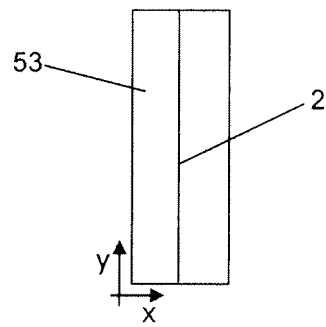
Fig. 2B shows a tampon end on illustrating line C-C' which section is shown in FIG. 2A.

FIGS. 3-2A and 3-2B depict an inner longitudinal path below the surface of the tampon, when, arbitrarily, z=0.1 W; at a deeper groove depth, the amplitude of curvature of the inner longitudinal path is decreased (zero) compared with when z=0.3 W.

Figures 2C, 3:
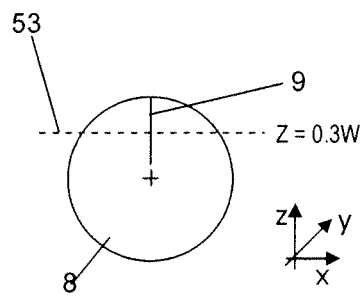
Figures 2D, 3:
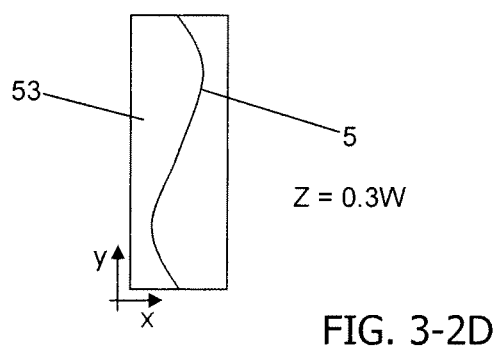

FIGS. 3-2C and 3-2D depict an inner longitudinal path below the surface of the tampon, when, arbitrarily, z=0.3 W, and the amplitude of curvature of the inner longitudinal path is increased compared with when z=0.1 W.

Figures 2E, 3:
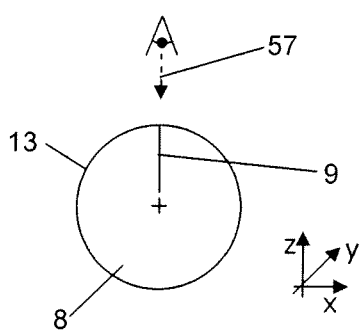
Figures 2F, 3:
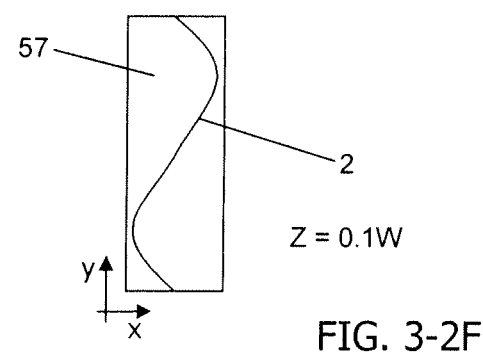

FIGS. 3-2E and 3-2F depict the path of the groove on the surface of the tampon which has an increased amplitude compared with the path of the groove below the surface.

Figures 1A, 4:
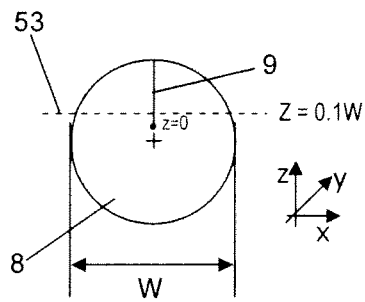
Figures 1B, 4:
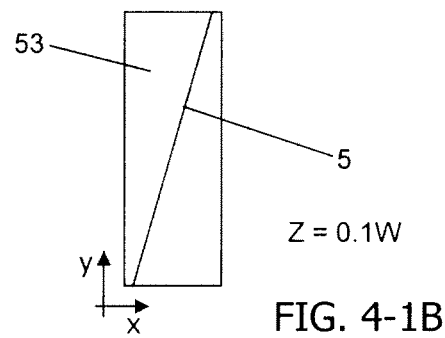
Figures 1C, 4:
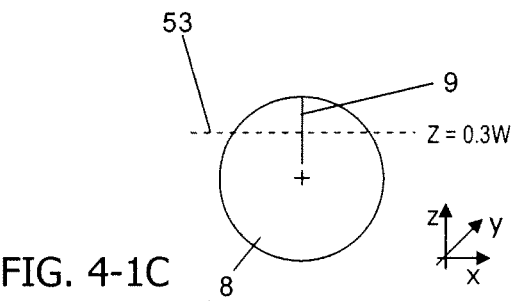
Figures 1D, 4:
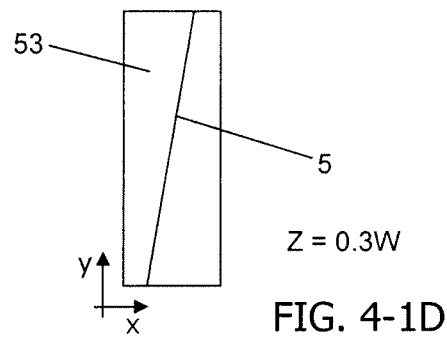
Figures 1E, 4:
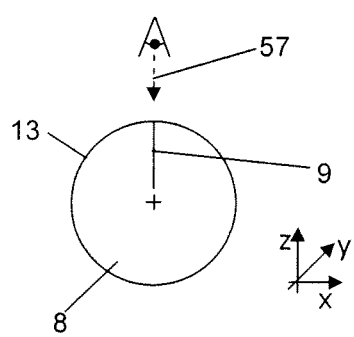
Figures 1F, 4:
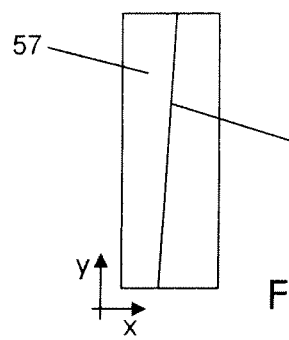
Figures 2A, 4:
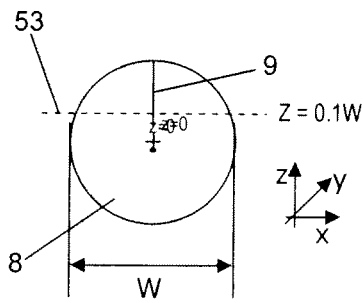
Figures 2B, 4:
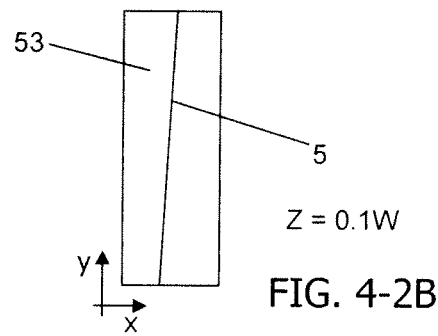
Figures 2C, 4:
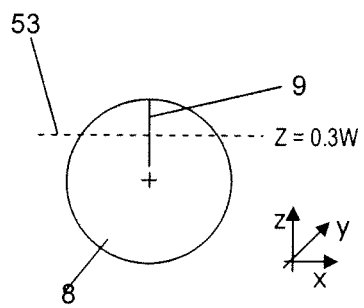
Figures 2D, 4:
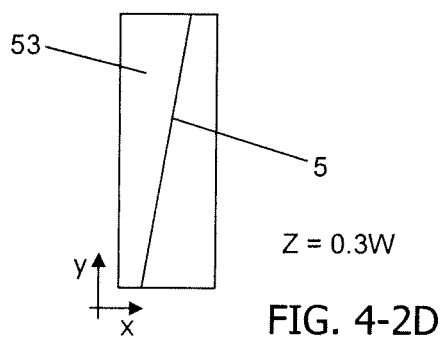
Figures 2E, 4:
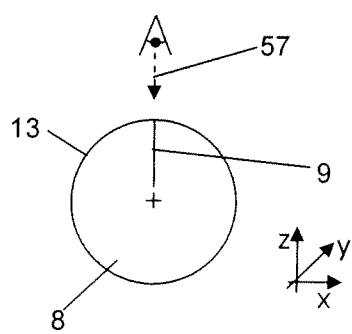
Figures 2F, 4:
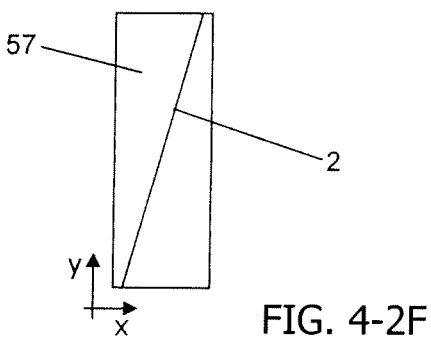

FIGS. 4-1A and 4-1B depict an inner longitudinal path below the surface of the tampon, when, arbitrarily, z=0.1 W; at a deeper groove depth, the incline of the inner longitudinal path is increased compared with when z=0.3 W.

FIGS. 4-1C and 4-1D depict an inner longitudinal path below the surface of the tampon, when, arbitrarily, z=0.3 W, and the incline of the inner longitudinal path is reduced compared with when z=0.1 W.

FIGS. 4-1E and 4-1F depict the path of the closed groove in the surface of the tampon which has less inclination compared with the path of the groove below the surface.

FIGS. 4-2A and 4-2B depict an inner longitudinal path below the surface of the tampon, when, arbitrarily, z=0.1 W; at a deeper groove depth, the incline of the inner longitudinal path is reduced compared with when z=0.3 W.

FIGS. 4-2C and 4-2D depict an inner longitudinal path below the surface of the tampon, when, arbitrarily, z=0.3 W, and the incline of the inner longitudinal path is increased compared with when z=0.1 W.

FIGS. 4-2E and 4-2F depict the path of the closed groove in the surface of the tampon which has less the most inclination compared with the path of the groove below the surface.

Figures 1A, 5:
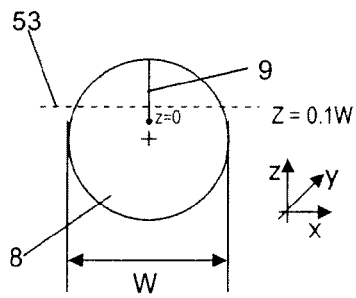
Figures 1B, 5:
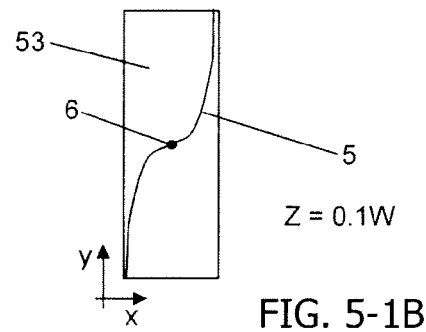
Figures 1C, 5:
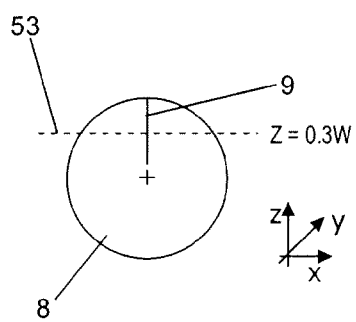
Figures 1D, 5:
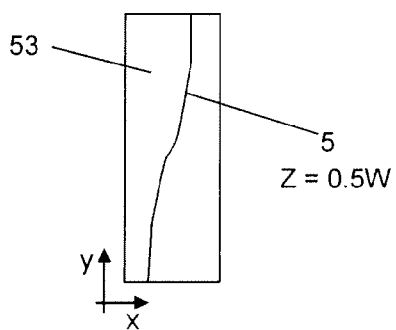
Figures 1E, 5:
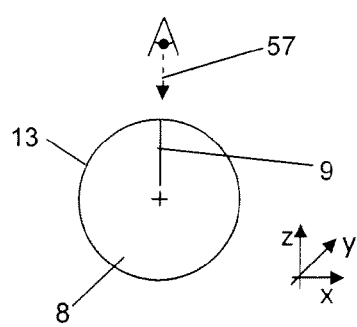
Figures 1F, 5:
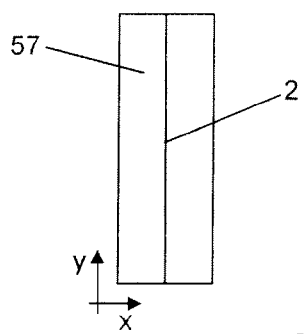
Figures 2A, 5:
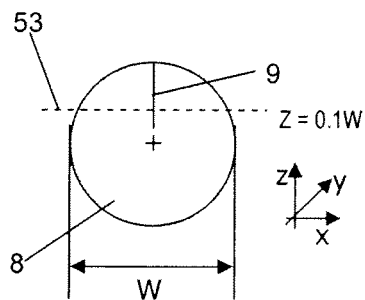
Figures 2B, 5:
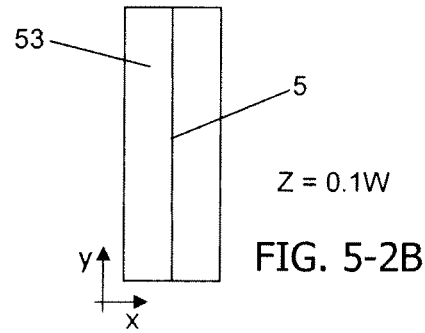
Figures 2C, 5:
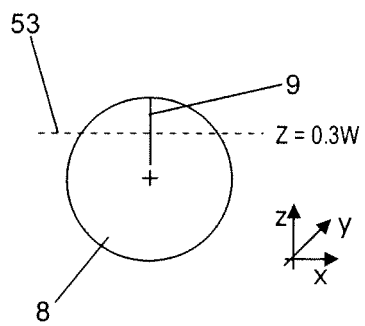
Figures 2D, 5:
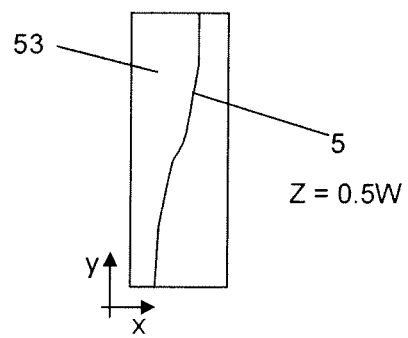
Figures 2E, 5:
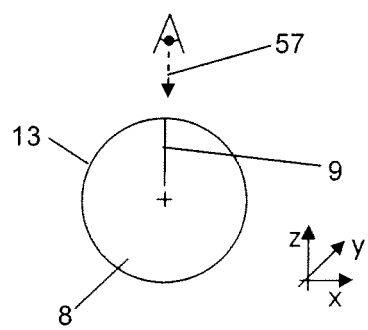
Figures 2F, 5:
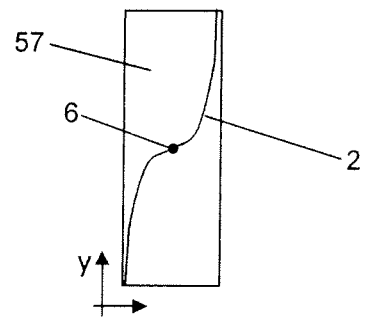

FIGS. 5-1A and 5-1B depict an inner longitudinal path below the surface of the tampon, when, arbitrarily, z=0.1 W; at a deeper groove depth, the curvature of the inner longitudinal path is increased compared with when z=0.3 W.

FIGS. 5-1C and 5-1D depict an inner longitudinal path below the surface of the tampon, when, arbitrarily, z=0.3 W, and the curvature of the inner longitudinal path is reduced compared with when z=0.1 W.

FIGS. 5-1E and 5-1F depict the path of the closed groove in the surface of the tampon.

FIGS. 5-2A and 5-2B depict an inner longitudinal path below the surface of the tampon, when, arbitrarily, z=0.1 W; at a deeper groove depth, the curvature of the inner longitudinal path is decreased (zero) compared with when z=0.3 W.

FIGS. 5-2C and 5-2D depict an inner longitudinal path below the surface of the tampon, when, arbitrarily, z=0.3 W, and the curvature of the inner longitudinal path is increased compared with when z=0.1 W.

FIGS. 5-2E and 5-2F depict the path of the closed groove in the surface of the tampon which has less the most curvature compared with the path of the groove below the surface.

Figure 6:
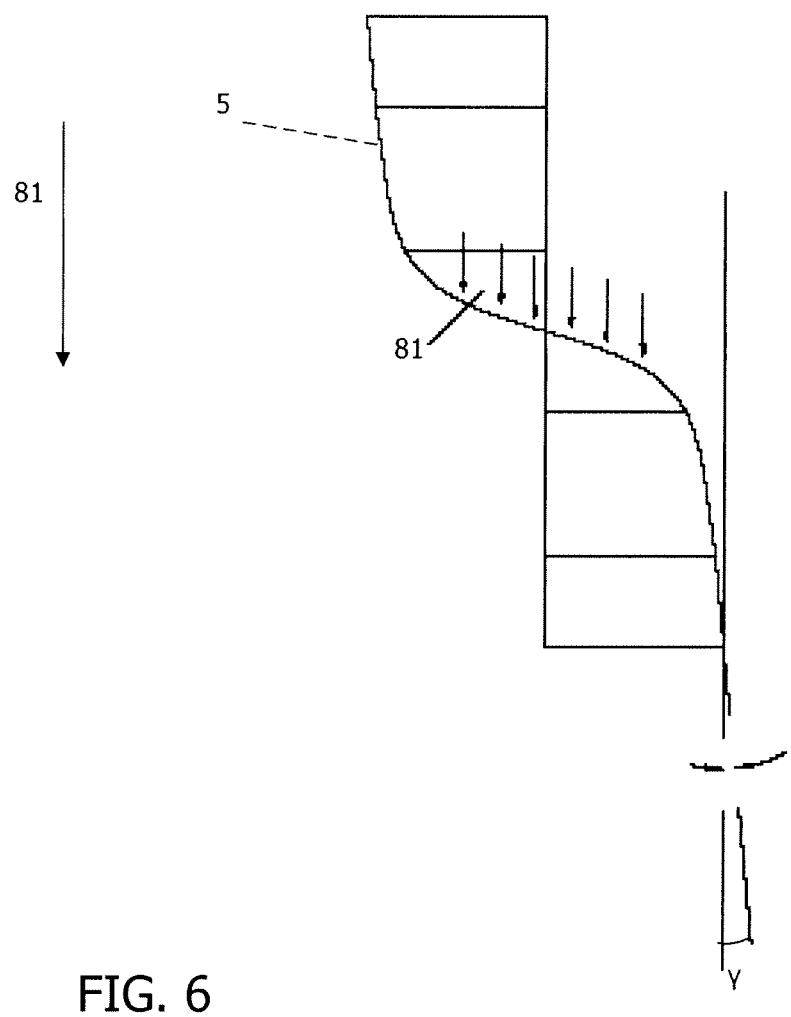

FIG. 6 schematically represents a path followed by grooves and ribs of a tampon according to the invention in the longitudinal (axial) direction y of the tampon.

Figure 7A:
Figure 7B:
Figure 7C:

FIGS. 7A, 7B and 7C show the outer longitudinal paths of grooves having single points of inflection. The tampons show 4, 6 and 8 grooves respectively.

Figure 8A:
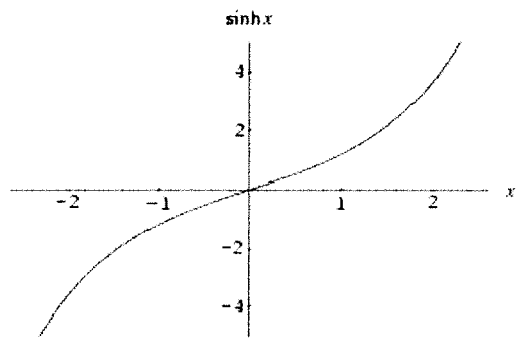
Figure 8B:
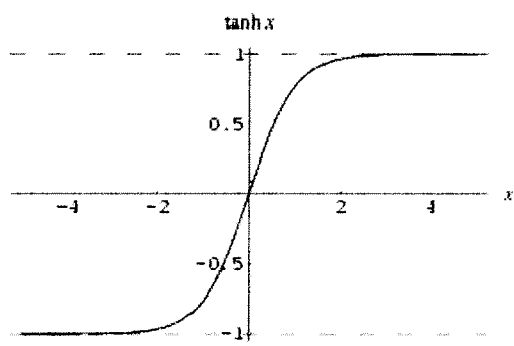
Figure 8C:
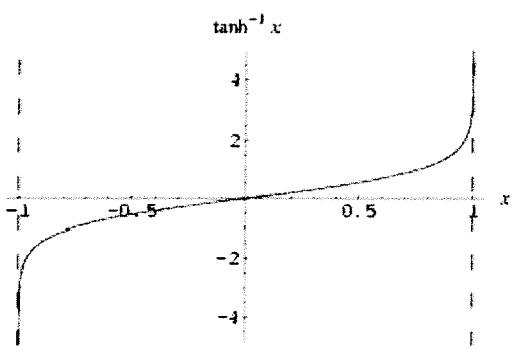

FIGS. 8A to C respectively represents a function corresponding to a hyperbolic sine of x, a hyperbolic tangent of x, and an inverse hyperbolic tangent of x.

Figure 9A:
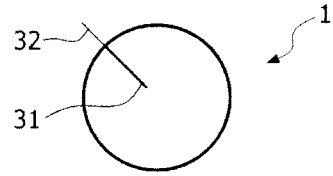
Figure 9B:
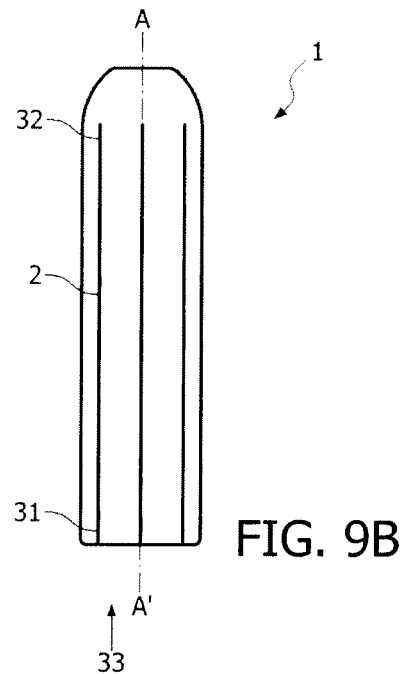

FIGS. 9A and 9B show the tampon of FIGS. 1A and 1B, whereby the distal (insertion) 32 and proximal (withdrawal) 31 end points of the outer longitudinal path 2 coincide when viewed along axis A-A'.

Figure 10A:
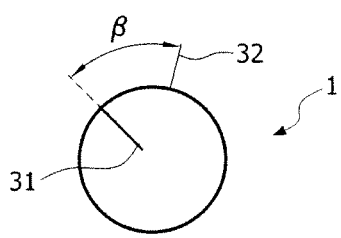
Figure 10B:
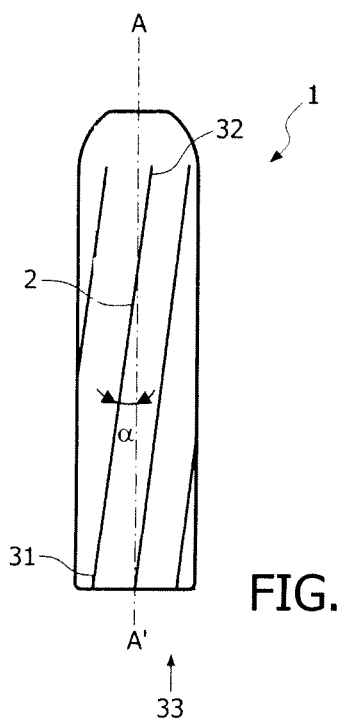

FIGS. 10A and 10B show a tampon of the invention, whereby the distal (insertion) 32 and proximal (insertion) 31 end points of the outer longitudinal path 2 do not coincide when viewed along axis A-A', giving rise to a tampon whereby the closed entrance to the groove is inclined.

Figure 11:
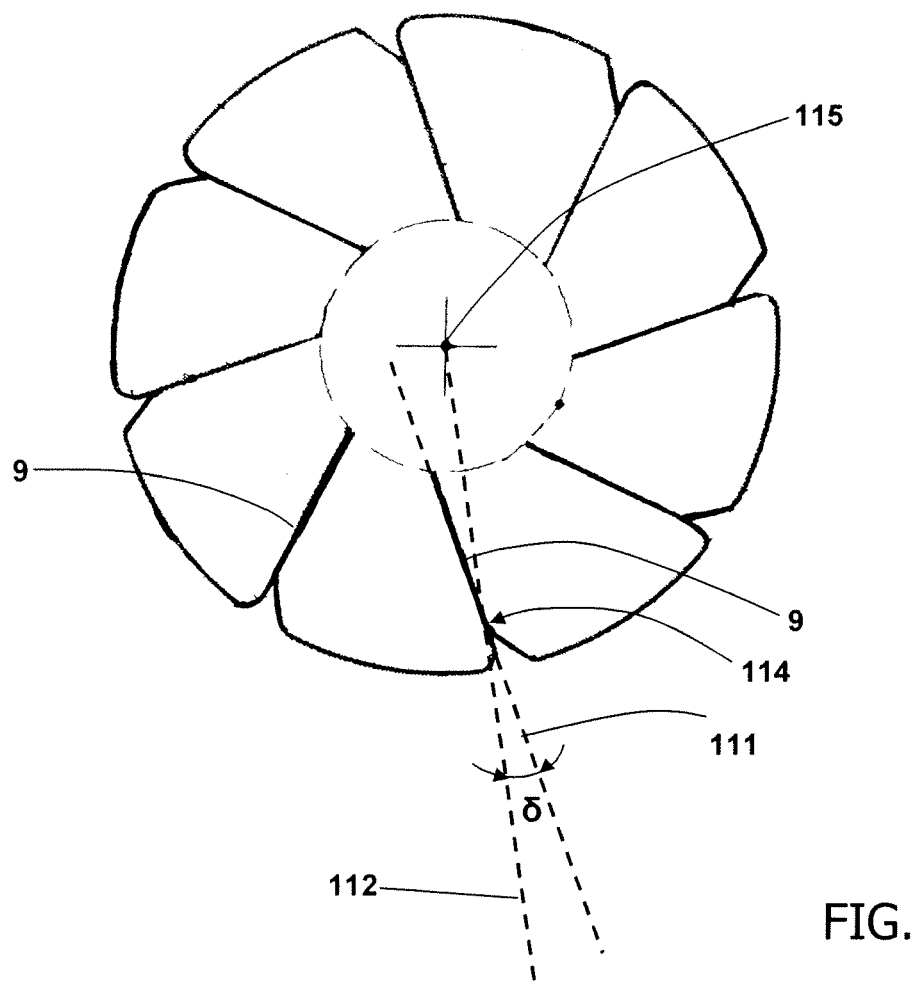

FIG. 11 shows a transverse section of a tampon, whereby the radius of a groove 112 is divergent from the transverse path of a groove 111.

FIGS. 12A to 12H show the path of the groove along planes (FIGS. 12C and 12F) defined by the x- and y-axis, at a depth along the z-axis when z=0.1 W or 0.3 W, wherein the inner longitudinal path is incomplete below the tampon surface so forming a u-shaped impression profile (FIGS. 12B and 12E).

Figure 13A:
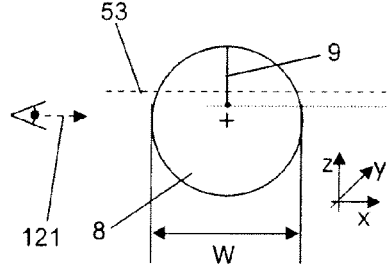
Figure 13B:
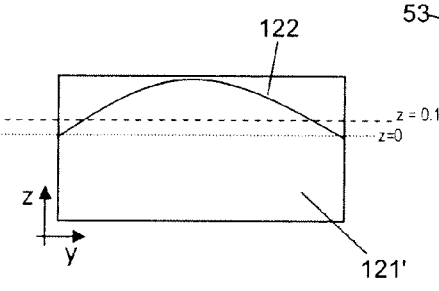
Figure 13C:
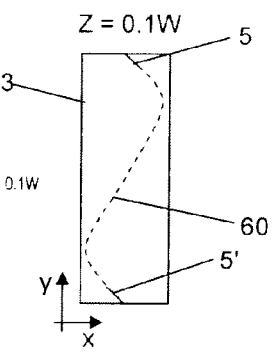
Figure 13D:
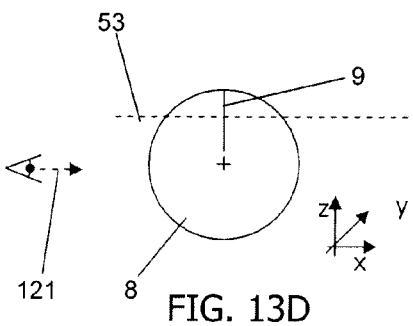
Figure 13E:
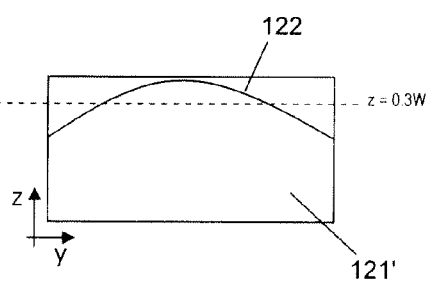

FIGS. 13A to 13H show the path of the groove along planes (FIGS. 13C and 13F) defined by the x- and y-axis, at a depth along the z-axis when z=0.1 W or 0.3 W, wherein the inner longitudinal path is incomplete below the tampon surface so forming an n-shaped impression profile (FIGS. 13B and 13E).

FIGS. 14A to 14H show the path of the groove along planes (FIGS. 14C and 14F) defined by the x- and y-axis, at a depth along the z-axis when z=0.1 W or 0.3 W, wherein the inner longitudinal path is incomplete below the tampon surface so forming an undulating impression profile (FIGS. 14B and 14E).

FIGS. 15-1A to 15-1E show the transverse midline of a groove 85 being the straight line drawn, in a composite view 84 (FIG. 15E) of a groove of a tampon 1 transverse (B-B') cross-section through the midpoint of the inner extremity 86 of the groove and the midpoint of the groove 86 on surface, whereby the composite view 84 of the groove forms the outline of a fan.

FIGS. 15-2A to 15-2D show the transverse midline of a groove 85 being the straight line drawn, in a composite view 84 (FIG. 15-2D) of a groove of a tampon 1 transverse (B-B') cross-section through the midpoint of the inner extremity 86 of the groove and the midpoint of the groove 86 on surface, whereby the composite view 84 of the groove forms the outline of an inverted fan.

FIGS. 15-3A to 15-3D show the transverse midline of a groove 85 being the straight line drawn, in a composite view 84 (FIG. 15-3D) of a groove of a tampon 1 transverse (B-B') cross-section through the midpoint of the inner extremity 86 of the groove and the midpoint of the groove 86 on the surface, whereby the composite view 84 of the groove forms the outline of an inverted bucket.

Figure 16A:
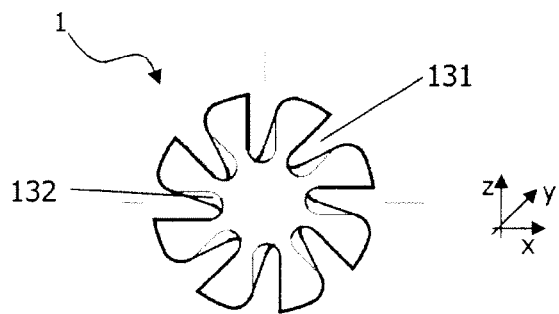
Figures 16B, 16C:
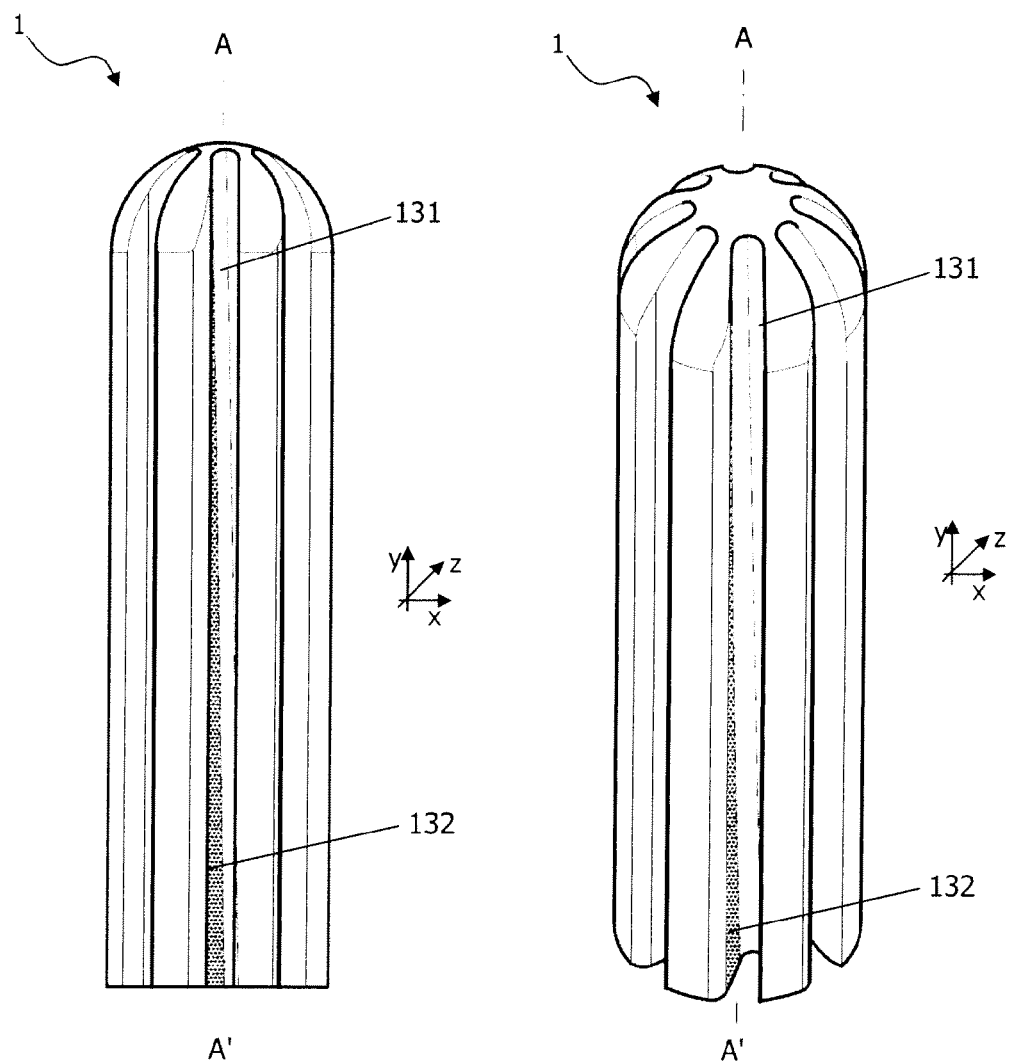

FIGS. 16A to 16C show plan, elevation and perspective view of a tampon of the invention having outer longitudinal path straight and parallel to the y-axis, and with an inner longitudinal path inclined to the y-axis.

Figure 17A:
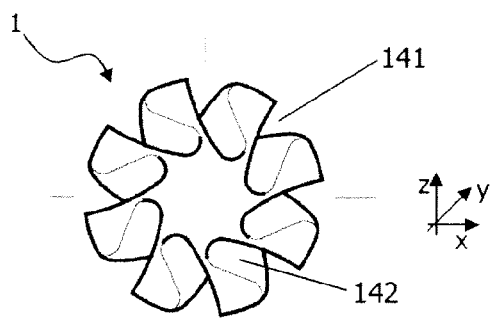
Figure 17B:
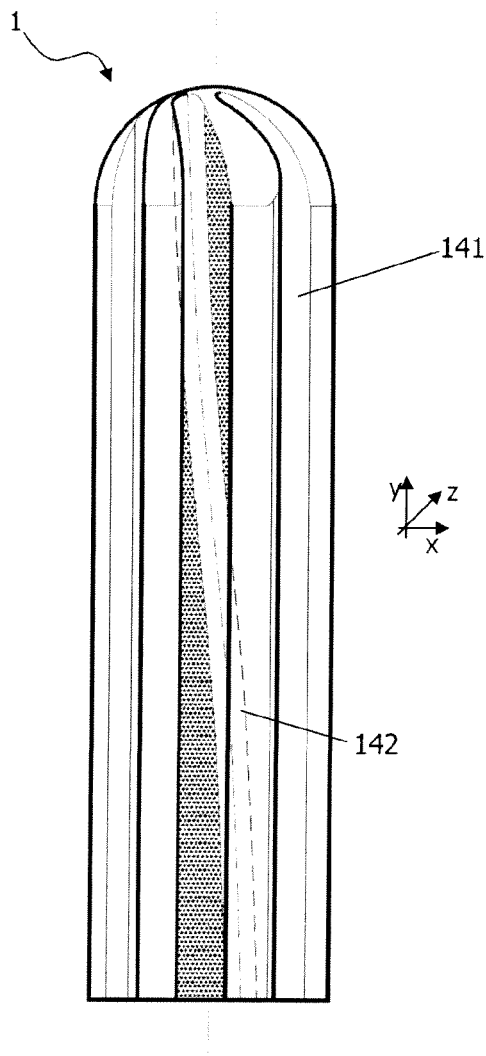
Figure 17C:
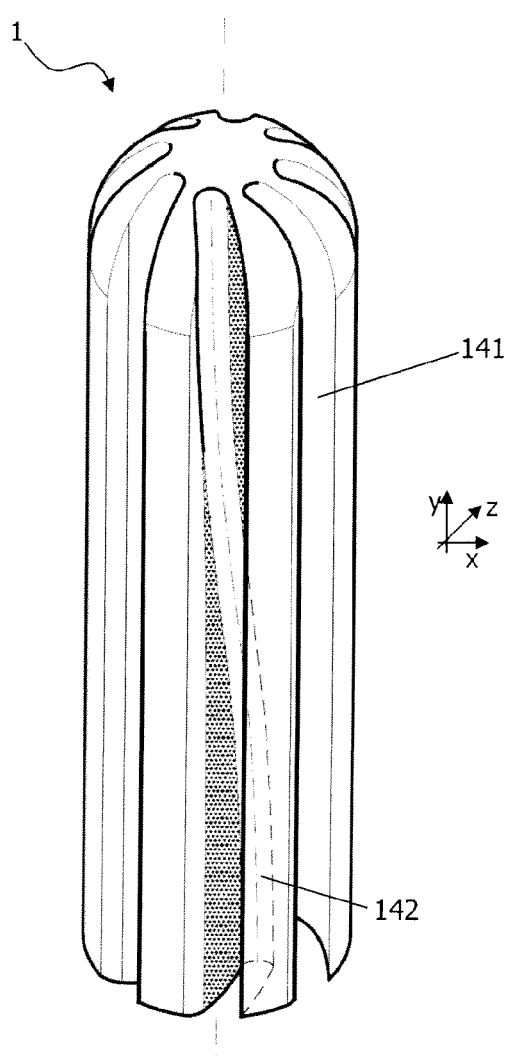

FIGS. 17A to 17C show plan, elevation and perspective view of a tampon of the invention having outer longitudinal path straight and parallel to the y-axis, and with a curved inner longitudinal path.

Figure 18:
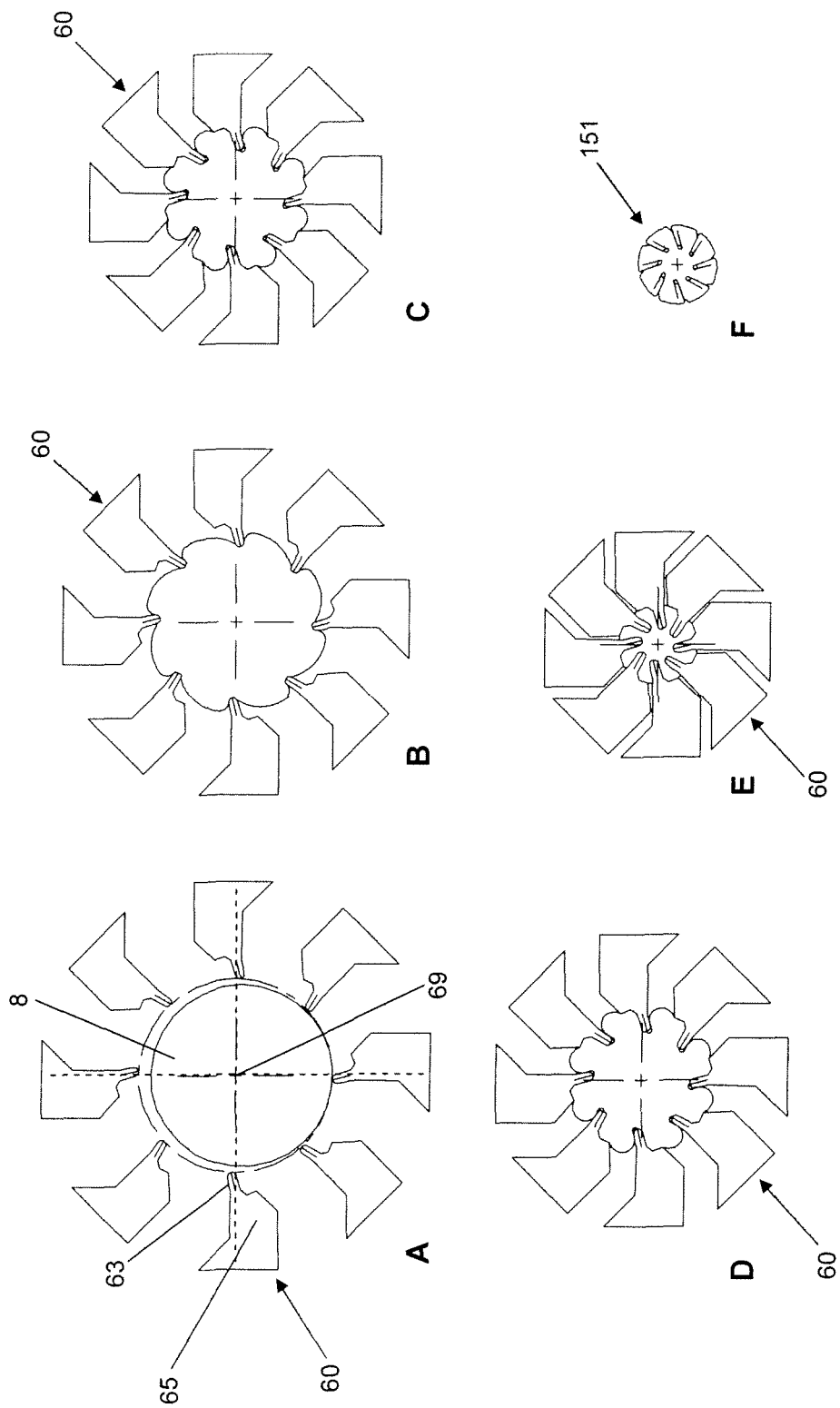

FIGS. 18A to 18E show press jaws of a press according to the invention, each having a penetrating segment protruding from a pressing head, said press jaws in open position, arranged around a central axis of the press (press axis), gradually closing and penetrating the tampon blank shown in cross section, resulting in a pressed tampon in FIG. 18F.

Figure 19:
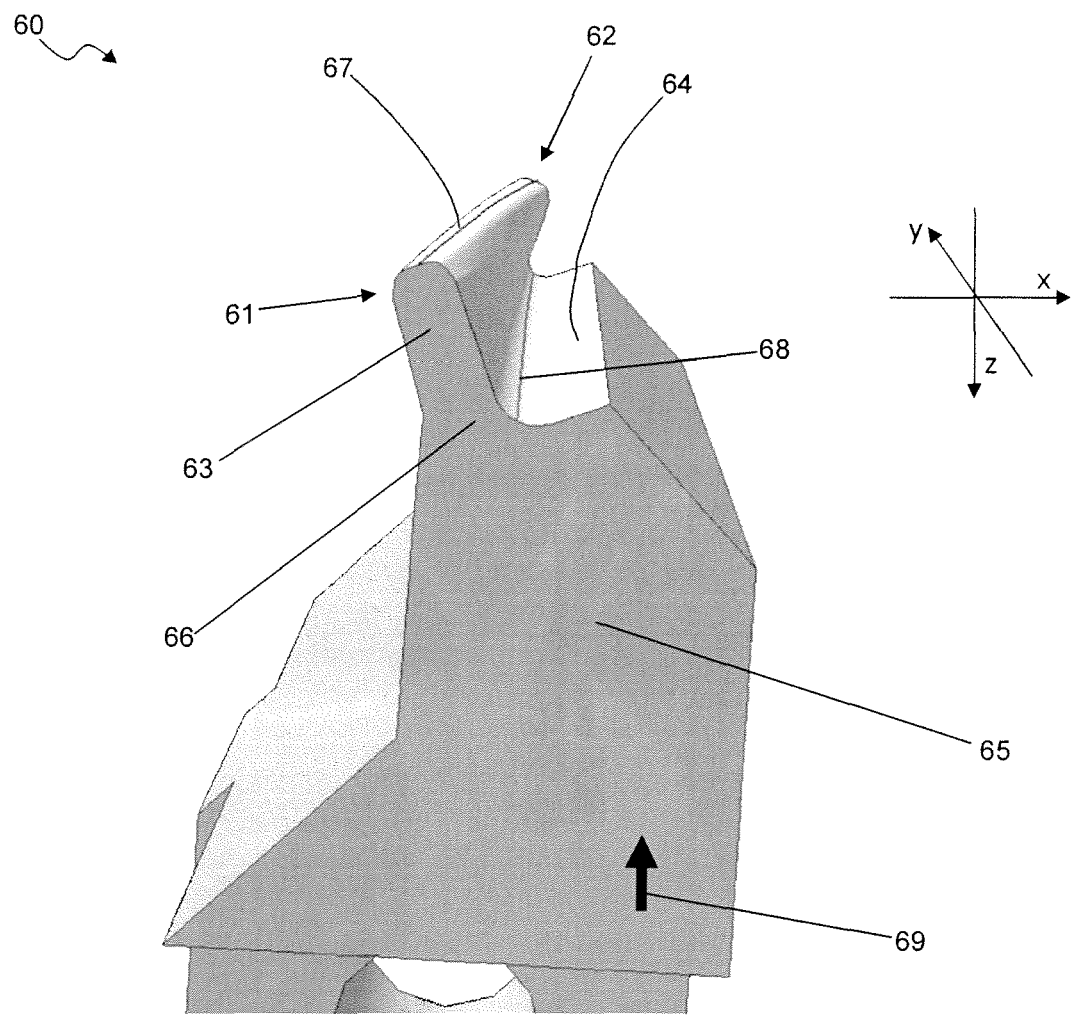

FIG. 19 shows a perspective view of a press jaw according to the present invention.

FIGS. 20A to 20F shows a system for defining the penetrating segment longitudinal path along a plane defined by the x- and y-axis, at a depth along the z-axis.

FIGS. 20A and 20B depict a plane of penetrating segment close to the extremity of the penetrating segment showing an inclined longitudinal path.

FIGS. 20C and 20D depict a plane of penetrating segment, closer to the pressing head compared with FIGS. 20A and 20B, where penetrating segment shows a less inclined longitudinal path.

FIGS. 20E and 20F depict a plane of penetrating segment adjoining the pressing head, and the path of the groove on the surface of the tampon, which appears as a straight line.

Figures 1, 21:
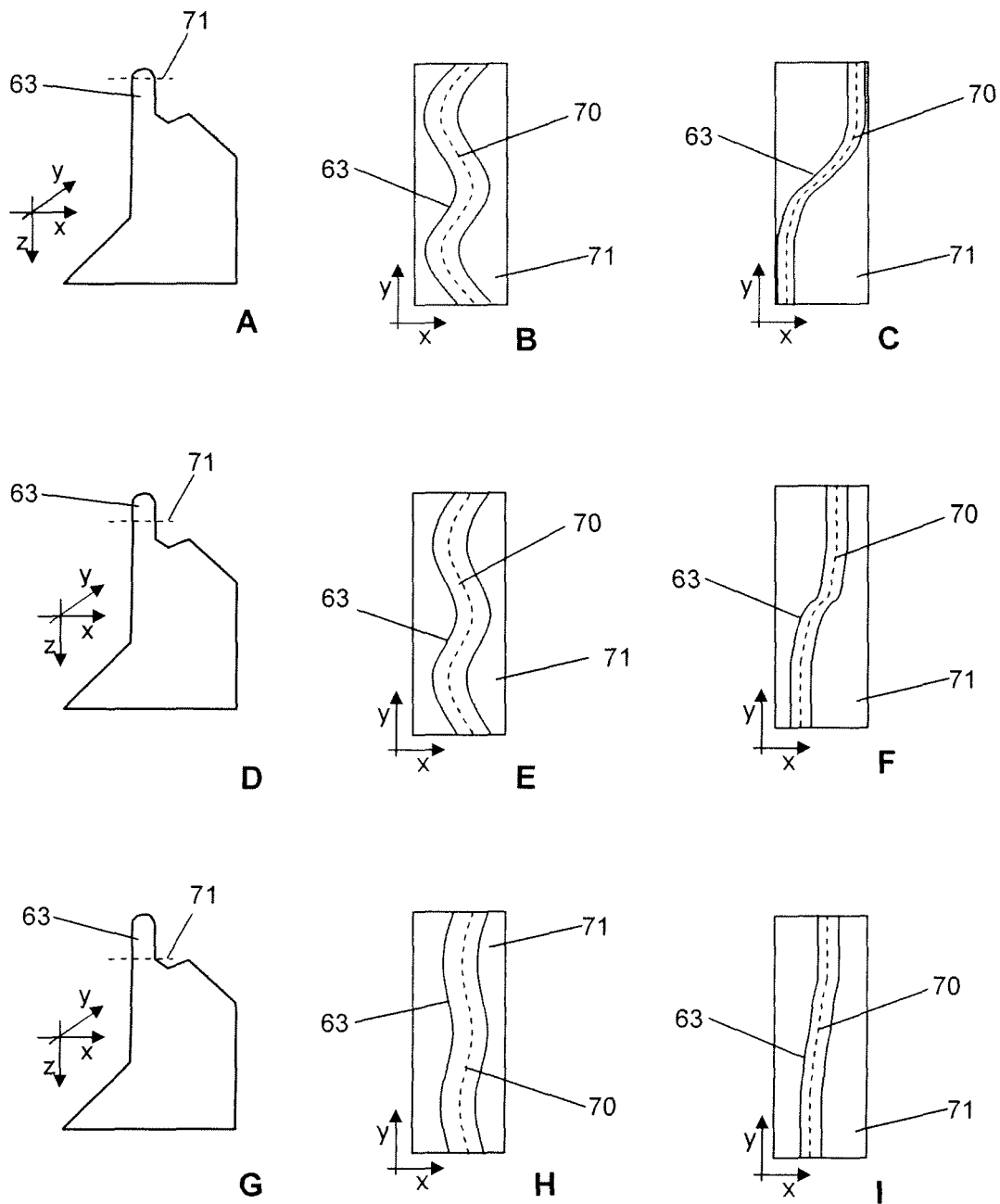

FIGS. 21-1A and 21-1B depict a plane of penetrating segment close to the extremity of the penetrating segment showing an undulating longitudinal path.

FIGS. 21-1D and 21-1E depict a plane of penetrating segment, closer to the pressing head compared with FIGS. 21-1A and 21-1B, where penetrating segment shows an undulating longitudinal path having less amplitude.

FIGS. 21-1G and 21-1H depict a plane of penetrating segment adjoining the pressing head, and the path of the groove on the surface of the tampon, which appears as an undulating longitudinal path having less amplitude still compared with FIG. 21-1E.

FIGS. 21-1A and 21-1C depict a plane of penetrating segment close to the extremity of the penetrating segment showing a curved longitudinal path having one point of inflection.

FIGS. 21-1D and 21-1F depict a plane of penetrating segment, closer to the pressing head compared with FIGS. 21-1A and 21-1B, where penetrating segment shows a curved longitudinal path having one point of inflection, having less amplitude.

FIGS. 21-1G and 21-1I depict a plane of penetrating segment adjoining the pressing head, and the path of the groove on the surface of the tampon, which appears as longitudinal path having one point of inflection having less amplitude still compared with FIG. 21-1F.

FIGS. 21-2A and 21-2B depict a plane of penetrating segment close to the extremity of the penetrating segment showing an undulating longitudinal path.

FIGS. 21-2D and 21-2E depict a plane of penetrating segment, closer to the pressing head compared with FIGS. 21A and 21B, where penetrating segment shows an undulating longitudinal path having more amplitude.

FIGS. 21-2G and 21-2H depict a plane of penetrating segment adjoining the pressing head, and the path of the groove on the surface of the tampon, which appears as an undulating longitudinal path having more amplitude still compared with FIG. 21-2E.

FIGS. 21-2A and 21-2C depict a plane of penetrating segment close to the extremity of the penetrating segment showing a curved longitudinal path having one point of inflection.

FIGS. 21-2D and 21-2F depict a plane of penetrating segment, closer to the pressing head compared with FIGS. 21A and 21B, where penetrating segment shows a curved longitudinal path having one point of inflection, having more amplitude.

FIGS. 21-2G and 21-2I depict a plane of penetrating segment adjoining the pressing head, and the path of the groove on the surface of the tampon, which appears as longitudinal path having one point of inflection having more amplitude still compared with FIG. 21-2F.

Figure 22:
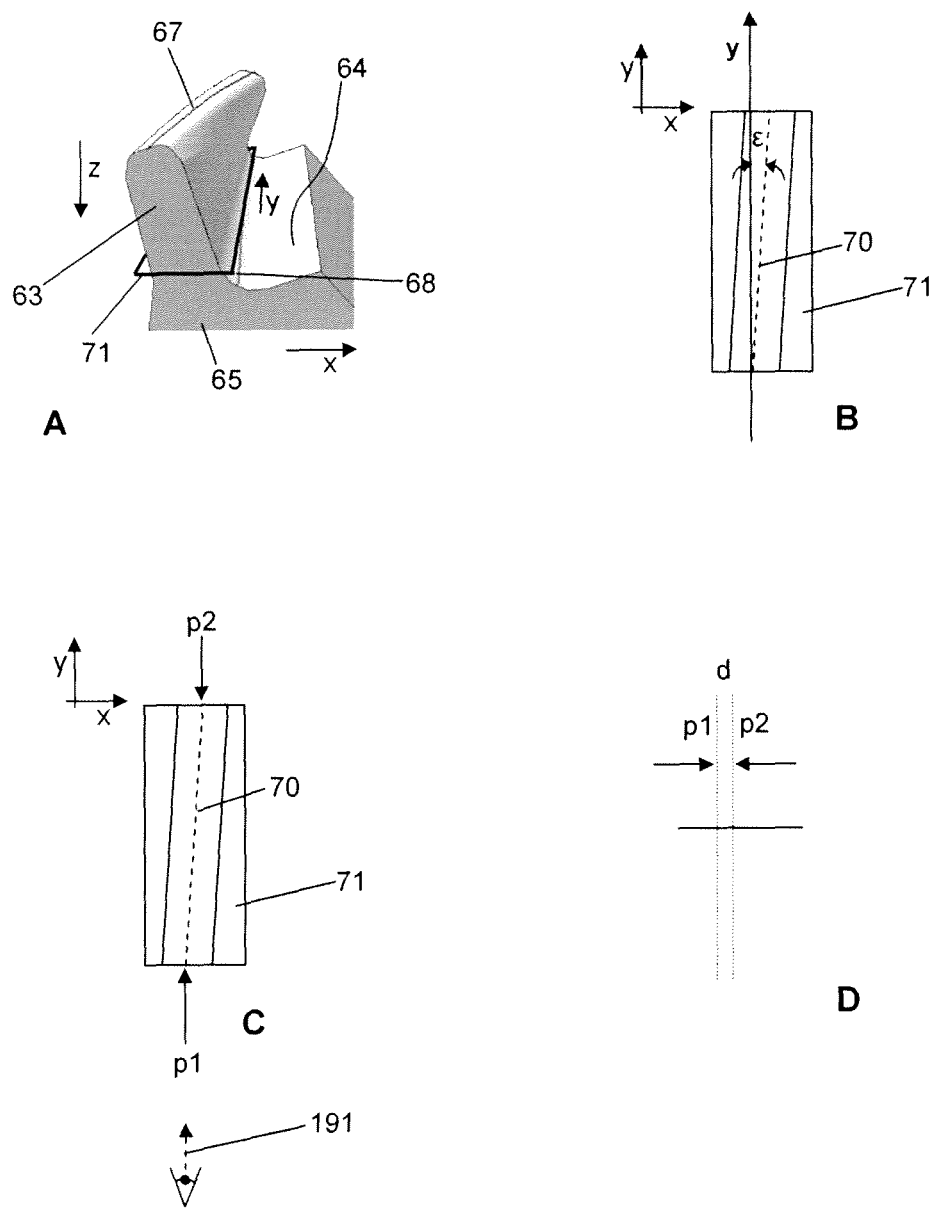

FIGS. 22A to 22D depicts the inclination of the penetrating segment outer longitudinal path as an angle (FIG. 22B), or as a distance (FIG. 22 C or D).

Figure 23A:
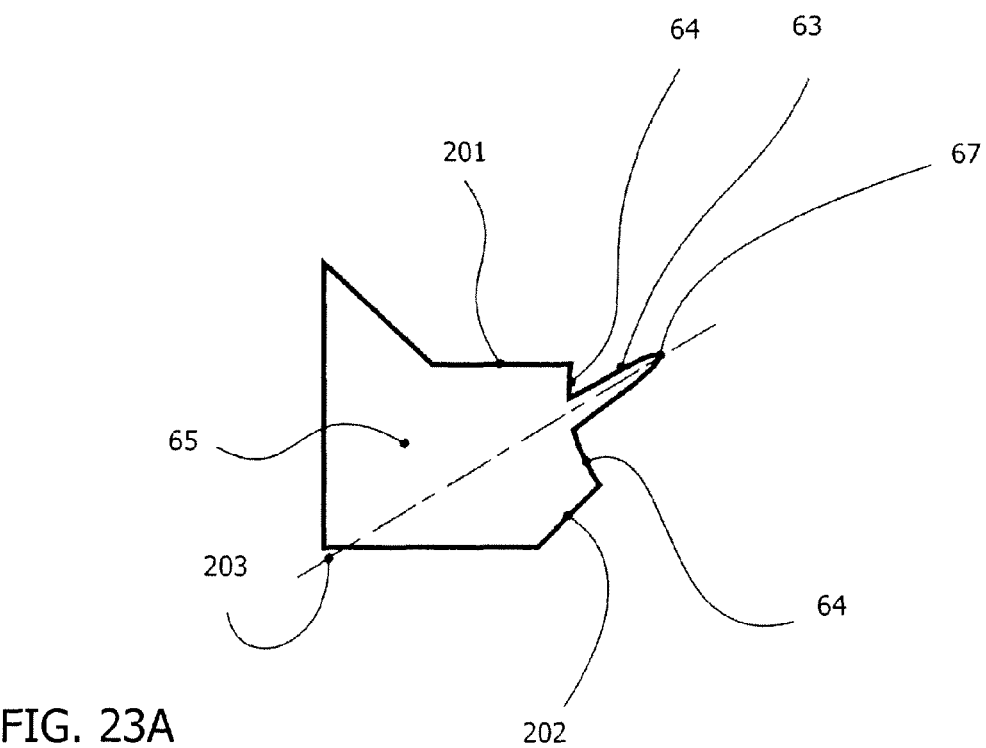

FIG. 23A shows a cross-section of a press jaw, and the median of a penetrating segment.

Figures 23B, 23C, 23D:
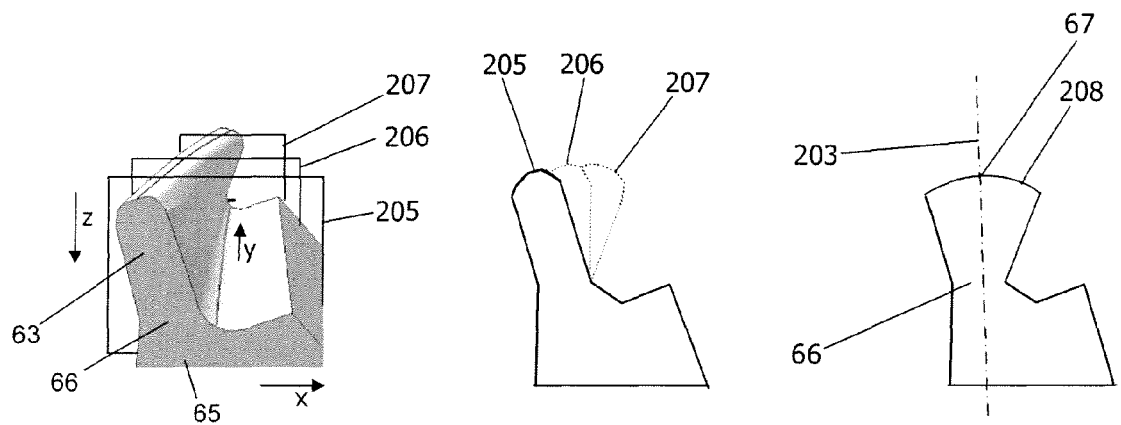

FIG. 23B shows a perspective view of press jaw, and the median of a penetrating segment drawn across a composite cross-section (FIG. 23D) comprising sections (FIG. 23C) along the y-axis of the press jaw.

Figure 24:
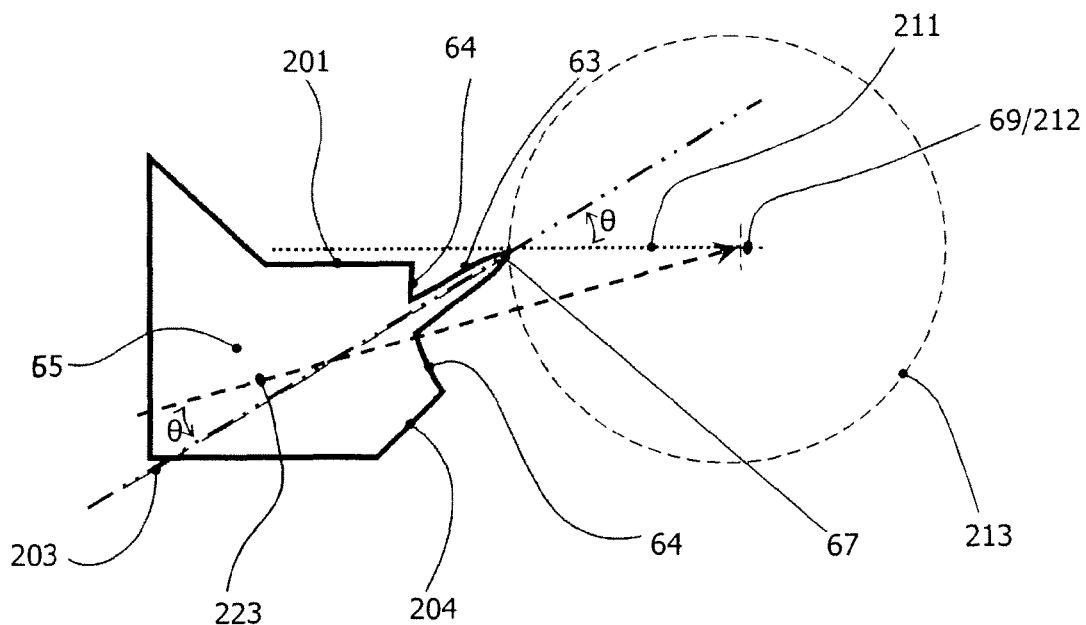

FIG. 24 shows a press jaw with a line of movement towards the press axis, and a median of the penetrating segment divergent from the line.

Figure 25:
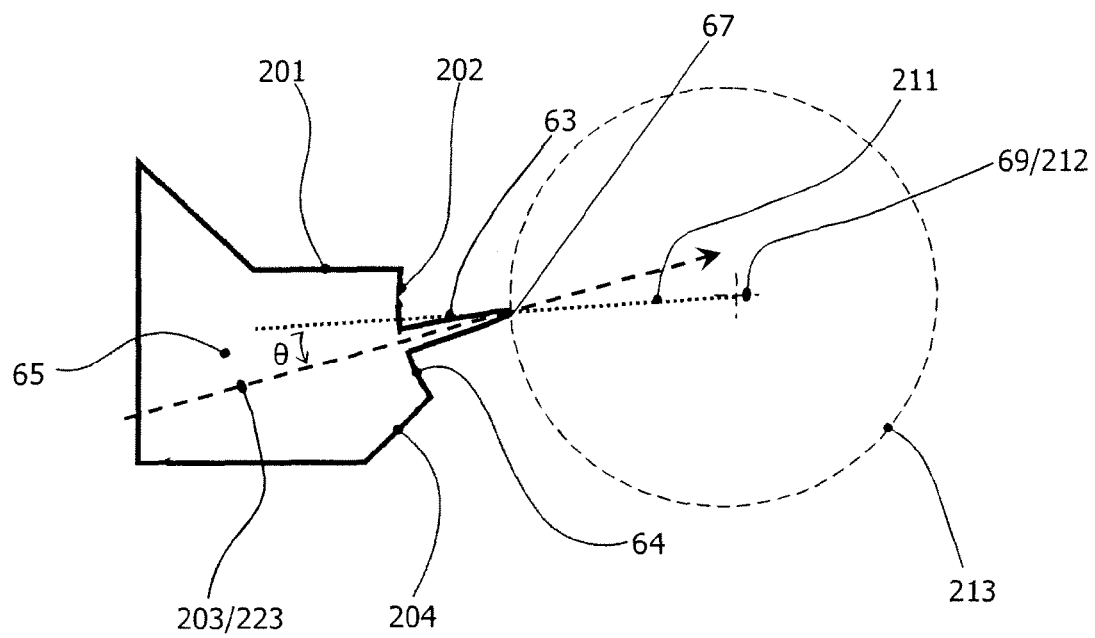

FIG. 25 shows a press jaw with a line of movement divergent from press axis, and a median of the penetrating segment parallel with the line.

Figure 26:
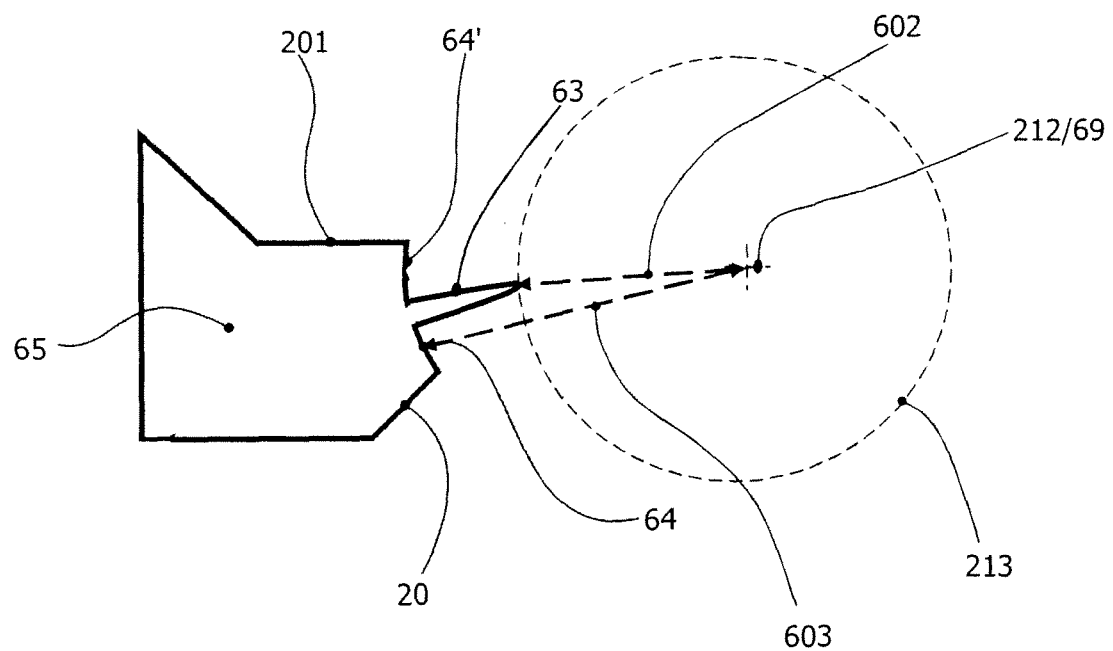

FIG. 26 shows a press jaw with indications measuring the impression depth.

Figure 27:
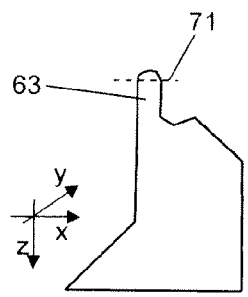
Figure 27:
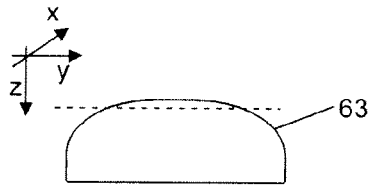
Figure 27:
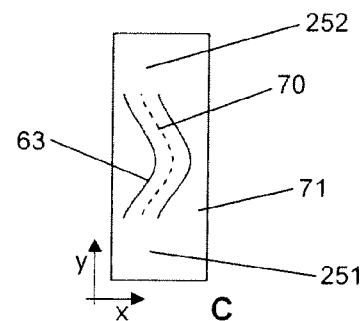
Figure 27:
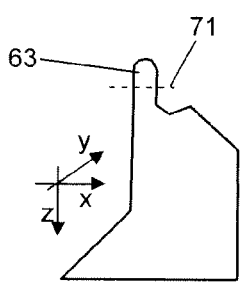
Figure 27:
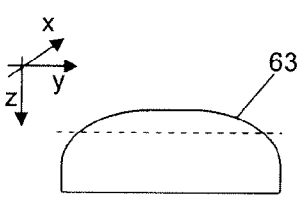
Figure 27:
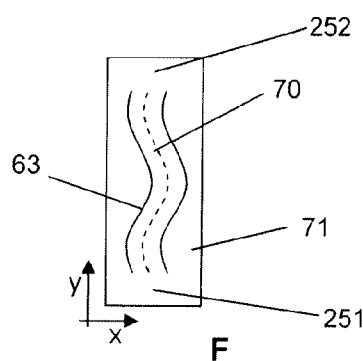
Figure 27:
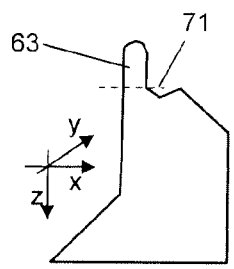
Figure 27:
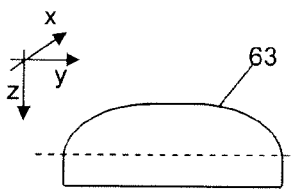
Figure 27:
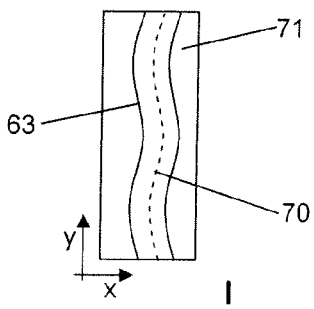

FIGS. 27A to I show the penetrating segment longitudinal path along a plane defined by the x- and y-axis, at a depth along the z-axis, wherein the penetrating segment longitudinal path is incomplete below the tampon surface, giving rise to a u-shape impression profile in the tampon. The incomplete penetrating segment longitudinal path is depicted in FIGS. 27C and 27F and the corresponding profile of the penetrating segment viewed as a projection in the y-z plane is show in FIGS. 27B and 27E.

Figure 28:
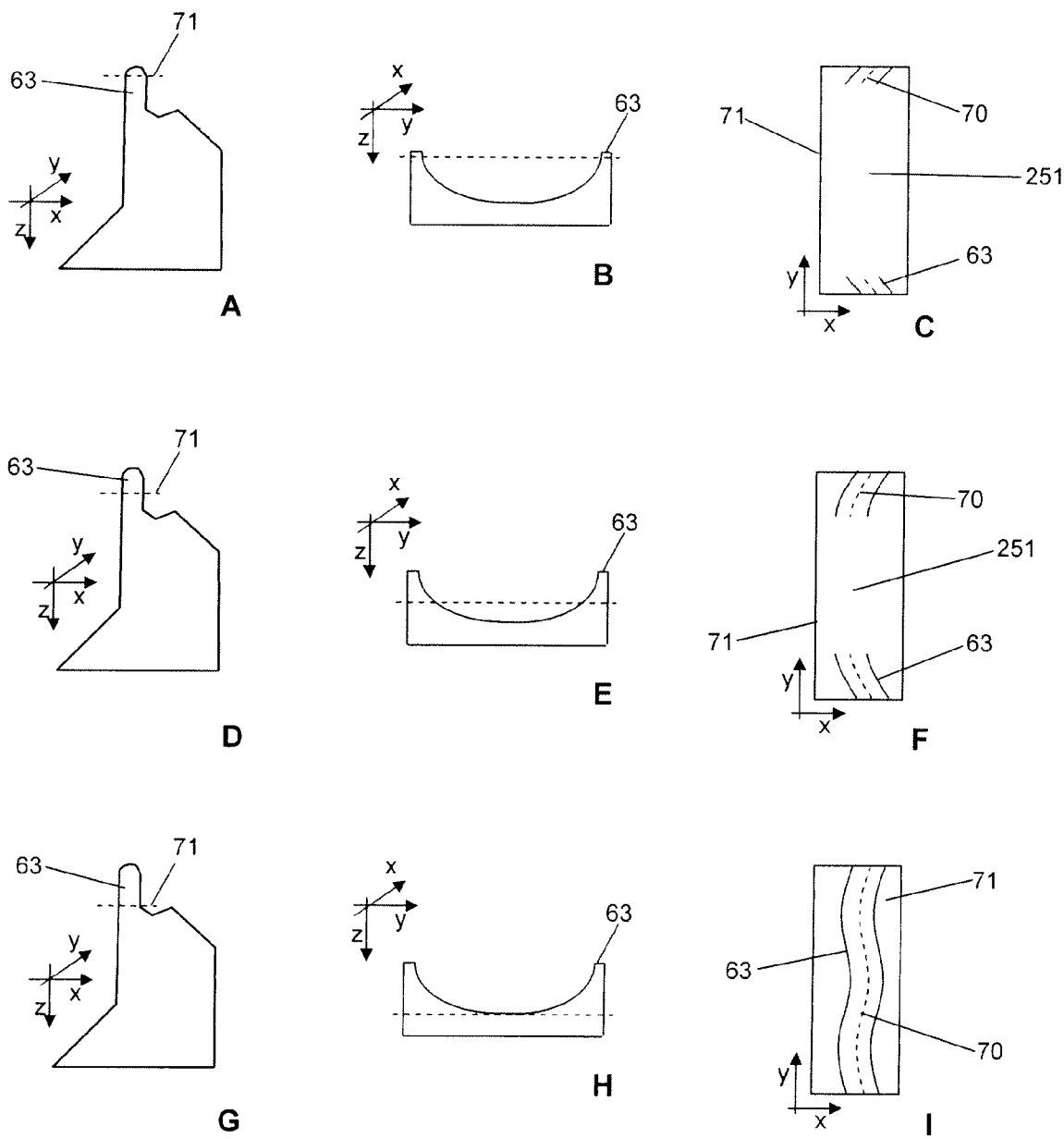

FIGS. 28A to I show the penetrating segment longitudinal path along a plane defined by the x- and y-axis, at a depth along the z-axis, wherein the penetrating segment longitudinal path is incomplete below the tampon surface, giving rise to an n-shape impression profile in the tampon. The incomplete penetrating segment longitudinal path is depicted in FIGS. 28C and 28F and the corresponding profile of the penetrating segment viewed as a projection in the y-z plane is shown in FIGS. 28B and 28E.

Figure 29:
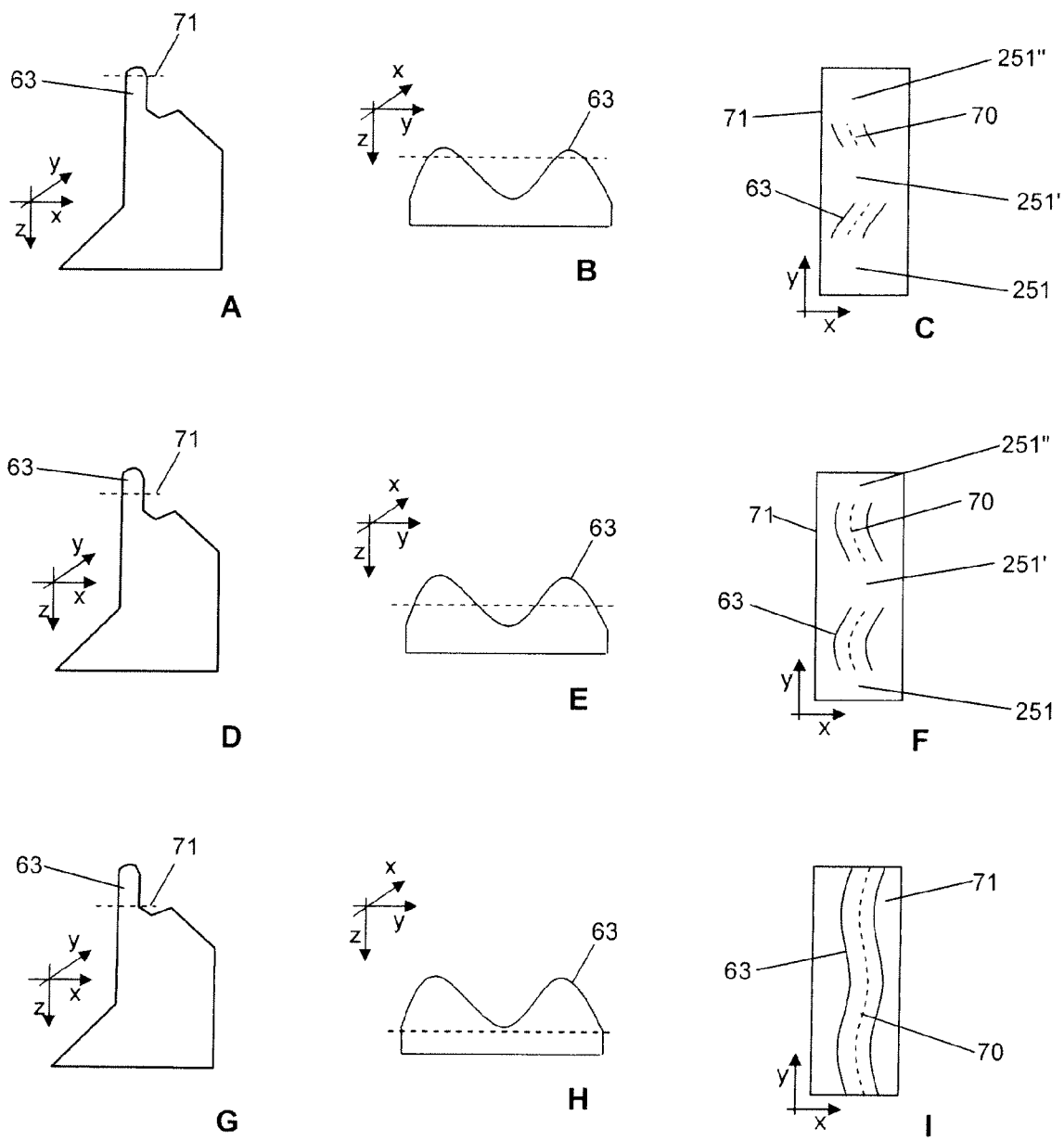

FIGS. 29A to 29I show the penetrating segment longitudinal path along a plane defined by the x- and y-axis, at a depth along the z-axis, wherein the penetrating segment longitudinal path is incomplete below the tampon surface, giving rise to an undulating-shape impression profile in the tampon. The incomplete penetrating segment longitudinal path is depicted in FIGS. 29C and 29F and the corresponding profile of the penetrating segment viewed as a projection in the y-z plane is shown in FIGS. 29B and 29E.

Figure 30A:
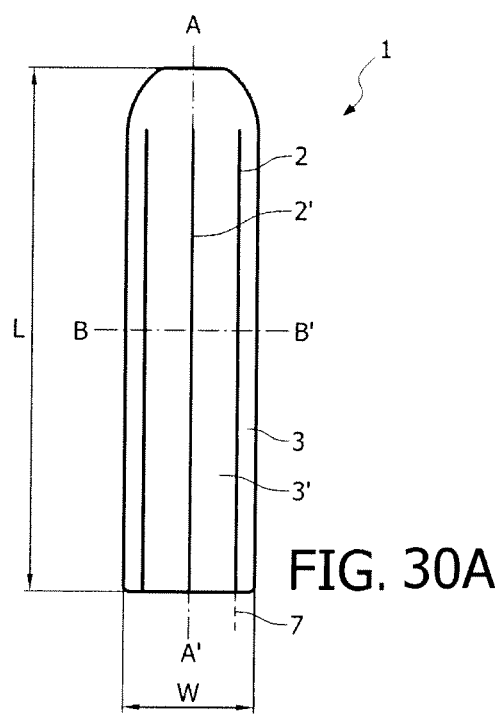

FIG. 30A shows an illustration of a tampon 1 of the invention, disposed with longitudinal grooves where each outer longitudinal paths 2 is parallel to the longitudinal groove axis 7.

Figure 30B:
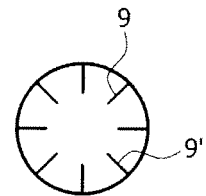

FIG. 30B shows a view of the tampon of FIG. 30A end on, across a transverse section along line B-B'.

Figure 31A:
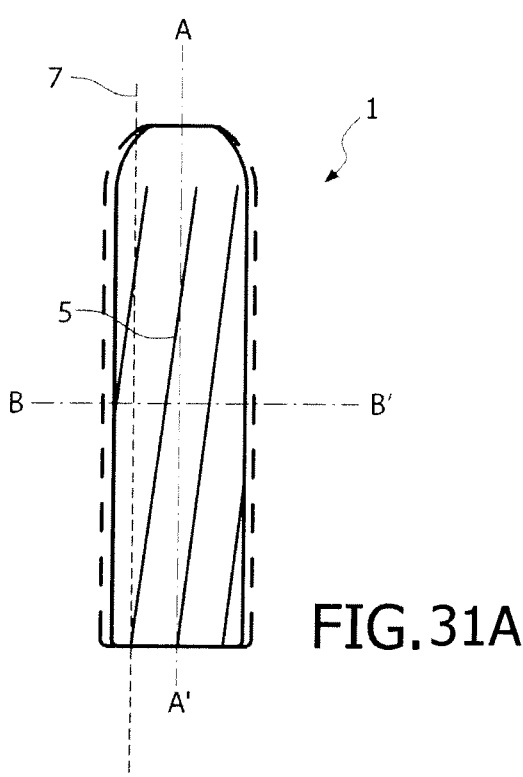

FIG. 31A shows an illustration of a tampon 1 of FIG. 30A, below the surface each inner longitudinal path 5 is inclined to the longitudinal groove axis 7.

Figure 31B:
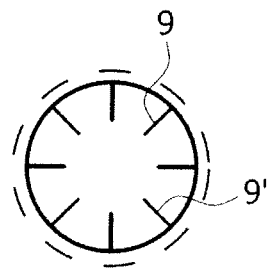

FIG. 31B shows a view of the tampon of FIG. 31A end on, across a transverse section along line B-B'.

Figures 32A, 32B:
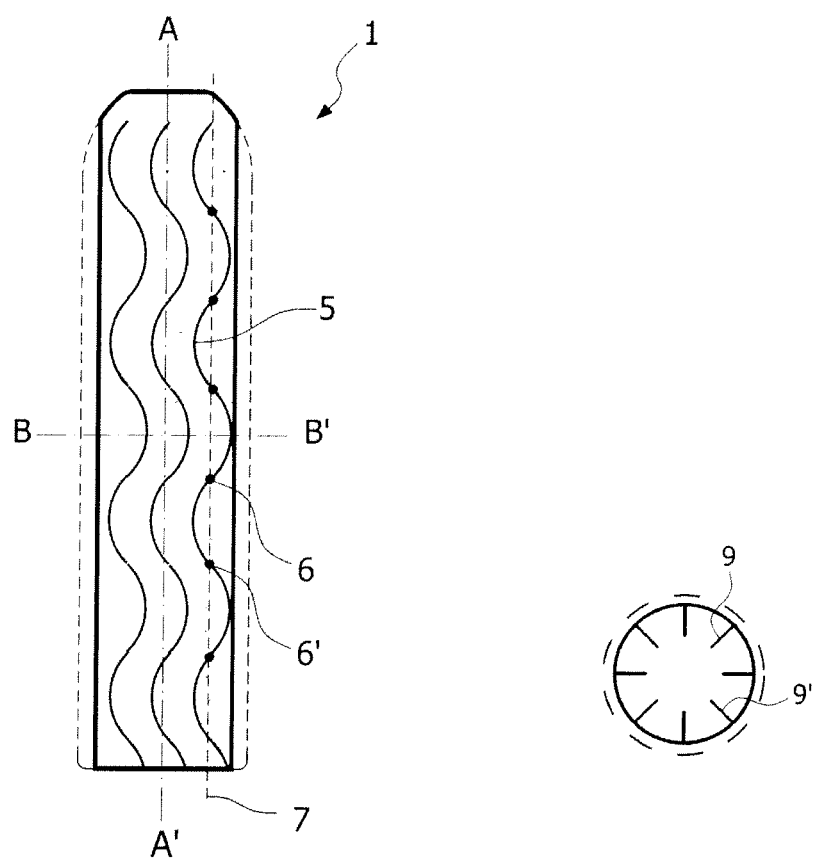

FIG. 32A shows an illustration of a tampon 1 of FIG. 30A, below the surface, whereby the closed longitudinal grooves describe a curved inner longitudinal path 5, which path has numerous points of inflection 6, 6'.

FIG. 32B shows a view of the tampon of FIG. 32A end on, across a transverse section along line B-B'.

Figure 33A:
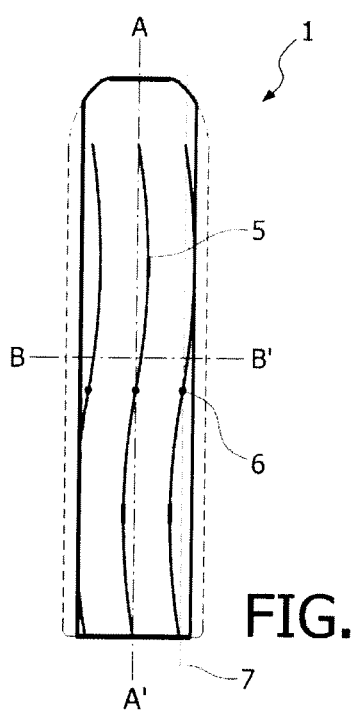

FIG. 33A shows an illustration of a tampon 1 of FIG. 30A, below the surface, whereby the closed longitudinal grooves describe a curved inner longitudinal path 5, which path has a single point of inflection 6.

Figure 33B:
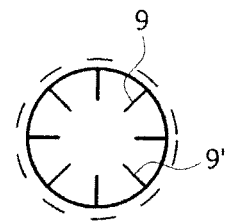

FIG. 33B shows a view of the tampon of FIG. 33A end on, across a transverse section along line B-B'.

FIGS. 34A to 34B show the x1,y1,z1 coordination system for defining the path of the groove along a plane defined by the x1- and y1-axis, at a depth along the z1-axis. FIG. 34A depicts the path of the closed groove on the surface of the tampon, when z1=0 (FIG. 34B).

FIG. 35A depicts the path of the groove below the surface of the tampon, when, arbitrarily, z1=0.2 W (FIG. 35B); at a deeper groove depth, the curvature of the inner longitudinal path increases compared with FIG. 34A.

Figure 36A:
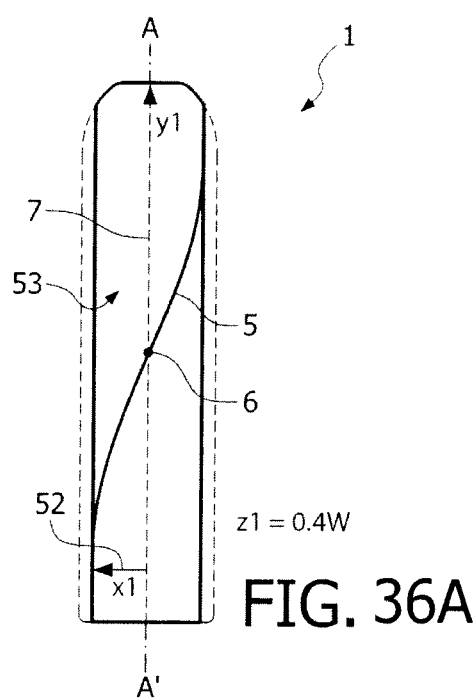

FIG. 36A depicts the path of the closed groove below the surface of the tampon, when, arbitrarily, z1=0.4 W (FIG. 36B); at a deeper groove depth, the curvature of the inner longitudinal path increases compared with FIG. 35B.

FIG. 37B shows a surface view of a tampon of the invention, whereby the distal (insertion) 32 and proximal (withdrawal) 31 end points of the outer longitudinal path 2 coincide when viewed along axis A-A' (FIG. 37A).

FIG. 38B shows a surface view of a tampon of the invention, whereby the distal (insertion) 32 and proximal (withdrawal) 31 end points of the outer longitudinal path 2 do not coincide when viewed along axis A-A' (FIG. 38A), giving rise to a tampon whereby the closed entrance to the groove is inclined.

Figure 39:
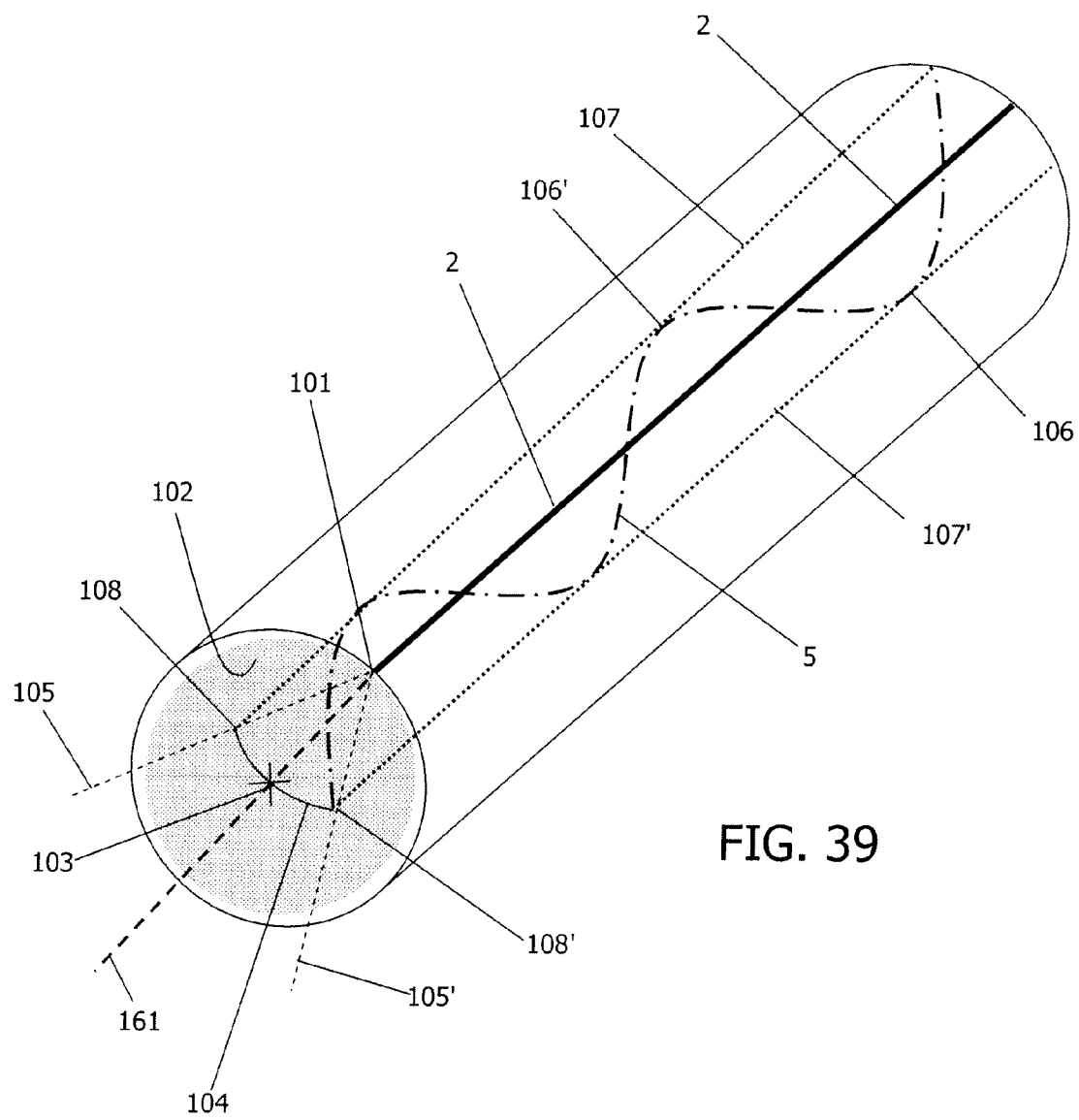

FIG. 39 shows a schematic view of a tampon illustrating the amplitude median 111.

Figure 40A:
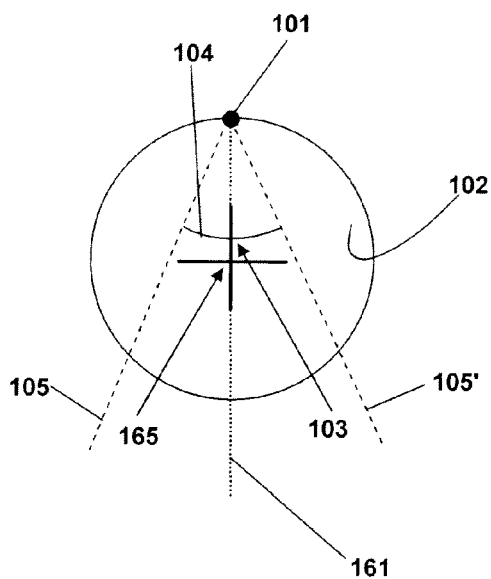
Figure 40B:
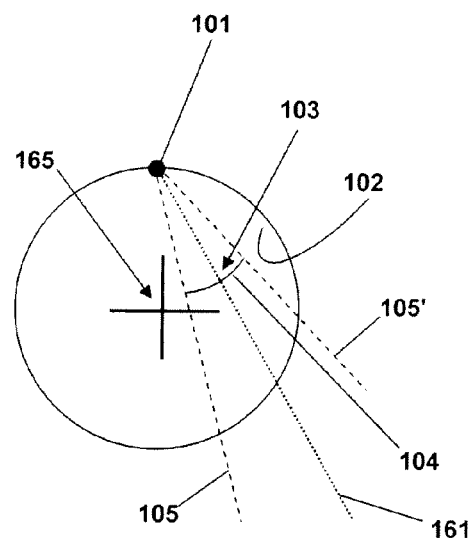

FIGS. 40A and 40B show a transverse section of a tampon, whereby amplitude median 161 crosses the midpoint 165 of the tampon (FIG. 40A) or whereby the amplitude median 161 is divergent from the midpoint 165 (FIG. 40B).

Figure 41:
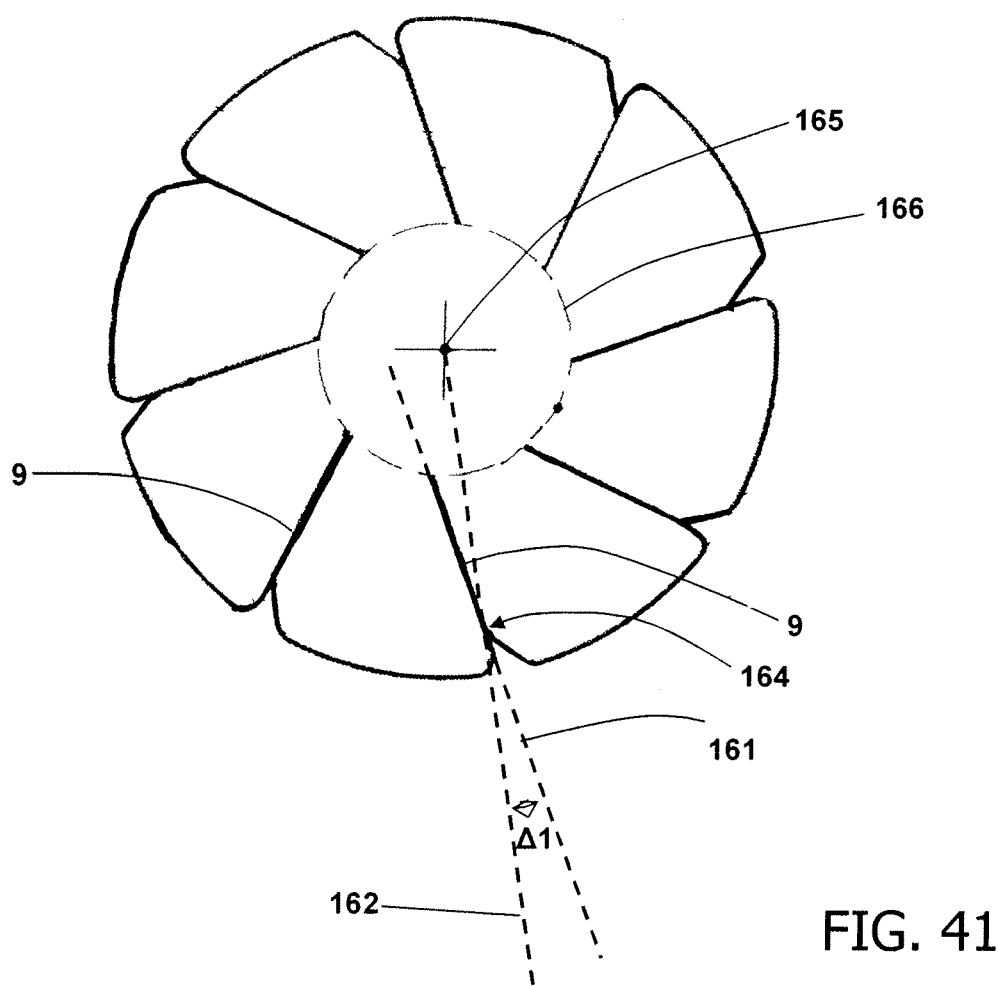

FIG. 41 depicts a transverse (B-B') cross-section of the tampon of the invention, indicating the amplitude median divergent from the radius of the groove.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and an are used herein to refer to one or to more than one, i.e. to at least one of the grammatical object of the article. By way of example, "a groove" means one groove or more than one groove.

The recitation of numerical ranges by endpoints includes all integer numbers and, where appropriate, fractions subsumed within that range (e.g. 1 to 5 can include 1, 2, 3, 4 when referring to, for example, a number of grooves, and can also include 1.5, 2, 2.75 and 3.80, when referring to, for example, angles). The recitation of end points also includes the end point values themselves (e.g. from 1.0 to 5.0 includes both 1.0 and 5.0)

The present invention relates to a tampon 1 suitable for feminine hygiene and medical purpose having a longitudinal body in a tubular shape, that may be cylindrical, conical, ellipsoidal, hourglass, or other suitable shape. In compressed condition, the tampon has a length L and a width W. The tampon is provided with an insertion end 11 and a withdrawal end 14. The term "length of the tampon" refers to the length in longitudinal direction A-A' (FIG. 1A) of the tampon body. The length is typically measured from the tip of the insertion end 11 to the tip of the withdrawal end 14. The term "width of the tampon" refers to the width of the tampon body in transversal direction B-B' (FIG. 1B) in compressed condition. This will generally be equal to the diameter of the tampon. The width of the tampon might vary depending on the location along the longitudinal axis it is measured when the body is conical, ellipsoidal, hourglass or a shape other than cylindrical; in such case the width is taken to mean the maximum width (e.g. maximum diameter). When depth is referred to, it refers to the depth from the surface 13 of the tampon 1 to the core 12.

The tampon essentially consists of compressed absorbent fibrous material and has an outer circumferential surface which is at least partially provided with longitudinal ribs 3, 3' defined by longitudinal grooves 4, 4'. It is noted that the terms "absorbent fibrous material" and "absorbent fibers" are used herein as synonyms.

The present tampon is in particular characterized in that at least one tampon groove 4 is defined an outer longitudinal path 2 on the surface of the tampon that diverges from the longitudinal path of the groove below the surface of the tampon. More in particular, the present tampon is characterized in that a tampon groove 4 is defined by a plurality of inner longitudinal paths 5, each tracing the longitudinal path of a groove at a given depth, and an outer longitudinal path 2 on the surface of the tampon, and whereby the outer longitudinal path 2 at least partially diverges from at least one inner longitudinal path 5.

The present tampon is in independently or additionally characterized in that at least one tampon groove 4 is defined by a plurality of inner longitudinal paths 5 below the surface of the tampon whereby at least two inner longitudinal paths 5 are different i.e. they diverge from each other. The plurality of inner longitudinal paths may diverge gradually or abruptly in the direction from the core 12 to the surface 13 of the tampon. This is exemplified in FIG. 2A which depicts a possible section of the tampon shown in FIG. 2B below the surface across line C-C', having a curved inner longitudinal path 5 in contrast to having straight lines on the surface (FIG. 1A). The transition of the longitudinal path from the core 12 to the surface 13 appears abrupt in FIGS. 1A and 2A, and is within the scope of the invention, though preferably the transition of longitudinal path from the core to the surface is gradual as depicted in FIGS. 3 to 5. Although it is mentioned that at least two inner longitudinal paths 5 are divergent, it may in practice be the case that the majority of inner longitudinal paths gradually diverge e.g. 55%, 60%, 70%, 80%, 90% of inner longitudinal paths. The majority of inner longitudinal paths that gradually diverge may be closest to the core 12 of the tampon 1. Alternatively, the majority of inner longitudinal paths that gradually diverge may be closest to the surface 13 of the tampon 1. As mentioned, the change is preferably gradual, though abrupt changes are also within the scope of the invention. The shape of the groove on the outer surface may be any e.g. straight, parallel to the longitudinal (A-A') axis, inclined to the longitudinal axis, undulated, curved with a single point of inflection. Preferably the change gives rise to a path length that decreases in the direction from the core 12 to the surface 13 of the tampon; this is preferably the case for said majority of inner longitudinal paths 5.

The inner longitudinal path 5 of a groove describes a longitudinal path below the surface of the tampon which corresponds to a line (5, FIG. 2A). The inner longitudinal paths 5 stack the direction from the core 12 to the surface 13 so forming the shape of the groove 4. The inner longitudinal path 5 is generally measured parallel to the longitudinal axis of the tampon. The outermost inner longitudinal path 5 is just below the surface of the tampon. It is typically the line just below the surface of the tampon where lips of a groove come together. The inner longitudinal path 5 (e.g. FIGS. 3-1A to 3-1D) of a groove may be defined as the longitudinal path of a groove across an x-y plane 53 of a tampon which plane is a slice perpendicular to the z-axis 53. The y-axis is parallel to the longitudinal axis of the tampon, the z-axis lies along a transverse midline of the groove 85, and the x-axis is perpendicular to the y and z axes.

The transverse midline of a groove 85 is the straight line drawn, in a composite view 83 (FIG. 15-1E) of a tampon 1 transverse (B-B') cross-section whereby cross-sections (e.g. 80, 81, 82, FIG. 15-1B to 15-1D) of a tampon along the longitudinal axis (A-A') are overlaid (88, FIG. 15E) to form said composite view of a groove 84 (FIG. 15E), through the midpoint of the inner extremity 86 of a composite view of the groove 84 and the midpoint 87 of the composite view of the groove 84 on surface in composite view 83. Said overlays are preferably aligned along the central axis 89 of the tampon which has a constant position in cross-section. The transverse midline of a groove 85 may lies along the radius of a groove or may be divergent therefrom.

Figures 2, 21:
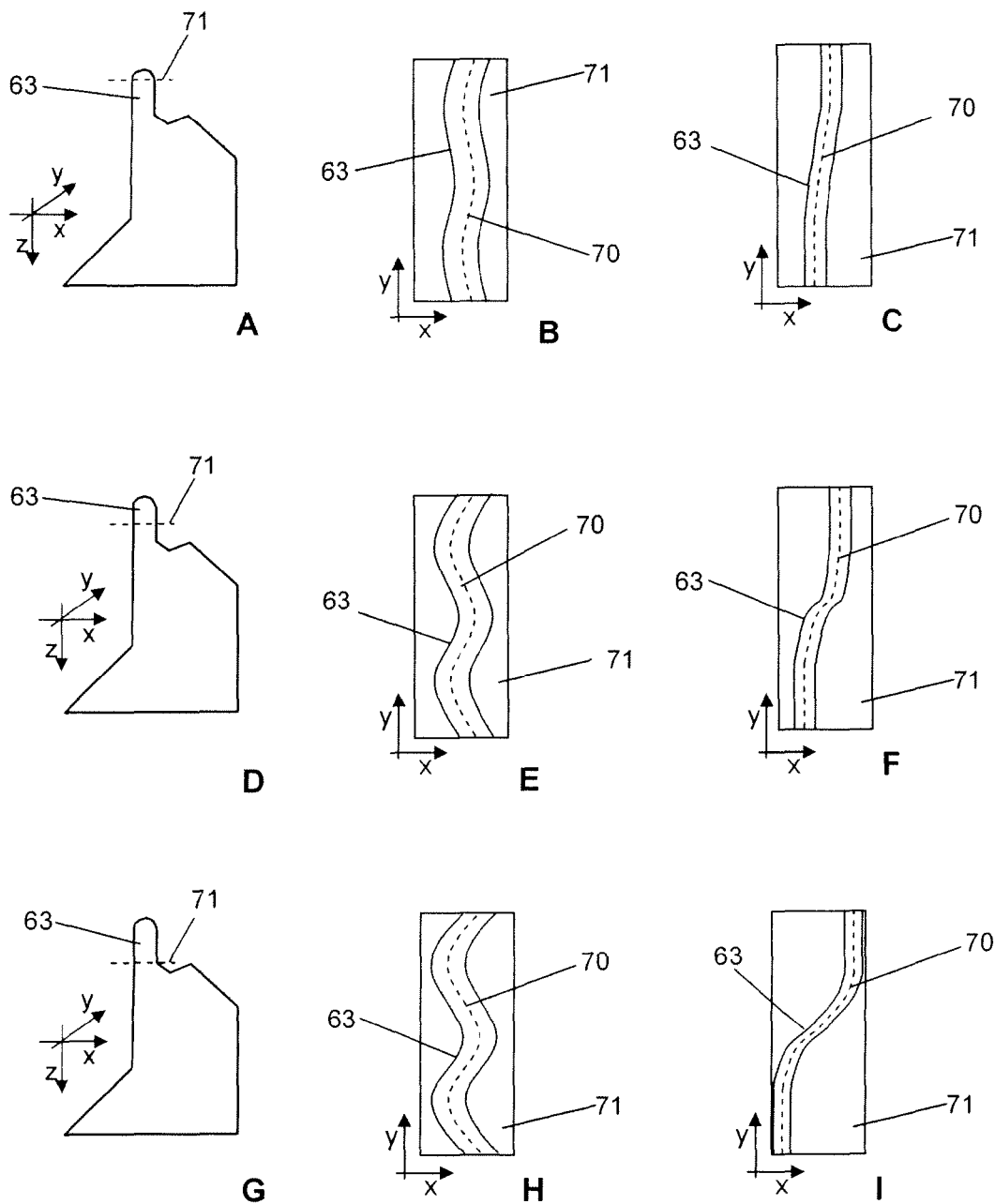

Further examples of transverse midlines of grooves 85 are given in FIGS. 15-2 and 15-3. In FIG. 15-2D, cross-sections (e.g. 80-2, 81-2, 82-2, FIG. 15-2A to 15-2C) of a tampon along the longitudinal axis (A-A') are overlaid to form a composite view of a groove 84 which provides an inverted fan shape. In FIG. 15-3D, cross-sections (e.g. 80-3, 81-3, 82-3, FIG. 15-3A to 15-3C) of a tampon along the longitudinal axis (A-A') are overlaid to form a composite view of a groove 84 which provides an inverted bucket shape.

It is noted that the differing or diverging groove paths may exclude deformities of the insertion or withdrawal end caused by pressing the tampon ends. Typically a tampon of the invention will be disposed with a shaped insertion end to facilitate digital or applicator insertion; examples of insertion ends include domed shaped, mushroom shaped, rivet shaped, or conical shape. Typically a tampon of the invention will be disposed with a shaped withdrawal end to facilitate removal of the tampon; examples of withdrawal ends include domed shaped and conical shaped. According to one aspect of the invention, the different paths are considered in the central part of the tampon i.e. excluding any deformed insertion and/or withdrawal end.

The groove may be formed from a series of x-y planes 53 running from the inner extremity of the groove towards the surface i.e. at a depth z where z is smaller towards the core 12 compared with towards the surface 12 of the tampon. For example, z may be a value close to zero (e.g. z=0 or z=0.0001) at inner extremity of a groove. Thus, the shape of the groove can be defined using an xyz co-ordinate system wherein y corresponds to a value in an axis (y-axis), z corresponds to a value in an axis (z-axis) x corresponds to a value in an axis (x-axis). According to one aspect of the invention, the path of the inner longitudinal path 5 in an x-y plane gradually changes as the value of z increases. This compares with the prior art where the path of each groove is constant in the direction of the z-axis. The path of the groove between successive x-y planes in the z-direction may change in a plurality of ways. For example, the shape (from sinusoidal to sawtooth), the amplitude of undulations (e.g. from gentle to pronounced wave), and/or inclination (e.g. from aligned with the central axis to inclined with the central axis). The change generally arises for the majority of inner longitudinal paths e.g. for a block of 55%, 60%, 70%, 80%, 90% or more consecutive inner longitudinal paths. Preferably the change gives rise to a path length in an x-y plane that decreases as the plane rises towards the surface of the tampon i.e. as z increases.

According to one embodiment of the invention, present tampon is characterized in that at least one tampon groove is defined by an outer longitudinal path 2 on the surface of the tampon and a plurality of inner longitudinal paths 5 below the surface of the tampon whereby the outer longitudinal path 2 of a groove is at least partly divergent from at least one inner longitudinal path 5. The outer longitudinal path 2 of a groove refers to the longitudinal path taken along the longitudinal axis (A-A') by the groove on the circumferential surface of the tampon (2, FIG. 3-1F, 3-2F, 4-1F, 4-2F, 5-1F, 5-2F). Typically the outer longitudinal path 2 of a groove is on the outer surface of the tampon formed where lips of a groove come together. It may be further defined as the path where the outer edges of the ribs contact each other, in between adjacent ribs. It will be appreciated that the outer edges of the ribs 3, 3' that flank a groove 4 at the surface may be not necessarily be in intimate contact with each other, and that the outer longitudinal path 2 will be the midline of the path traced by the outer edges of the flanking ribs. The outer longitudinal path is the path of a groove is visible on the exterior of the tampon. The outer longitudinal path 2 may describe any shape along the body of said tampon 1, for example, a straight, curved, undulating or non-straight line. The outer longitudinal path 2 may be parallel to the longitudinal axis (A-A') of the tampon, as depicted, for example in FIG. 3-1F where it is a straight line. Alternatively, the outer longitudinal path 2 may be inclined thereto, giving rise to tampons having inclined-grooves on the surface, as depicted, for example in FIG. 4-1F. When the outer longitudinal path 2 has a curved shape, it gives rise to tampons having curved grooves on the surface, as depicted, for example in FIGS. 7A to 7C. When the inner longitudinal path 5 is at least partly divergent from the outer longitudinal path 2 its path at least partly deviates therefrom. The divergence can be any form. For example, the inner longitudinal path 5 may be inclined to the outer longitudinal path 2. Alternatively, the inner longitudinal path 5 may adopt a wave-shaped (curved) pattern, a saw tooth pattern etc, having one, two or more points of inflection or crossing, compared to a different path of the surface of the tampon. For example, the inner longitudinal path 5 may adopt a wave-shaped (curved) pattern, a saw tooth pattern etc, having increased amplitude compared with a similar pattern on the surface of the tampon. Alternatively, the outer longitudinal path 2 may adopt a wave-shaped (curved) pattern, a saw tooth pattern etc, having one, two or more points of inflection or crossing, compared to a different inner longitudinal path 5. For example, the outer longitudinal path 2 may adopt a wave-shaped (curved) pattern, a saw tooth pattern etc, having increased amplitude compared with a similar pattern below the surface of the tampon. A divergent path may mean the inner longitudinal path 5 crosses at least once, the outer longitudinal path 2. Generally any divergence which increases the length of the inner longitudinal path 2 compared with the outer longitudinal path 5 is envisaged. Alternatively, any divergence which increases the length of the outer longitudinal path 5 compared with the inner longitudinal path 2 is envisaged.

Non-limiting drawings of tampons showing outer longitudinal paths which are aligned with the y-axis, and divergent inner longitudinal path is shown in FIGS. 16A to C, and FIGS. 17A to C. grooves. FIG. 16A shows a plan view, along the y-axis whereby the grooves 131 have been opened, and a twisting 132 of the groove is evident towards the core but is absent on the surface. FIG. 16B shows an elevation view of a tampon having opened grooves 131, in which the surface of the groove is parallel to the y-axis (or longitudinal axis A-A' of the tampon), and the inner part of the groove 132 is inclined. FIG. 16C shows a perspective view of FIG. 16B having the same features. FIG. 17A shows a plan view, along the y-axis whereby the grooves 141 have been opened, and a twisting 142 of the groove is evident towards the core but is absent on the surface. FIG. 17B shows an elevation view of a tampon having opened grooves 141, in which the surface of the groove is parallel to the y-axis (or longitudinal axis A-A' of the tampon), and the inner part of the groove 142 is curved. FIG. 17C shows a perspective view of FIG. 17B having the same features.

Inner Longitudinal Path is an Undulation

According to one aspect of the invention the inner longitudinal path 5 of a groove is undulated. The amplitude or frequency (number) of at least two inner longitudinal path 5 undulations are divergent from each other in a groove. The amplitude of the majority of inner longitudinal path 5 undulations preferably changes gradually in the direction from the core 12 to the surface 13 of the tampon. The majority is preferably a block of 55%, 60%, 70%, 80%, 90% or more consecutive inner longitudinal paths 5. As mentioned, the change is preferably gradual, though abrupt changes are also within the scope of the invention. Thus the amplitude of at least one (e.g. 2, 3 or all) undulation gradually changes as the value of z changes. The frequency of undulations may remain the same or may also change. An undulated line is a wave-like line that has a regular curvature, such as a sinusoidal curvature, or a cosinusoidal curvature. There may be one or more points of inflection where the curvature changes sign. This embodiment is exemplified in FIGS. 3-1A to 3-1F and FIGS. 3-2A to 3-2F.

FIG. 3-1A shows the position of an x-y plane 53, perpendicular to the z-axis, close to central axis of the tampon i.e. z=0.1 W, where W is the diameter of the tampon. FIG. 3-1A shows a transverse cross section 8 of a tampon across the line B-B' (FIG. 1A). One groove cross-section 9 is shown for clarity. The inner longitudinal path 5 in the x-y plane 53 of FIG. 3-1A is shown in FIG. 3-1B, which comprises an undulating line. Note the planes in FIGS. 3-1B, 3-1D and the view in 3-1F are shown as a rectangular for simplicity, however, the shape will be determined by the outer shape of the tampon which may have domed end, be mushroom shaped or adopt alternative configurations. As the value of z increases (FIGS. 3-1C and 3-1D) to z=0.3, for example, the amplitude of an undulation decreases; the inner longitudinal path 5 in FIG. 3-1D has a reduced amplitude in respect of both undulations. FIGS. 3-1B and 3-1D clearly demonstrate the aforementioned change in the inner longitudinal path 5 as the value of z increases in instant case from 0.1 W to 0.3 W. FIG. 3-1F shows the outer longitudinal path 2, visible on the surface of the tampon devoid of undulations i.e. the amplitudes of the undulations are zero. While FIG. 3-1F is a straight line, it may equally be an undulation with a smaller amplitude that the inner longitudinal path 5 when z<0.5 W e.g. when z=0.3.

FIG. 3-2A shows the position of an x-y plane 53, perpendicular to the z-axis, close to central axis of the tampon i.e. z=0.1 W, where W is the diameter of the tampon. FIG. 3-2A shows a transverse cross section 8 of a tampon across the line B-B' (FIG. 1A). One groove cross-section 9 is shown for clarity. The inner longitudinal path 5 in the x-y plane 53 of FIG. 3-2A is shown in FIG. 3-2B, which comprises a straight line devoid of undulations i.e. the amplitudes of the undulations are zero. While FIG. 3-2B is a straight line, it may equally be an undulation with a smaller amplitude than an inner longitudinal path 5 closer to the surface e.g. when z=0.3. Note the planes in FIGS. 3-2B, 3-2D and the view in 3-2F are shown as a rectangular for simplicity, however, the shape will be determined by the outer shape of the tampon which may have domed end, be mushroom shaped or adopt alternative configurations. As the value of z increases (FIGS. 3-2C and 3-2D) to z=0.3, for example, the amplitude of an undulation increases; the inner longitudinal path 5 in FIG. 3-2D has an increased amplitude in respect of both undulations. FIGS. 3-2B and 3-2D clearly demonstrate the aforementioned change in the inner longitudinal path 5 as the value of z increases in instant case from 0.1 W to 0.3 W. FIG. 3-2F shows the outer longitudinal path 2, visible on the surface of the tampon having undulation of the largest amplitude.

According to one aspect of the invention the frequency of undulations in a groove changes as the value of z changes. As the value of z increases (in the direction from the core 12 to the surface 13), the frequency of undulations may decrease. The groove visible on the surface of the tampon may be a wave with 1 undulation or may be a straight line.

Longitudinal Path is an Inclined Line

According to one aspect of the invention, the inner longitudinal path 5 of a groove is inclined. The incline of at least two inner longitudinal paths 5 are divergent from each other in a groove. The inclination of the majority of inner longitudinal paths 5 preferably changes gradually in the direction from the core 12 to the surface 13 of the tampon. The majority is preferably a block of 55%, 60%, 70%, 80%, 90% or more consecutive inner longitudinal paths 5. As mentioned, the change is preferably gradual, though abrupt changes are within the scope of the invention. The inner longitudinal line may be a straight line. Thus, as z increases, the inclination may increase or decrease as the inner longitudinal path 5 progressively aligns with the longitudinal axis of the tampon, in the direction from the core 12 to the surface 13 of the tampon; preferably it decreases. The groove visible on the surface of the tampon may be aligned with the central axis or may be inclined thereto. This embodiment is exemplified in FIGS. 4-1A to 4-1F and FIGS. 4-2A to 4-2F.

FIG. 4-1A shows the position of an x-y plane 53, perpendicular to the z-axis, close to central axis of the tampon i.e. z=0.1 W, where W is the diameter of the tampon. The inner longitudinal path 5 in the x-y plane 53 of FIG. 4-1A is shown in FIG. 4-1B, which comprises a straight line, inclined to the y-axis. Note the planes in FIGS. 4-1B, 4-1D and the view in FIG. 4-1F are shown as a rectangular for simplicity, however, the shape will be determined by the outer shape of the tampon which may have domed end, be mushroom shaped or adopt alternative configurations. As the value of z increases (FIGS. 4-1C and 4-1D) to z=0.3, for example, the angle of inclination with respect to the y-axis decreases; the inner longitudinal path 5 in FIG. 4-1D is less inclined. FIGS. 4-1B and 4-1D clearly demonstrate the aforementioned change in the inner longitudinal path 5 as the value of z increases in instant case from 0.1 W to 0.3 W. FIG. 4-1F shows the outer longitudinal path 2, visible on the surface of the tampon which is still inclined, but visibly less inclined that the inner longitudinal paths (FIGS. 4-1D and 4-1F). While FIG. 4-1F is an inclined line, it may equally be a line parallel to the central axis.

According to one embodiment, the plurality of inner longitudinal paths 5 of a groove of said tampon corresponds to an inclined line in the x-y plane, shows the function $$x = ((y \cdot a)/z) + b$$

wherein a is different from zero and is constant, b is an offset which can be constant or can change in proportion to the value of z, wherein y corresponds to a value along the y-axis, wherein x corresponds to a value along the x-axis, wherein z corresponds to a value along the z-axis.

FIG. 4-2A shows the position of an x-y plane 53, perpendicular to the z-axis, close to central axis of the tampon i.e. z=0.1 W, where W is the diameter of the tampon. The inner longitudinal path 5 in the x-y plane 53 of FIG. 4-2A is shown in FIG. 4-2B, which comprises a straight line, slightly inclined to the y-axis. Note the planes in FIGS. 4-2B, 4-2D and the view in FIG. 4-2F are shown as a rectangular for simplicity, however, the shape will be determined by the outer shape of the tampon which may have domed end, be mushroom shaped or adopt alternative configurations. As the value of z increases (FIGS. 4-2C and 4-2D) to z=0.3, for example, the angle of inclination with respect to the y-axis increases; the inner longitudinal path 5 in FIG. 4-2D is more inclined. FIGS. 4-2B and 4-2D clearly demonstrate the aforementioned change in the inner longitudinal path 5 as the value of z increases in instant case from 0.1 W to 0.3 W. FIG. 4-2F shows the outer longitudinal path 2, visible on the surface of the tampon visibly more inclined that the inner longitudinal paths (FIGS. 4-2D and 4-2F).

According to one embodiment, the plurality of inner longitudinal paths 5 of a groove of said tampon corresponds to an inclined line in the x-y plane, shows the function $$x = (y \cdot a \cdot z) + b$$

wherein a is different from zero and is constant, b is an offset which can be constant or can change in proportion to the value of z, wherein y corresponds to a value along the y-axis, wherein x corresponds to a value along the x-axis,
wherein z corresponds to a value along the z-axis.

Longitudinal Path is a Curve with Convex/Concave Parts

According to one aspect of the invention, the inner longitudinal path 5 of a groove is at least partly curved having one or more points of inflection 6 which inflection point defines a convex part and a concave part. In other words, the amplitude of at least two inner longitudinal path 5 undulations are different from each other in a groove. The majority of inner longitudinal paths 5 of a groove is at least partly curved having one or more points of inflection 6 which inflection point defines a convex part and a concave part. The curves may be, for example, asymptotic. The point of inflection is preferably with respect to the y-axis. The amplitude of the convex and/or concave parts may decrease gradually direction from the core 12 to the surface 13 of the tampon for the majority of longitudinal paths. The majority is preferably a block of 55%, 60%, 70%, 80%, 90% or more consecutive inner longitudinal paths 5. As mentioned, the change is preferably gradual, though abrupt changes are also within the scope of the invention. Thus, as z increases, the amplitude of the convex and/or concave parts may decrease as the path progressively aligns with the longitudinal axis of the tampon in a direction towards the surface of the tampon. The groove visible on the surface of the tampon may be a straight line, having no amplitude, alternatively, it may be a curve with convex/concave with an amplitude greater or smaller than the inner longitudinal path 5.

One aspect of this embodiment is exemplified in FIGS. 5-1A to 5-1F. FIG. 5-1A shows the position of an x-y plane 53, perpendicular to the z-axis, close to central axis of the tampon i.e. z=0.1 W, where W is the diameter of the tampon. The inner longitudinal path 5 in the x-y plane 53 of FIG. 5-1A is shown in FIG. 5-1B, which comprises a curved line having one point of inflection 6 through the y-axis, which inflection point defines a convex part and a concave part with respect to the y-axis. Note the planes in FIGS. 5-1B, 5-1D and the view in 5-1F are shown as a rectangular for simplicity, however, the shape will be determined by the outer shape of the tampon which may have domed end, be mushroom shaped or adopt alternative configurations. As the value of z increases (FIGS. 5-1C and 5-1D) to z=0.3, for example, the amplitude 56 of both concave and convex parts (with respect to the y-axis) decreases; the inner longitudinal path 5 in FIG. 5-1D shows a reduced amplitude in respect of both convex and concave parts. FIGS. 5-1B and 5-1D clearly demonstrate the aforementioned change in the inner longitudinal path 5 as the value of z increases in instant case from 0.1 W to 0.3 W. FIG. 5-1F shows the outer longitudinal path 2, visible on the surface of the tampon which is a straight line, and aligned with the longitudinal axis of the tampon. While FIG. 5-1F is a straight line, it may equally be a curved with a smaller amplitude that the inner longitudinal path 5 when z<0.5 W e.g. when z=0.3.

Another aspect of this embodiment is exemplified in FIGS. 5-2A to 5-2F. FIG. 5-2A shows the position of an x-y plane 53, perpendicular to the z-axis, close to central axis of the tampon i.e. z=0.1 W, where W is the diameter of the tampon. The inner longitudinal path 5 in the x-y plane 53 of FIG. 5-2A is shown in FIG. 5-2B, which is a straight line aligned with the longitudinal axis of the tampon. While it is shown as a straight line, it may equally be a curved line with a smaller amplitude that the inner longitudinal path 5 when z>0.1 W e.g. when z=0.3. Note the planes in FIGS. 5-2B, 5-2D and the view in 5-2F are shown as a rectangular for simplicity, however, the shape will be determined by the outer shape of the tampon which may have domed end, be mushroom shaped or adopt alternative configurations. As the value of z increases (FIGS. 5-2C and 5-2D) to z=0.3, for example, the amplitude 56 of both concave and convex parts (with respect to the y-axis) increases; the inner longitudinal path 5 in FIG. 5-2D shows an increased amplitude in respect of both convex and concave parts. FIGS. 5-2B and 5-2D clearly demonstrate the aforementioned change in the inner longitudinal path 5 as the value of z increases in instant case from 0.1 W to 0.3 W. FIG. 5-2F shows the outer longitudinal path 2, visible on the surface of the tampon which is the aforementioned curved line having a greater amplitude that the inner longitudinal path 5 when z<0.5 W e.g. when z=0.3.

The term "point of inflection" 6 refers to the point on a curve where the curvature of the curve changes; and in particular to a point where the curve changes from a convex to a concave curve or to a convex part of a curve to a concave part of a curve, or vice versa. Such point is in particular characterized in that the second derivative thereof is zero.

As used herein, the term "convex part", refers to a part of a curve that curves or bulges outward. The convex part may be open or closed. An "open convex part" refers to a curve which does not include a point wherein the first derivative is zero. A point wherein the first derivative is zero corresponds to a maximum or a minimum in the curve. In this case the convex part of the curve may approach an asymptote which is parallel to the y-axis, and the maximum or minimum may be present at infinity. A "closed convex part" refers to a curve which includes only one point wherein the first derivative is zero.

As used herein, the term "concave part", refers to a part of a curve that curves inward. The concave part may be open or closed. An "open concave part" refers to a curve which does not include a point wherein the first derivative is zero. A point wherein the first derivative is zero corresponds to a maximum or a minimum in the curve. In this case the concave part of the curve may approach an asymptote which is parallel to the inner longitudinal line 7, and the maximum or minimum may be present at infinity. A "closed concave part" refers to a curve which includes only one point wherein the first derivative is zero.

In one embodiment, the plurality of inner longitudinal paths 5 of a groove of said tampon corresponds to a curved line in the x-y plane, showing the function $$x=((a \cdot y^{-m})/z)+b$$

wherein m is an odd positive whole number which is different from 1,
wherein a is a constant, different from zero, b is an offset which can be constant or can change in proportion to the value of z,
wherein y corresponds to a value along the y-axis,
wherein x corresponds to a value along the x-axis,
wherein z corresponds to a value along the z-axis.

In another embodiment, the plurality of inner longitudinal paths 5 of a groove of said tampon corresponds to a curved line in the x-y plane, showing the function $$x = z \cdot a \cdot y^{-m} + b$$

wherein m is an odd positive whole number which is different from 1,
wherein a is a constant, different from zero, b is an offset which can be constant or can change in proportion to the value of z,
wherein y corresponds to a value along the y-axis,
wherein x corresponds to a value along the x-axis,
wherein z corresponds to a value along the z-axis.

The above-referred function is a power function wherein x, y and z are the variables that are to be related, parameters a and m describe the relationship. The parameter a increases the amplitude of the curve i.e. moves the values for x, up or down as an increase or decrease, respectively. The parameter b is an offset which can displace the curve along the x-axis. It can be constant or can change with the value of z. The parameter m, determines the function's rates of growth or decay. Preferably the parameter m is a positive and odd whole number, different from zero and one and for instance 3, 5, 7, 9, etc. the parameter a is different from zero and may for instance be −6, −5, −4, −3, −2, −1, 1, 2, 3, 4, 5, 6, etc. The longitudinal grooves and/or ribs preferably extend over at least 25° to 80° of the tampons' circumference, and preferably over 30 to 45° of the tampons' circumference.

In a preferred embodiment, the plurality of inner longitudinal paths 5 of a groove correspond to a curved line whereby the value of m=3.

In alternative preferred embodiment, the inner longitudinal path 5 of a groove follows the path of a continuous hyperbolic function or to a continuous inverse hyperbolic. The term "continuous" as used herein refers to a curve or function, which extends without break or irregularity.

In a preferred embodiment, the hyperbolic function corresponds to any of the following hyperbolic functions $y=z(\sin h(x))/a$; $y=\sin h(x)/za$; $y=z(\tan h(x))/a$ or $y=\tan h(x)/za$. The functions $y=z\cdot(\sin h(x))/a$ and $y=\sin h(x)/za$ correspond to a hyperbolic sine of x (see FIG. 8A), and can also be written as $y=z\cdot(\sin h(x))/a=z\cdot(e^x-e^{-x})/2a$ or $y=(\sin h(x))/za=(e^x-e^{-x})/2za$ respectively. The functions $y=z\cdot(\tan h(x))/a$ $y=(\tan h(x))/za$ correspond to a hyperbolic tangent of x (see FIG. 8B), and can also be written as $y=z\cdot\sin h(x)/a\cdot\cos h(x)$ or $y=\sin h(x)/z\cdot a\cdot\cos h(x)$ respectively whereby $\sin h(x)$ is $(e^x-e^{-x})/2$ and $\cos h(x)$ is $(e^x+e^{-x})/2$.

In a particularly preferred embodiment, the inverse hyperbolic function corresponds to the function $y=z\cdot(\text{artan } h(x))/a$ or $y=(\text{artan } h(x))/z\cdot a$, wherein y corresponds to a value in an axis along the inner longitudinal line 5, and wherein x corresponds to a value in an axis perpendicular to the inner longitudinal line 5. The functions $y=z\cdot(\text{artan } h(x))/a$ and $y=(\text{artan } h(x))/z\cdot a$ corresponds to inverse hyperbolic tangent of x (see FIG. 8C).

The values for x and y in the above-indicated power or hyperbolic function may be as follows: x may be a value that is comprised between $+\frac{1}{2}W$ and $-\frac{1}{2}W$ and y may be a value that is comprised between $+\frac{1}{2}L$ and $-\frac{1}{2}L$, z may be a value that is comprised between $+\frac{1}{2}W$ and $-\frac{1}{2}W$.

Single Inflection Point for Inner Longitudinal Path

According to one embodiment of the invention, the inner longitudinal path 5 of a groove below the surface of the tampon has only one point of inflection 6, which inflection point defines one convex part and one concave part with respect to the longitudinal groove axis 7.

In a preferred embodiment, said point of inflection is substantially located in the middle part of the tampon longitudinal body. Preferably point of inflection is located in a region covering the middle 50% of the tampon longitudinal body area. Even more preferred, this point of inflection is located about an imaginary line known as the longitudinal groove axis 7. It is noted that it is of utmost importance in the present tampon configuration that only one point of inflection is provided in the path of the tampon grooves. Because there is only one point of inflection, the path of the grooves will undergo only one change in direction. As a consequence thereof, friction between the tampon grooves and the pressing apparatus can be considerably minimized.

In a preferred embodiment, the tampon is characterised in that the inner longitudinal path 5 corresponds to a continuous curved line, which is point symmetric in relation to said point of inflection.

In a particularly preferred embodiment, the tampon is characterised in that the inner longitudinal path 5 corresponds to a continuous curved line which does not show a point having a first derivative equal to zero. In other words, the curve describing path of inner longitudinal path 5 along the longitudinal groove axis 7 does not show a minimum and/or maximum.

The inner longitudinal path 5 corresponds to a continuous curved line, which preferably does not show any points wherein a first derivative is equal to zero. However, in an alternative embodiment, the inner longitudinal path 5 may correspond to a curved line showing one or two points which have a first derivative equal to zero. A first such point may be located in the top 25% of the tampon longitudinal body length, and for instance be located in the insertion end of the tampon. A second such point may be located in the bottom 25% of the tampon longitudinal body length, and for instance be located in the withdrawal end on the tampon. In an embodiment, a tampon is provided, wherein said curved line shows only one point which has a first derivative equal to zero, whereby a first point is located in the top 25% or the bottom 25% of the tampon longitudinal body length. In another embodiment, a tampon is provided tampon wherein said curved line shows maximally two points which has a first derivative equal to zero, whereby a first point is located in the top 25% and a second point is located in an the bottom 25% of the tampon longitudinal body length. In yet another embodiment, a tampon is provided wherein said point wherein the first derivative equal to zero is located at the top of the tampon, i.e. at $-\frac{1}{2}L$, and/or at the bottom of the tampon, i.e. at $+\frac{1}{2}L$.

FIG. 7 shows embodiments of a tampon according to the invention having curved outer longitudinal paths. In FIGS. 7A, 7B and 7C, tampons respectively having 4, 6 and 8 longitudinal grooves are represented. In accordance with the present invention the path of the grooves and ribs in the longitudinal direction of the tampon body between insertion and withdrawal part may go from convex to concave as shown in tampon representations in the left handed FIG. 7 A-C or from concave to convex, as shown in the right handed FIG. 7 A-C. It is however important to notice that each curve of the grooves in the represented tampon embodiments shows only one inflection point, and thus only one convex part and only one concave part. In FIG. 7 the curved grooves below the surface, having only one point of inflection. The curved line defining the path of the tampon grooves does not show any maximum or minimum point wherein the first derivative would be zero. In the event that such point would be present, it may be located in the top and/or the bottom compressed area of the tampon. From FIG. 7, it is clear that the path of the tampon grooves and ribs does not follow a periodic curve, and does not correspond to a wave function, since there is no cyclic returning pattern in the curve.

Parallel or Inclined Outer Longitudinal Path

According to one non-limiting aspect of the invention, the outer longitudinal path 2 describes a straight line along the body of said tampon 1 as shown, for example, in FIGS. 1, 3F, 4F and 5F.

According to one aspect of the invention, the outer longitudinal path 2 is parallel to the longitudinal axis of the tampon, giving rise to tampons with a non-inclined groove appearance. In other words, the outer longitudinal path 2 is parallel to the longitudinal axis (A-A') of the tampon (FIGS. 9A, 9B). According to one aspect of the invention, when the tampon is viewed end on (i.e. along the A-A' axis, or along arrow 33 in FIG. 9B), the distal (e.g. insertion) 32 and proximal (e.g. withdrawal) 31 end points of the outer longitudinal path 2 coincide; this arises in the case of a non-inclined surface groove, as shown in FIGS. 9A and 9B. It is noted that the terms proximal end 31 and distal ends 32 are used throughout the application to distinguish arbitrarily one end of the tampon from the other. The proximal end may refer to the withdrawal end and the distal end may refer to the insertion end or vice versa. In the present description, and for clarity only, the proximal end and the distal end typically refers to the withdrawal and insertion ends respectively.

According to another aspect of the invention, the outer longitudinal path 2 of a groove may be inclined (FIGS. 10A, 10B), to the longitudinal axis (A-A') of the tampon, so producing tampons with an inclined groove appearance.

As shown in FIG. 10B, the angle of inclination can be defined according to the angle, alpha, adopted between the outer longitudinal path 2 and the longitudinal axis A-A' when viewed through the tampon. The longitudinal axis A-A' crosses the outer longitudinal path 2 in question, so creating the angle alpha.

The value of alpha can be greater or smaller than zero, plus or minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43, 44, 45, 46, 47, 48, 49, 50, 55, 60, 65, 70, 75, 80, 85, 89, 90 deg, or a value in the range between any two of the aforementioned values, preferably 10 to 50 deg, 20 to 40 deg, 25 to 30, 10 to 20 deg, more preferably 5 to 25 deg, and most preferably 12 to 15, deg. It may be −10 to −50 deg, −20 to −40 deg, −25 to −30, −10 to −20 deg, more preferably −5 to −25 deg, and most preferably −12 to −15, deg. In the preferred range, the production process is improved in the compression and the ejection of the pressed product.

According to another aspect of the invention, when the tampon is viewed end on (i.e. along the A-A' axis, or along arrow 33 in FIG. 10B), the distal (insertion) 32 and proximal (withdrawal) 31 end points of the outer longitudinal path 2 do not coincide; this arises in the case of an inclined surface groove, as shown in FIG. 10A. The angle of inclination, defined as a torsion angle, beta, when viewed along the A-A' axis, can be greater or smaller than zero, plus or minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43, 44, 45, 46, 47, 48, 49, 50, 55, 60, 65, 70, 75, 80, 85, 89, 90 deg, or a value in the range between any two of the aforementioned values, preferably 10 to 50 deg, more preferably 20 to 40, and most preferably 25 to 30 deg. It may be −10 to −50 deg, more preferably −20 to −40, and most preferably −25 to −30 deg. In the preferred range, the production process is improved in the compression and the ejection of the pressed product.

According to the invention, and illustrated in the various figures, the outer longitudinal path is not limited to a straight line, but may adopt any path including, for example, undulating or curved.

As further indicated below, the insertion end of the tampon may have undergone some deformation in order to have a dome shape or the like. It will be understood from the present invention that the above-indicated distal end may be integrated into the dome-like deformation of the insertion end. Likewise, as further indicated below, the withdrawal end of the tampon may also have undergone some deformation, e.g. in order to have a constricted shape. It will be understood from the present invention that also in such case the above-indicated proximal end may be integrated into the deformation of the withdrawal end.

Displacement of Inner Longitudinal Path

According to one aspect of the invention the majority of inner longitudinal paths 5, show displacement perpendicular to the longitudinal (A-A') axis, gradually in the direction from the core 12 to the surface 13 of the tampon. The majority is preferably a block of 55%, 60%, 70%, 80%, 90% or more consecutive inner longitudinal paths 5. Thus the inner longitudinal path 5 in an x-y plane may not only changes shape as z changes, but may be gradually displaced in the direction of the x-axis as z changes. As z increases, the displacement from the original position may gradually increase as the inner longitudinal path 5 rises towards the surface of the tampon. The effect of the displacement is a tampon which, when viewed in transverse cross-section, shows a groove that is divergent from the radius. This embodiment is exemplified in FIG. 11 which is a schematic illustration of a transverse (B-B') cross-section of a tampon according to the present invention. It can be seen from FIG. 11 that the transverse path 111 of a groove 9 does not coincide with the radius of the groove 112, but diverges therefrom. The transverse path of a groove is the path seen in transverse cross section (through B-B').

The "radius of the groove" 112, as used herein, refers to straight radial line 112 that starts at the midpoint 115 of a transverse (B-B') cross-section of the tampon, and runs towards its circumference through the outermost (surface) point 114 of the closed groove. The radius of a groove is illustrated in FIG. 11 as line 112.

According to one embodiment of the invention, the transverse path 111 of a groove is positioned at a minimum angle (delta) of 1, 2, 3, 4, 5, 6, 7, 8, 9, 10, 11, 12, 13, 14, 15, 16, 17, 18, 19 or 20 deg and a maximum angle of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 deg vis à vis the radius of the groove 112, or at angle in the range between any two of the aforementioned values. According to one embodiment of the invention, the transverse path 111 of a groove is positioned at a minimum angle of −1, −2, −3, −4, −5, −6, −7, −8, −9, −10, −11, −12, −13, −14, −15, −16, −17, −18, −19 or −20 deg and a maximum angle of −30, −31, −32, −33, −34, −35, −36, −37, −38, −39, −40, −41, −42, −43, −44, −45, −46, −47, −48, −49, −50, −51, −52, −53, −54, −55, −56, −57, −58, −59 or −60 deg vis à vis the radius of the groove 112 or at angle in the range between any two of the aforementioned values.

According to another embodiment of the invention, the transverse path 111 of a groove is positioned essentially at an angle (delta) between 1 deg and 60 deg (or −1 deg and −60 deg) vis à vis the radius of the groove 112, preferably at an angle between 1 deg and 30 deg (or −1 deg and −30 deg) and more preferably at an angle between 10 deg and 20 deg (or −10 deg and −20 deg).

Complete or Incomplete Inner Longitudinal Path

According to one aspect of the invention, the inner longitudinal path 5 in an x-y plane is a line that remains complete as z changes. By complete, it is meant that the inner longitudinal path 5 in an x-y plane extends from a distal (e.g. withdrawal) end to the proximal (e.g. insertion) end of the tampon without interruption or truncation as z changes. The inner longitudinal path 5 as a complete line is present in x-y planes below the surface of the tampon, towards the core, and essentially disappears at the centre of the tampon core in a complete manner. This embodiment is exemplified in 3-1B, 3-1D, 3-2B, 3-2D, 4-1B, 4-1D, 4-2B, 4-2D, 5-1B, 5-1D, 5-2B, 5-2D where each of the inner longitudinal paths 5 are complete lines.

According to another aspect of the invention, the inner longitudinal paths 5 towards the core of the tampon (i.e.

within a radius of 0.1 W, 0.2 W, 0.3 W, 0.4 W) are incomplete. By incomplete, it is meant that the inner longitudinal path 5 extending from the distal end (e.g. insertion) to the proximal (e.g. withdrawal) end of the tampon is interrupted or truncated. The extent of the incomplete parts may greater for inner longitudinal paths 5 closer to the core 12 than at the surface 13. Thus, the inner longitudinal path 5 in an x-y plane changes gradually or abruptly from a complete line to an incomplete line as z changes. The inner longitudinal path 5 may extend from the distal end to the proximal end of the tampon in an x-y plane along the z-axis without interruption or truncation, but becomes interrupted or truncated in another x-y plane as z changes. The inner longitudinal path 5 as a complete line is generally present from below the surface of the tampon, but becomes incomplete towards the core and essentially disappears at the core of the tampon altogether. The incomplete path arises as the value of z decreases i.e. more incomplete path towards the core of the tampon. An incomplete inner longitudinal path 5 is a result of a variation in the impression depth along the longitudinal axis by the pressing apparatus (see below).

u-Shaped Impression Profile

According to one aspect of the invention, the inner longitudinal path 5 becomes incomplete towards the tampon core 12, so as to give a u-shaped impression profile. The u-shape is evident when the groove is viewed as a y-z projection, and the groove is uppermost as depicted in FIGS. 12A to 12H. Importantly, this reflected by an inner longitudinal path which is incomplete at or towards the proximal (e.g. withdrawal) and distal (e.g. insertion) end of the tampon towards the core 12 of the tampon. Preferably the transition from complete to incomplete lines is gradual. This embodiment is exemplified in FIGS. 12A to 12H. Note the planes in FIGS. 12C and 12F and the views in FIGS. 12B, 12E and 12H are shown as a rectangular for simplicity, however, the shape will be determined by the outer shape of the tampon which may have domed end, be mushroom shaped or adopt alternative configurations; it is noted that deformities owing to the ends of the tampons may be excluded when comparing paths. FIG. 12A shows the position of an X-Y plane 53, perpendicular to the z-axis, close to central axis of the tampon i.e. z=0.1 W, where W is the diameter of the tampon. The shape of the tampon groove as viewed through the tampon 121 is shown in FIG. 12B, whereby the inner longitudinal path 122 in a y-z projection 121' indicates a u-shaped impression profile. The inner longitudinal path 5 in the x-y plane 53 of FIGS. 12A and B is shown in FIG. 12C, which comprises an undulating line, which is incomplete, being truncated 61 at the proximal end, and truncated 60 at the distal end as indicated by dashed lines. As the value of z increases (FIG. 12D to 12F) to z=0.3, for example, the extent of truncation is reduced and the line gradually becomes more complete; the inner longitudinal path 5 in FIG. 12F shows less truncation 61 at the proximal end, and less truncation 60' at the distal end. FIGS. 12C and 12F clearly demonstrate the aforementioned change in the inner longitudinal path 5 as the value of z decreases in instant case from 0.1 W to 0.3 W. FIG. 12H shows the outer longitudinal path 2, visible 57, 57' on the surface of the tampon which is complete. It is noted that the path also changes as z-changes in accordance to the invention i.e. the amplitude of the undulations decrease as z increases.

n-Shaped Impression Profile

Figure 13F:
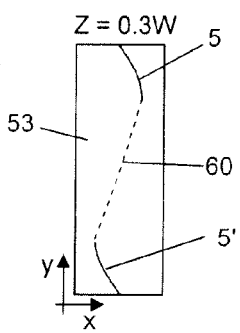
Figure 13G:
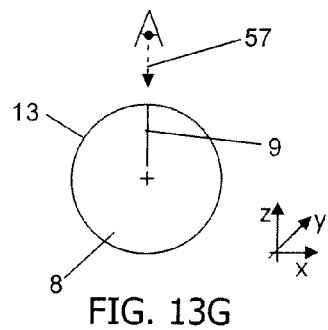
Figure 13H:
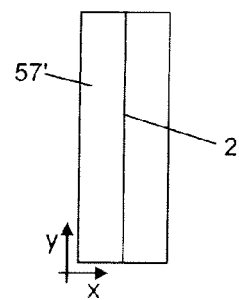

According to one aspect of the invention, the path becomes incomplete towards the core, so as to give an n-shaped impression profile for a groove. The n-shape is evident when the groove is viewed as a y-z projection, and the groove is uppermost as depicted in FIGS. 13A to 13H. This reflected by an inner longitudinal path towards the core 12, which is complete at or towards the proximal (e.g. withdrawal) and distal (e.g. insertion) ends, but incomplete in the central part, giving rise to a barrel-shaped tampon upon expansion. Preferably the transition from complete to incomplete lines is gradual. This embodiment is exemplified in FIGS. 13A to 13H. Note the planes in FIGS. 13C and 13F and the views in FIGS. 13B, 13E and 13H are shown as rectangular for simplicity, however, the shape will be determined by the outer shape of the tampon which may have domed end, be mushroom shaped or adopt alternative configurations; it is noted that deformities owing to the ends of the tampons may be excluded when comparing paths. FIG. 13A shows the position of an X-Y plane 53, perpendicular to the z-axis, close to central axis of the tampon i.e. z=0.1 W, where W is the diameter of the tampon. The shape of the tampon groove as viewed through the tampon 121 is shown in FIG. 13B, whereby the inner longitudinal path 122 in a y-z projection 121' indicates an n-shaped impression profile. The inner longitudinal path 5, 5' in the x-y plane 53 of FIGS. 13A and B is shown in FIG. 13C, which comprises a which comprises an undulating line, which is incomplete, being truncated 60 in the central portion as indicated by a dashed line. As the value of z increases (FIG. 13D to 13F) to z=0.3, for example, the extent of truncation is reduced and the line gradually becomes more complete; the inner longitudinal path 5, 5' in FIG. 13F shows less truncation 60 in the central portion. FIGS. 13C and 13F clearly demonstrate the aforementioned change in the inner longitudinal path 5, 5' as the value of z decreases in instant case from 0.1 W to 0.3 W. FIG. 13H shows the outer longitudinal path 2, visible 57, 57' on the surface of the tampon which is complete. It is noted that the path also changes as z-changes in accordance to the invention i.e. the amplitude of the undulations decrease as z increases.

Undulating Impression Profile

According to one aspect of the invention, the path becomes incomplete towards the core, so as to give an undulating impression profile for a groove. This reflected by an inner longitudinal path towards the core 12, which is has incomplete sections at regularly intervals, which incomplete sections increase in size towards the core. The change of size may follow a sinusoidal or cosinusoidal function.

This embodiment is exemplified in FIGS. 14A to 14H. Note the planes in FIGS. 14C and 14F and the views in FIGS. 14B, 14E and 14H are shown as a rectangular for simplicity, however, the shape will be determined by the outer shape of the tampon which may have domed end, be mushroom shaped or adopt alternative configurations; it is noted that deformities owing to the ends of the tampons may be excluded when comparing paths. FIG. 14A shows the position of an X-Y plane 53, perpendicular to the z-axis, close to central axis of the tampon i.e. z=0.1 W, where W is the diameter of the tampon. The shape of the tampon groove as viewed through the tampon 121 is shown in FIG. 13B, whereby the inner longitudinal path 122 in a y-z projection 121' indicates an undulating impression profile. The inner longitudinal path 5, 5', 5", 5''' in the x-y plane 53 of FIGS. 14A and B is shown in FIG. 14C, which comprises which comprises an undulating line, which is incomplete, being truncated in several positions 60, 60', 60" corresponding to undulating impression depth as indicated by a dashed line. As the value of z increases (FIG. 14D to 14F) to z=0.3, for example, the extent of truncation is reduced and the line gradually becomes more complete; the inner longitudinal path 5, 5', 5", 5''' in FIG. 14F shows less truncation 60 in the central portion. FIGS. 14C and 14F clearly demonstrate the aforementioned change in the inner longitudinal path 5, 5', 5", 5''' as the value of z decreases in instant case from 0.1 W to 0.3 W. FIG. 14H shows the outer longitudinal path 2, visible 57, 57' on the surface of the tampon which is complete. It is noted that the path also changes as z-changes in accordance to the invention i.e. the amplitude of the undulations decrease as z increases.

Curved Impression Profile

According to one aspect of the invention, the path becomes incomplete towards the core, so as to give a curved impression profile for a groove, which curve has a single point of inflection. This reflected by an inner longitudinal path towards the core 12 which is half-complete and half incomplete, and which incomplete sections increase in size towards the core. The change of size may follow a curved profile having one point of inflection described above.

Material of the Tampon

Absorbent fibrous material usable in the tampon according to the invention may consist of any absorbent material having acceptable absorbency and modulus of elasticity properties that is capable of absorbing and/or retaining liquid. The absorbent structure can be manufactured in a wide variety of sizes and shapes and from a wide variety of liquid-absorbing materials. It is, of course, desirable to use absorbent materials having a minimum content of extraneous soluble materials since the product may be retained in the body for a considerable period of time, i.e. absorbent materials contain no/little unnecessary soluble matter which could dissolve and enter the body. Retained soluble extraneous materials could cause a safety hazard if they are toxic, irritant, or sensitive. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibres; synthetic materials, such as polyester fibres, polyolefin fibres, absorbent foams, e.g. a flexible resilient polyurethane foam, absorbent sponges, super-absorbent polymers, absorbent gelling materials; formed fibres, such as capillary channel fibres and multi limbed fibres; synthetic fibres, or any equivalent material or combinations of materials, or mixtures of these.

Furthermore, the present invention relates to tampons, which can be applied digitally, i.e. without application device, as well as to tampons that can be applied with an applicator. An applicator used to position the tampon within the vagina can be any applicator known to those skilled in the art, e.g. the telescoping tube type applicator. The applicator can be made of any of the acceptable materials, e.g. cardboard or molded polyethylene. The applicator can be sized similarly to those presently commercially used.

The number of longitudinal ribs can vary, for example depending on the diameter of the tampon and/or the type of absorption material. The number of ribs may be 3, 4, 5, 6, 7, 8, 9, 10, 11 12 or more. Preferably, there are between 3 and 12 ribs, more preferably there are between 6 and 12 ribs and even more preferably, at least about 8. While the present invention, like many known tampons, may have an even number of ribs, it is also within the scope of the present invention to produce tampons with an odd number of ribs. Preferably, before use, the ribs fit closely together near the circumferential surface, providing an essentially cylindrical, smooth and soft surface. This facilitates handling of the tampon and makes insertion of the tampon more comfortable.

In an embodiment, the invention provides a tampon, wherein said tampon is at least partially surrounded by a covering. The covering is preferably not provided over the insertion end, in order to provide better access of the menses to the insertion end of the tampon. In order to improve the absorbing capacity and expansion capacity of the tampon, said covering is preferably a stretchable and/or elastic liquid-permeable covering. The covering can consist of, for example, a non woven covering material made of, for example, thermoplastic, heat sealing fibers or a plastic film. In another embodiment, the cover may also comprise a friction-lowering layer. Such a covering improves the comfort of introduction and prevents fibers from being detached during introduction or removal of the tampon into or from the body cavity.

A further preferred feature of the tampon of the invention is a withdrawal cord, extending from the withdrawal end of the tampon, in order to ease withdrawal of the tampon.

Also, the tampon is preferably provided with a round domed insertion end of high compression. This will make insertion of the tampon easier because the narrowed end goes deepest in the vagina. According to one aspect of the invention, the tampon is mushroom shaped.

A tampon may further be provided with a constricted withdrawal end. A "constricted withdrawal end", as used herein, refers to a withdrawal end which has a cross sectional diameter which is smaller than the cross-sectional diameter of the remaining tampon body. In a preferred embodiment, the invention provides a tampon, wherein said withdrawal end is a conical withdrawal end. The conical shape is one which is preferably truncated from its point. Such conical end guides the tampon during withdrawal, so making withdrawal easier. In another preferred embodiment, the invention provides a tampon, wherein said withdrawal end is a dome-shaped withdrawal end. In yet another embodiment the tampon according to the invention has a frusto-conical shape which considerably facilitates withdrawal of the tampon, especially when the tampon is not saturated.

In a further preferred embodiment, the withdrawal end is provided with a finger recess according to any technique known in the art. This facilitates the handling and the insertion of the tampon. The finger recess may be located at the withdrawal end.

The present tampons have a new configuration of groove, that is a departure from the tampons known in the art that provide a uniform groove profile from the surface of the tampon towards the innermost point of the groove. The present configuration gives the present tampon several important advantages. The tampon so produced provides grooves on the exterior surface, giving rise to a smooth feel and more comfortable wearing. The side flanks of adjacent longitudinal ribs touch one another to form a soft, closed circumferential surface of the tampon. This circumferential surface of the tampon allows a gentler and therefore more pleasant introduction into and withdrawal from the body cavity.

Because the path of the groove is different below the surface compared with on the surface, the length of the groove towards the centre of the core can be increased without increasing the depth of the grooves. Thus, grooves are substantially longer than those having no variance at a given septh. Longer grooves of the present tampons substantially improve the tampons' absorptive capacity by making available more surface area for absorption, while maintaining a more comfortable insertion and wearing. The internal groove configuration of the present tampon thus gives substantially more expansion and absorption capacity to the tampon, compared to tampons having uniform groove paths.

While the outer part of the tampon is disposed with groove of a certain length, which grooves are generally, but not limited to straight lines, the shape of the groove changes towards the core, giving grooves substantially longer than those seen in conventional tampons which have a uniform profile. Longer grooves of the present tampons substantially improve the tampons' total absorptive capacity, specific absorption and absorption rate by making available more surface area for absorption, while maintaining a more comfortable insertion and wearing. The internal groove configuration of the present tampon thus gives substantially more expansion and absorption capacity to the tampon, compared to tampons having uniform groove paths.

This is the case even for inclined groove shaped tampons, without any negative manufacturing effects. The effect can be modulated (i.e. increased or reduced) according to the extent by which the inner longitudinal path changes in the direction from the core to the surface of the tampon.

It has also been found that the tampons having an undulating or curved grooves can be ejected more quickly from a press during the manufacture of the tampon. The configuration enables effective withdrawal of finished tampons out of a pressing apparatus without harming or at least partly destroying the grooves and ribs formed in the tampon. During withdrawal of the tampon out of the press, frictional contact between the grooves of the tampon and the penetrating segments can be considerably reduced since the curvature of inner longitudinal path reduces when comparing the core with the surface of the tampon or vice versa.

Besides showing greater absorption, the tampons having grooves following the herein defined paths show greater expansion prior to saturation and show increased expansion and absorption speed. The grooves of the tampons following the herein defined paths are longer than straight-shaped or inclined-shaped grooves, and provide greater absorption. Furthermore, in the described configuration, the fibrous material which essentially determines the capacity of the tampon for absorbing the body fluid is better exploited. The present tampon provides good stretching (expansion) properties and sealing behavior, since during expansion the ribs and grooves of present tampon are capable of better fitting the shape and contours of the body cavity. The tampon advantageous requires less tampon material to achieve the same absorption and, being of smaller size, can be ejected more easily from the press. Therefore, they are easier to manufacture.

In addition, grooves following the herein defined curved path permit a purposeful enlargement of the effective product surface. The grooves following the herein defined paths enlarge the surface of the tampon and provide longer distances for the body fluid to traverse before leakage around the tampon occurs. This improvement can results from any depth of groove. However, it is preferred that the groove has a depth of at least about 1 mm, and preferably of more than about 3 mm, preferably about 3 mm to about 6 mm.

Markings

A tampon of the invention may optionally be provided with one or more markings on the surface. A marking may be provided by any mean means including printed using inks, or by impression. A marking may comprise any features including alpha numerals, graphic illustrations, patterns and/or photographic illustration. A marking may be, for example, information such as expiry date, absorbent capacity, use instruction, warning indications. Where a tampon is provided with information, it is an information carrier. A marking may also be advertising. A marking may provide product appeal to the user or groups of users. For example, it may comprise one or more images, patterns, graphics or alpha numerals designed to appeal s by way of aesthetic appearance and/or life-style association (e.g. cartoons, logos etc.).

A tampon of the invention may optionally be provided in one or more colors. Colors may be printed as mentioned above, or impregnated into the material. A color may indicate an expiry date, an absorbent capacity, a size or other information regarding the product. A color may be designed to appeal to a mind set of a user group by way of aesthetic appearance and/or life-style association.

It is a further aspect of the invention that a tampon is provided with a chemical, biochemical or biological indicator that is capable of indicative color change. Such indicator may show, for example, a medical condition. The chemical indicator may react within one or more agents in bodily fluids to indicate an abnormality. For example, a chemical indicator may change colour when a subject is suffering from a disease such as anaemia (by detecting iron/haemoglobin density), diabetes (by detecting glucose) or from the presence of sexually transmitted diseases (by detecting antigens towards for example, gonorrhea, syphilis, hepatitis A, B or C, herpes, HIV, chlamydia) etc. . . . . The indicator may also change color in accordance with the period in the menstrual cycle (by detecting hormones).

It is a further aspect of the invention that a tampon is provided with one or more perfume scents. The scent gives a pleasant odour upon handling a tampon or opening a tampon package. The scent may be an aromatherapy scent, linked with a mood such as lavender (relaxing), citrus (uplifting, fresh) or jasmine (romantic) which may provide a more emotional association with the tampon.

The invention further concerns a method for manufacturing the tampon of the invention. A strip of absorbent material having acceptable absorbency and modulus of elasticity properties that is capable of absorbing and/or retaining liquid, is wound up on itself to form an essentially cylindrical tampon blank.

In a preferred embodiment, the essentially cylindrical blank is at least partially surrounded by a covering. The covering is preferably not provided at the portion which will form the insertion end of the tampon. In order to improve the absorbing capacity and expansion capacity of the tampon, said covering is preferably a stretchable and/or elastic liquid-permeable covering.

The tampon can be provided with a withdrawal cord, according to any technique known in the art.

Press

The invention also concerns an apparatus for manufacturing the tampon of the invention. One embodiment of the invention is a press suitable for the manufacture of a tampon of the invention. Another embodiment of the invention is a press jaw suitable for the manufacture of a tampon of the invention.

In the prior art, pressing machines have penetrating segments, which form ribs defined by grooves and which penetrate the absorbing material in essentially a radial direction, i.e. in a direction leading to the central axis of the tampon. As a result, the grooves extend radially outwards, having a constant pattern from the surface to the core. Such machines are known for example from EP 0 422 660 and EP 0 639 363.

The press apparatus of the current invention is described in detail below and a non-limiting illustrative example is provided by FIGS. 18A to 18E. FIG. 18A shows press jaws 60 of a press according to the invention, each having a penetrating segment 63 protruding from a pressing head 65, said press jaws 60 in open position, arranged around a central axis 69 of the press (press axis). FIGS. 18B to E shows the press jaws gradually closing and penetrating the tampon blank shown in cross section 8, resulting in a pressed tampon 151 in FIG. 18F. The star-shaped press configuration is described in the art, for example, in DE 1993-004304505, DE 1989-003934153, and DE 1993-004325220.

The press apparatus of the current invention comprises a press having press jaws 60 which are arranged in a star formation with respect to the press (central) axis 69 and preferably at the same radial distance from the press axis 69. They can be moved in a common plane towards the core of the press between their open position and closed position and, in their closed position, are supported on one another on their mutually opposite longitudinal sides. A preferred press consists of eight press jaws. It is desirable to equip the press with an even number of press jaws, but other numbers of press jaws can be used, including odd numbers. The number of press jaws can vary, for example depending on the weight and the composition of the material intended for the tampon and can also be smaller or greater than eight, although the number generally should not be under three.

One press jaw may comprise either a penetrating segment 63 or a pressing shoulder 64, (FIG. 19) or a combination of one penetrating segment 63 and pressing shoulders 64 arranged at either or both sides of the penetrating segment. If the penetrating segments and the pressing shoulders are fixed to separate press jaws, said penetrating segments and pressing shoulders may press separately or simultaneously. It is preferable that they press simultaneously, preferably in one single pressing operation. The pressing shoulders may be straight or angular, but preferably have a curvature in the transversal direction in order to press the circumferential surface of the tampon blank into an essentially cylindrical form of smaller diameter.

The press jaws 60 can preferably be heated and preferably each press jaw has its own temperature sensor. By heating the press jaws, it is possible to reduce the memory effect of modern, highly absorbent, greatly expanding fibrous materials, which occurs after the tampon has been finished. By means of the heated press jaws, and especially the heated pressing shoulders, the surface of the tampon is simultaneously smoothed during pressing and pushing out, and a qualitatively improved surface is produced in the preformed tampon even in tampon preforms of low weight, the stability of the tampon preform being preserved. The memory effect of the fibrous material becomes effective again when the fibrous material of the tampon is wetted with body fluid.

PS Longitudinal Path

At least one penetrating segment 63 is defined by a plurality of longitudinal paths (PS longitudinal paths) 70. They extend along the direction of the press axis 69. They stack in the direction from the pressing head 65 to the extremity 67 of a penetrating segment 63. According to the invention, at least two PS longitudinal paths are different from each other i.e. they diverge from each other. Preferably the majority of PS longitudinal paths are divergent from each other. Preferably, the PS longitudinal paths diverge gradually in the direction from the pressing head 65 to the extremity 67 of a penetrating segment 63.

According to a preferred aspect of the invention, the PS longitudinal path which forms the groove on the surface of the tampon is divergent from a PS longitudinal path which forms a groove below the surface of the tampon. In other words, the PS longitudinal path at the base of the penetrating segment where it joins the pressing head, known herein as the PS outer longitudinal path, is divergent from a PS longitudinal path towards the extremity 67 of the penetrating segment 63.

The divergence can be any form, for example, in appearance, shape, inclination, amplitude, form, size, frequency, scale. For example, one PS longitudinal path may be inclined to another (e.g. the outer) PS longitudinal path. Alternatively, the one PS longitudinal path may adopt a wave-shaped (curved) pattern, a saw tooth pattern etc, having one, two or more points of inflection or crossing, compared to a different path of another (e.g. the outer) PS longitudinal path. Alternatively, one PS longitudinal path may adopt an undulating pattern, a saw tooth pattern etc, having a greater amplitude compared with a similar pattern of another (e.g. the outer) PS longitudinal path. Generally any divergence which increases the length of one PS longitudinal path compared with another (e.g. the outer) PS longitudinal path is envisaged.

Figure 20:
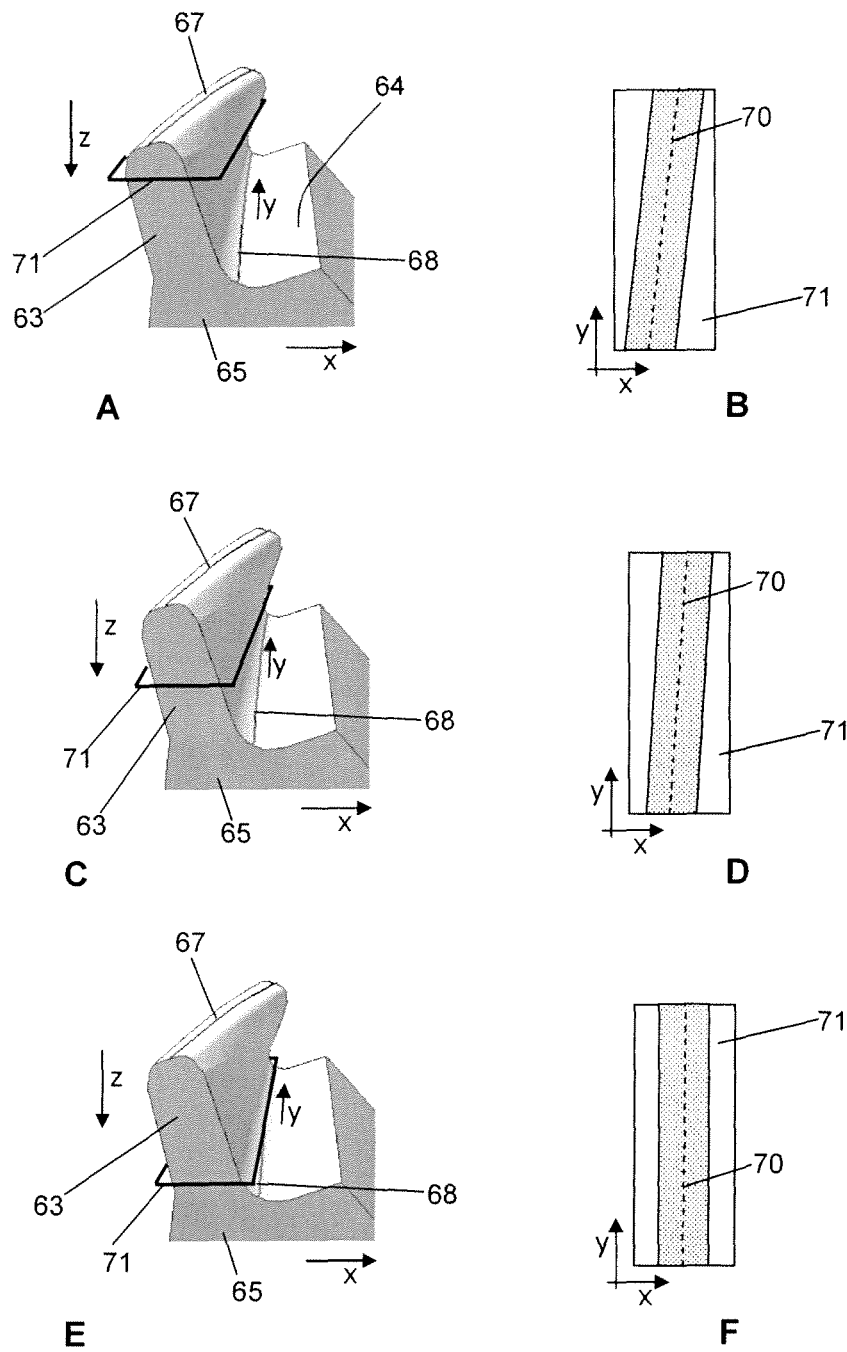

With reference to, for example, FIG. 20 the longitudinal path 70 of a penetrating segment (PS longitudinal path) may be defined as the longitudinal midpath across an x-y plane 71 of a penetrating segment 63 which plane is a slice perpendicular to the z-axis of the press jaw 60. The y-axis is parallel to the longitudinal axis 68 of the pressing shoulder 64 of the press jaw 60. Alternatively, it may be considered parallel to the press axis 69. The x-axis is perpendicular thereto, and the z-axis is along the direction of movement of the press jaw 60 and is perpendicular to both the x- and y-axes. The value of z is lower at the extremity 67 of the penetrating segment (e.g. z=0 or z=0.0001) and increases towards the pressing head 65. Generally the majority of inner longitudinal paths are divergent from each other e.g. a block of 55%, 60%, 70%, 80%, 90% or more consecutive inner longitudinal paths. Preferably the differing paths give rise to a path length that decreases in the direction from the extremity 67 of the penetrating segment 63 to the pressing head 65. Alternatively the differing paths may give rise to a path length that increase in the direction from the extremity 67 of the penetrating segment 63 to the pressing head 65. Thus, the three dimensional shape of a penetrating segment 63 may be derived from a series of consecutive PS longitudinal paths 70 across a stack of x-y planes 71.

According to the invention, the PS longitudinal path 70 in an x-y plane 71 changes gradually or abruptly in the direction from the extremity 67 of a penetrating segment 63 to the pressing head 65, i.e. along the z-axis. This compares with the prior art where the longitudinal path of each penetrating segment is constant in the direction along the z-axis.

The PS longitudinal path between successive x-y planes in the z-direction may diverge in a plurality of ways. For example, the shape (e.g. from sinusoidal to sawtooth), the amplitude of undulations (e.g. from pronounced to gentle wave), and/or inclination (e.g. from inclined with the y-axis to aligned with the y-axis). It is preferred that the change of shape increases the PS longitudinal path length as the value of z decreases. Alternatively, the change of shape increases the PS longitudinal path length as the value of z decreases. In addition to changes to the longitudinal path, said path may or may not be displaced along the x-axis in successive x-y planes.

PS Longitudinal Path is Inclined

According to one aspect of the invention, the PS longitudinal path changes in that the inclination of the path gradually changes as the value of z changes. As z increases, the inclination may decrease as the PS longitudinal path progressively aligns with the y-axis, as it moves towards the pressing head. This embodiment is exemplified in FIGS. 20A to 20F. FIG. 20A shows the position of an x-y plane 71 on a penetrating segment 63 of a press jaw, perpendicular to the z-axis, close to extremity of the segment 67. The PS longitudinal path 70 in the x-y plane 71 of FIG. 20A is shown in FIG. 20B, which comprises a straight line, inclined to the y-axis. As the value of z increases (FIGS. 20C and 20D), the angle of inclination with respect to the y-axis decreases; the PS longitudinal path in FIG. 20D is less inclined. FIGS. 20B and 20D clearly demonstrate the aforementioned change in the PS longitudinal path as the value of z increases. FIG. 20F shows the PS longitudinal path at the base of the penetrating segment known herein as the PS outer longitudinal path) is a straight line parallel to the y-axis. While FIG. 20F is a line parallel to the y-axis, it may equally well be an inclined line, having less inclination that the PS longitudinal paths in x-y planes closer to the extremity 67 of the penetrating segment (FIGS. 20B and 20D).

In an alternative embodiment (not illustrated), as z increases, the inclination increase and the PS longitudinal path progressively diverges from the y-axis, as it moves towards the pressing head.

According to one embodiment, the PS longitudinal path of a press jaw corresponds to an inclined line in the x-y plane, showing the function $$x=((y \cdot a)/z)+b$$

wherein a is different from zero and is constant, b is an offset which can be constant or can change in proportion to the value of z,
wherein y corresponds to a value along the y-axis,
wherein x corresponds to a value along the x-axis,
wherein z corresponds to a value along the z-axis.

According to another embodiment, the PS longitudinal path of a press jaw corresponds to an inclined line in the x-y plane, showing the function $$x=(z \cdot y \cdot a)+b$$

wherein a is different from zero and is constant, b is an offset which can be constant or can change in proportion to the value of z,
wherein y corresponds to a value along the y-axis,
wherein x corresponds to a value along the x-axis,
wherein z corresponds to a value along the z-axis.

PS Longitudinal Path is Undulated

According to one aspect of the invention PS longitudinal path is undulated. The amplitude of at least one undulation gradually changes as the value of z changes, but the frequency of undulations remains the same. An undulated line is a wave-like line that has a regular curvature, such as a sinusoidal curvature, or a cosinusoidal curvature. There may be one or more points of inflection where the curvature changes sign. This embodiment is exemplified in FIGS. 21-1A, 21-1B, 21-1D, 21-1E, 21-1G 21-1H and 21-2A, 21-2B, 21-2D, 21-2E, 21-2G, and 21-2H.

FIG. 21-1A shows the position of an x-y plane 71, perpendicular to the z-axis, close to the extremity of the penetrating segment 63. The PS longitudinal path 70 in the x-y plane 71 of FIG. 21-1A is shown in FIG. 21-1B, which comprises an undulating line. As the value of z increases (FIGS. 21-1D and 21-1E) the amplitude of an undulation decreases; the longitudinal path in FIG. 21-1E has a reduced amplitude in respect of the undulations. FIGS. 21-1B and 21-1E clearly demonstrate the aforementioned change in the PS longitudinal path as the value of z increases. FIG. 21-1H shows the PS longitudinal path of the x-y plane (FIG. 21-1G) at the base of the penetrating segment (known herein as the PS outer longitudinal path) is a gently undulating line, having less amplitude that the PS longitudinal paths in x-y planes closer to the extremity 67 of the penetrating segment (FIGS. 21-1B and 21-1E). While FIG. 21-1H is a gently undulating line, it may equally well be a straight line parallel to the y-axis.

FIG. 21-2A shows the position of an x-y plane 71, perpendicular to the z-axis, close to the extremity of the penetrating segment 63. The PS longitudinal path 70 in the x-y plane 71 of FIG. 21-2A is shown in FIG. 21-2B, which comprises a gently undulating line. While FIG. 21-2B is a gently undulating line, it may equally well be a straight line parallel to the y-axis. As the value of z increases (FIGS. 21-2D and 21-2E) the amplitude of the undulation increases; the longitudinal path in FIG. 21-2E has increased amplitude in respect of the undulations. FIGS. 21-2B and 21-2E clearly demonstrate the aforementioned change in the PS longitudinal path as the value of z increases. FIG. 21-2H shows the PS longitudinal path of the x-y plane (FIG. 21-2G) at the base of the penetrating segment (known herein as the PS outer longitudinal path) is an undulating line, having the greatest amplitude compared with the PS longitudinal paths in x-y planes closer to the extremity 67 of the penetrating segment (FIGS. 21-2B and 21-2E).

According to one aspect of the invention the frequency of undulations in a PS longitudinal path changes as the value of z changes. As the value of z increases, the frequency of undulations may decrease, or vice versa.

PS Longitudinal Path is a Curve with Convex/Concave Parts

According to one aspect of the invention, the PS longitudinal path 70 of a penetrating segment is at least partly curved, having one or more points of inflection which inflection point defines a convex part and a concave part. Examples of curved line shapes include asymptotic. As z increases, the amplitude of the convex and/or concave parts may decrease as the path progressively aligns with the y-axis of the jaw in a direction towards the pressing head. The PS longitudinal path at the base of the penetrating segment (i.e. PS outer longitudinal path) may be a straight line, having no amplitude. Alternatively it may adopt the same path as the PS longitudinal path 70, but with a decrease in amplitude. In an alternative embodiment, as z increases, the amplitude of the convex and/or concave parts may increase in a direction towards the pressing head. The PS longitudinal path at the extremity 67 of the penetrating segment may be a straight or gently undulating line, having less amplitude that the PS longitudinal paths in x-y planes closer to base of the penetrating segment. These embodiments is exemplified in FIGS. 21-1A, 21-1C, 21-1D, 21-1F, 21-1G and 21-1I and in FIGS. 21-2A, 21-2C, 21-2D, 21-2F, 21-2G and 21-2I.

FIG. 21-1A shows the position of an x-y plane 71, perpendicular to the z-axis, close to extremity of the penetrating segment. The PS longitudinal path 70 in the x-y plane of FIG. 21-1A is shown in FIG. 21-1C, which comprises a curved line having one point of inflection, which inflection point defines a convex part and a concave part with respect to the y-axis. As the value of z increases (FIGS. 21-1D and 21-1F), the amplitude of both concave and convex parts with respect to the y-axis decreases; the PS longitudinal path 70 in FIG. 21-1F shows a reduced amplitude in respect of both convex and concave parts. FIGS. 21-1C and 21-1F clearly demonstrate the aforementioned change in the PS longitudinal path 5 as the value of z increases. FIG. 21-1I shows the PS longitudinal path of the x-y plane (FIG. 21-1G) at the base of the penetrating segment (known herein as the PS outer longitudinal path) is a gently undulating line, having less amplitude that the PS longitudinal paths in x-y planes closer to the extremity 67 of the penetrating segment (FIGS. 21-1C and 21-1F). While FIG. 21-1I is a gently undulating line, it may equally well be a straight line parallel to the y-axis.

FIG. 21-2A shows the position of an x-y plane 71, perpendicular to the z-axis, close to extremity of the penetrating segment. The PS longitudinal path 70 in the x-y plane of FIG. 21-2A is shown in FIG. 21-2C, which comprises a curved line having one point of inflection, which inflection point defines a convex part and a concave part with respect to the y-axis. While FIG. 21-2C is a gently undulating line, it may equally well be a straight line parallel to the y-axis. As the value of z increases (FIGS. 21-2D and 21-2F), the amplitude of both concave and convex parts with respect to the y-axis increases; the PS longitudinal path 70 in FIG. 21-2F shows an increased amplitude in respect of both convex and concave parts. FIGS. 21-2C and 21-2F clearly demonstrate the aforementioned change in the PS longitudinal path 5 as the value of z increases. FIG. 21-2I shows the PS longitudinal path of the x-y plane (FIG. 21-2G) at the base of the penetrating segment (known herein as the PS outer longitudinal path) is an undulating line, having the greatest amplitude compared with the PS longitudinal paths in x-y planes closer to the extremity 67 of the penetrating segment (FIGS. 21-2A and 21-2C).

The term "point of inflection", "convex part", "concave part" have been defined above in respect of the tampon.

In one embodiment, the PS longitudinal path of a press jaw corresponds to a curved line in an x-y plane, showing the function $$x=((a \cdot y^{-m})/z)+b$$

wherein m is an odd positive whole number which is different from 1, wherein a is a constant, different from zero, b is an offset which can be constant or can change in proportion to the value of z, wherein y corresponds to a value along the y-axis, which is defined above, wherein x corresponds to a value along the x-axis which is defined above, wherein z corresponds to a value along the z-axis, where x, y, and x in respect of a press jaw are defined above.

In another embodiment, the PS longitudinal path of a press jaw corresponds to a curved line in an x-y plane, showing the function $$x=(z \cdot a \cdot y^{-m})+b$$

wherein m is an odd positive whole number which is different from 1, wherein a is a constant, different from zero, b is an offset which can be constant or can change in proportion to the value of z, wherein y corresponds to a value along the y-axis, which is defined above, wherein x corresponds to a value along the x-axis which is defined above, wherein z corresponds to a value along the z-axis, where x, y, and x in respect of a press jaw are defined above.

The above-referred function is a power function wherein x, y and z are the variables that are to be related, parameters a and m describe the relationship. The parameter a increases the amplitude of the curve i.e. moves the values for x, up or down as an increase or decrease, respectively. The parameter b is an offset which can displace the curve along the x-axis. It can be constant or can change with the value of z. The parameter m, determines the function's rates of growth or decay. Preferably the parameter m is a positive and odd whole number, different from zero and one and for instance 3, 5, 7, 9, etc. the parameter a is different from zero and may for instance be −6, −5, −4, −3, −2, −1, 1, 2, 3, 4, 5, 6, etc.

In a particularly preferred embodiment, the PS longitudinal path 5 of a press jaw corresponds to a curved line showing the function $x=a \cdot y^{-3}/z+b$ or $x=z \cdot a \cdot y^{-3}$.

In alternative preferred embodiment, the PS longitudinal path 5 of a press jaw follows the path of a continuous hyperbolic function or to a continuous inverse hyperbolic. The term "continuous" as used herein refers to a curve or function, which extends without break or irregularity.

In a preferred embodiment, the hyperbolic function corresponds to any of the following hyperbolic functions $y=z(\sin h(x))/a$; $y=\sin h(x)/za$; $y=z(\tan h(x))/a$ or $y=\tan h(x)/za$. The functions $y=z \cdot (\sin h(x))/a$ and $y=\sin h(x)/za$ correspond to a hyperbolic sine of x (see FIG. 8A), and can also be written as $y=z \cdot (\sin h(x))/a = z \cdot (e^x - e^{-x})/2a$ or $y=(\sin h(x))/za = (e^x - e^{-x})/2za$ respectively. The functions $y=z \cdot (\tan h(x))/a$ $y=(\tan h(x))/za$ correspond to a hyperbolic tangent of x (see FIG. 8B), and can also be written as $y=z \cdot \sin h(x)/a \cdot \cos h(x)$ or $y=\sin h(x)/z \cdot a \cdot \cos h(x)$ respectively whereby $\sin h(x)$ is $(e^x - e^{-x})/2$ and $\cos h(x)$ is $(e^x + e^{-x})/2$.

In a particularly preferred embodiment, the inverse hyperbolic function corresponds to the function $y=z \cdot (\text{artan } h(x))/a$ or $y=(\text{artan } h(x))/z \cdot a$, wherein y and x correspond to values in the x-y plane. The functions $y=z \cdot (\text{artan } h(x))/a$ and $y=(\text{artan } h(x))/z \cdot a$ corresponds to inverse hyperbolic tangent of x (see FIG. 8C).

The values for x and y in the above-indicated power or hyperbolic function may be as follows: x may be a value that is comprised between +½ W and −½ W and y may be a value that is comprised between +½ L and −½ L, z may be a value that is comprised between +½ W and −½ W.

Single Inflection Point for PS Longitudinal Path

According to one embodiment of the invention, a curved PS longitudinal path in an x-y plane has only one point of inflection 6, which inflection point defines one convex part and one concave part.

In a preferred embodiment, said point of inflection is substantially located in the middle part of the tampon longitudinal body. Preferably point of inflection is located in a region covering the middle 50% of the tampon longitudinal body area. Even more preferred, this point of inflection is located about an imaginary line that is parallel to the y-axis. It is noted that it is of utmost importance in the present penetrating segment configuration that only one point of inflection is provided in the PS longitudinal path. Because there is only one point of inflection, the path will undergo only one change in direction. As a consequence thereof, friction between the tampon grooves and the pressing apparatus can be considerably minimized.

In a preferred embodiment, the press jaw is characterised in that the PS longitudinal path corresponds to a continuous curved line, which is point symmetric in relation to said point of inflection.

In a particularly preferred embodiment, the press jaw is characterised in that the PS longitudinal path corresponds to a continuous curved line which does not show a point having a first derivative equal to zero. In other words, the curve describing path of PS longitudinal path does not show a minimum and/or maximum.

The PS longitudinal path may correspond to a continuous curved line, which preferably does not show any points wherein a first derivative is equal to zero. However, in an alternative embodiment, the PS longitudinal path may correspond to a curved line showing one or two points which have a first derivative equal to zero. A first such point may be located in the top 25% of the penetrating segment longitudinal length, and for instance be located part which presses the insertion end of the tampon. A second such point may be located in the bottom 25% of the penetrating segment longitudinal body length, and for instance be located in the part that presses the withdrawal end of the tampon. In an embodiment, a press jaw is provided, wherein said PS longitudinal path shows only one point which has a first derivative equal to zero, whereby a first point is located in the top 25% or the bottom 25% of the penetrating segment longitudinal length. In another embodiment, a press jaw is provided wherein said curved line shows maximally two points which has a first derivative equal to zero, whereby a first point is located in the top 25% and a second point is located in an the bottom 25% of the penetrating segment longitudinal length. In yet another embodiment, a press jaw is provided wherein said point wherein the first derivative equal to zero is located at the top of the penetrating segment longitudinal length, i.e. at −½ L, and/or at the bottom of the penetrating segment longitudinal length, i.e. at +½ L.

Parallel or Inclined PS Outer Longitudinal Path

According to one non-limiting aspect of the invention, the PS longitudinal path at the base of the penetrating segment i.e. where it joints the pressing head, describes a straight line. According to one aspect of the invention, the PS longitudinal path at the base 66 of the penetrating segment (known herein as the PS outer longitudinal path) is parallel to the y-axis of the press jaw (or parallel to the press axis 69), giving rise to pressed tampons with a having a straight groove appearance. In other words, the PS outer longitudinal path is parallel to the y-axis of the press jaw or is parallel to the press-axis 67. According to one aspect of the invention, when the press jaw is viewed end on (i.e. along the y-axis, along the press-axis 69, or along arrow 191 in FIG. 22), the distal and proximal end points of the PS outer longitudinal path coincide (not shown); this arises in the case where a pressing produces a tampon having a straight grooves appearance on the surface.

According to another aspect of the invention, the PS outer longitudinal path of a penetrating segment may be inclined (FIG. 22A to C), to the y-axis of the press jaw (or to the press axis 69), so producing pressed tampons with an inclined groove appearance.

As shown in FIG. 22B, the angle of inclination can be defined according to the angle, epsilon, adopted between the PS outer longitudinal path 70 at the base of the penetrating segment where it joins the pressing head, and the y-axis. Alternatively, the angle of inclination can be defined according to the angle, epsilon, adopted between the PS outer longitudinal path 70 at the base of the penetrating segment where it joins the pressing head, and the press axis 69. The y-axis or press axis 69 crosses the PS outer longitudinal path 70 in question, so creating the angle of inclination epsilon.

The value of epsilon can be greater or smaller than zero, plus or minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43, 44, 45, 46, 47, 48, 49, 50, 55, 60, 65, 70, 75, 80, 85, 89, 90 deg, or a value in the range between any two of the aforementioned values, preferably 10 to 50 deg, more preferably 20 to 40, and most preferably 25 to 30 deg. It may be −10 to −50 deg, more preferably −20 to −40, and most preferably −25 to −30 deg. In the preferred range, the production process is improved in the compression and the ejection of the pressed product.

According to another aspect of the invention, when the x-y plane is viewed end on (i.e. along the y-axis or along arrow 191) as in FIG. 22C, the distal p2 and proximal p1 end points of the PS outer longitudinal path 70 do not coincide. The offset, called d (FIG. 22D), when viewed along the y-axis, may be greater than zero, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43, 44, 45, 46, 47, 48, 49, 50, 55, 60, 65, 70, 75, 80, 85, 89, 90% of the width of tampon to be formed, or a value in the range between any two of the aforementioned values, preferably 10 to 50%, more preferably 20 to 40%, and most preferably 25 to 30. In the preferred range, the production process is improved in the compression and the ejection of the pressed product.

Displacement of PS Longitudinal Path

According to one aspect of the invention, the PS longitudinal path in an x-y plane not only changes shape as z changes, but it is gradually displaced in the direction of the x-axis as z changes. As z increases, the displacement from the original position may gradually increase as the PS longitudinal path 5 rises from the extremity 67 to the base 66 of the penetrating segment. The effect of the displacement gives rise to a tampon which, when viewed in transverse cross-section, shows a groove that is divergent from the radius. The effect on the tampon is exemplified in FIG. 11 which is a schematic illustration of a transverse (B-B') cross-section of a tampon according to the present invention. It can be seen from FIG. 11 that the transverse path 111 of a groove 9 does not coincide with the radius of the groove 112, but diverges therefrom.

According to one aspect of the invention, at least one penetrating segment 63 penetrates the absorbing material in a line diverging from the radius. At least one penetrating segment may have a median 203 (FIG. 23) which is a line drawn through the middle of the cross-section of a penetrating segment 63 so that the distance from either side of the line to the extremity 67 of the penetrating segment is the same. According to another aspect of the invention, the median 203 of a penetrating segment 63 may be the straight line drawn, in a cross-section of a penetrating segment, through its extremity 67 and the midpoint of its base 66 (FIG. 23A). According to a preferred aspect of the invention (FIGS. 23B to D), the median 203 of a penetrating segment 63 is the straight line drawn, in a composite view 208 (FIG. 23D) of penetrating segment cross-section whereby cross-sections (205, 206, 207, FIG. 23B) of a penetrating segment along the y-axis are overlaid (FIG. 23C) to form said composite view 208 (FIG. 23D), through the extremity 67 and the midpoint of its base 66 of the penetrating segment in composite view. Said overlays are preferably aligned using the profile of the pressing head 65 which has a constant shape in cross-section.

According to one embodiment of the invention, when the median 203 of a penetrating segment is a straight line, it forms a minimum angle, theta, of greater or smaller than zero, ±1, 2, 3, 4, 5, 6, 7, 8, 9, 10, 11, 12, 13, 14, 15, 16, 17, 18, 19 or 20 deg and a maximum angle of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 deg vis à vis the radius 203 of the corresponding penetrating segment, or a value in a range between any two of the aforementioned values.

According to another embodiment of the invention, when a median 203 of a penetrating segment is a straight line, it forms an angle between 1° and 60° (or −1° and −60°) vis à vis the radius of the corresponding penetrating segment, preferably an angle between 1° and 30° (or −1° and −30°) and more preferably an angle between 10° and 20° (or −10° and −20°). The median 203 of the penetrating segment 63 preferably forms an angle epsilon of about ±15° with the radius 211 of the penetrating segments 63.

The "radius of the penetrating segment", as used herein, refers to the straight radial line 211 running through the midpoint 212 of the fictive circle 213 formed by the extremity 67 of the penetrating segments 63, to the extremity of the penetrating segment in question, when the press jaws are in the closed position. Alternatively, the "radius of the penetrating segment", as used herein, refers to the straight radial line 211 running through the central (press) axis 69 to the extremity of the penetrating segment in question, when the press jaws are in the closed position. The radius of the penetrating segment can be seen in FIGS. 24 and 25.

According to one embodiment of the invention, angle theta is obtained by providing a press jaw comprising a penetrating segment 63 which median 203 diverges from the line of movement of the press jaw 223 as shown in FIG. 24. The line 223 of movement of the press jaw is essentially towards the midpoint 212 of the fictive circle 213 or press axis.

According to another embodiment of the invention angle theta is obtained by providing a press jaw comprising a penetrating segment 63 which median 203 is essentially parallel to the line of movement of the press jaw 223 as shown in FIG. 25. The line 223 of movement of the press jaw essentially diverges from the midpoint 212 of the fictive circle 213 or press axis.

According to one aspect of the invention, the radial distance 602 (FIG. 26) between the midpoint 212 of the fictive circle 213 formed by the extremities 67 of the penetrating segments 63, and the extreme of a penetrating segment 63 and/or the radial distance 603 between the midpoint 212 of the fictive circle 213 formed by the extremes 67 of the penetrating segments 63, and the pressing shoulder (64 or 64') is constant along the longitudinal axis of the press. Such measurement, indicative of the impression depth, is preferably taken when the jaws are in the closed position. An impression depth provides a tampon of constant diameter and grooves of constant depth in the longitudinal direction.

According to one aspect of the invention, the radial distance 602 (FIG. 26) between the midpoint 212 of the fictive circle 213 formed by the extremities 67 of the penetrating segments 63, and the extreme of a penetrating segment 63 and/or the radial distance 603 between the midpoint 212 of the fictive circle 213 formed by the extremes 67 of the penetrating segments 63, and the pressing shoulder (64 or 64') varies along the longitudinal axis. As already mentioned such measurement, indicative of the impression depth, is preferably taken when the jaws are in the closed position.

Complete or Incomplete PS Longitudinal Path

Variation in the impression depth along the longitudinal axis of the press allows tampons of different shapes to be formed. The shape is reflected in the longitudinal cross-section of a press, when the press jaws are closed. According to one aspect of the invention, said variation in impression depth provides a mushroom-shaped profile of a longitudinal cross-section of a press, when the press jaws are closed. Accordingly, the arrangement is capable of producing mushroom-shaped tampons. According to another aspect of the invention, said variation in impression depth provides a rivet-shaped profile of a longitudinal cross-section of a press, when the press jaws are closed. Accordingly, the arrangement is capable of producing rivet-shaped tampons. According to another aspect of the invention, said variation in impression depth provides a profile which has a dome head, a straight body and conical withdrawal end, when the press jaws are closed. Accordingly, the arrangement is capable of producing tampons with a domed insertion end and a conical withdrawal end.

The impression depth of along longitudinal axis of the press is reflected by a complete or incomplete PS longitudinal path. According to one aspect of the invention, the PS longitudinal path in an x-y plane is a line that remains complete as z changes. By complete, it is meant that the PS longitudinal path in an x-y plane extends from a distal end to a proximal end of the press jaw without interruption or truncation as z changes. The PS longitudinal path as a complete line is present in x-y planes towards the extremity of the penetrating segment, and essentially disappears beyond the extremity in a complete manner. This embodiment is exemplified in FIGS. 21B, 21C, 21E, 21F, 21H and 21I where each of the PS inner longitudinal paths 70 are complete lines.

According to another aspect of the invention, the PS longitudinal path in an x-y plane changes gradually or abruptly from a complete line to an incomplete line as z changes. By incomplete, it is meant that the PS longitudinal path extends across one x-y plane without interruption or truncation, but becomes interrupted or truncated in another x-y plane as z changes. The PS longitudinal path as a complete line is present from the pressing head end of the penetrating segment, but becomes incomplete towards the extremity of the penetrating segment and essentially disappears altogether beyond the extremity of the penetrating segment. The incompleteness arises as the value of z decreases i.e. more incompleteness towards the extremity of the penetrating segment. Preferably, the path becomes incomplete towards the extremity of the penetrating segment at the proximal and/or distal end press jaw, so giving rise to a pressed tampon which has barrel-shape upon expansion. Preferably the transition from complete to incomplete lines is gradual. Thus incomplete PS inner longitudinal path provides a variation in the impression depth along the longitudinal axis by the pressing apparatus.

u-Shaped Impression Profile

According to one aspect of the invention, the PS longitudinal path 70 in an x-y plane becomes incomplete towards the extremity 67 of the penetrating segment 64, so as to give a u-shaped impression profile. The u-shape is evident in the tampon when the groove is viewed as a y-z projection, and the groove is uppermost as depicted, for example, in FIGS. 12A to 12H. Importantly, this reflected by a PS longitudinal path 70 which is incomplete in at the ends towards the extremity 67 of the penetrating segment 63. Preferably the transition from complete to incomplete path is gradual. This embodiment is exemplified in FIGS. 27A to 27I. FIG. 27A shows the position of an x-y plane 71, perpendicular to the z-axis, close to extremity of the penetrating segment 63. The PS longitudinal path 70 in the x-y plane 71 of FIG. 27A is shown in FIG. 27C, comprises an undulating line which is incomplete, being truncated 251 at a proximal end, and truncated 252 at a distal end. The shape of penetrating segment 63 giving rise to this truncation pattern is shown in FIG. 17B, which is n-shape, viewed when the penetrating segment is pointing upwards. As the value of z increases (FIGS. 27D, 27E and 27F), the extent of truncation 251 is reduced and the line gradually becomes more complete; the PS longitudinal path 70 in FIG. 27F shows less truncation 251, 252 at the ends. FIGS. 27C and 27F clearly demonstrate the aforementioned change in the PS longitudinal path 70 as the value of z decreases. FIG. 27I shows the PS longitudinal path 70, at the base of the penetrating segment, which path is visible on the surface of the tampon which is complete. It is noted that the PS path also changes as z-changes in accordance to the invention i.e. the amplitude of the undulations decrease as z increases.

n-Shaped Impression Profile

According to one aspect of the invention, the PS longitudinal path 70 in an x-y plane becomes incomplete towards the extremity 67 of the penetrating segment 64, so as to give a n-shaped impression profile. The n-shape is evident in the tampon when the groove is viewed as a y-z projection, and the groove is uppermost as depicted, for example, in FIGS. 13A to 13H. Importantly, this reflected by a PS longitudinal path 70 which is incomplete in a longitudinal central region towards the extremity 67 of the penetrating segment 63. Preferably the transition from complete to incomplete path is gradual. This embodiment is exemplified in FIGS. 28A to 28I. FIG. 28A shows the position of an x-y plane 71, perpendicular to the z-axis, close to extremity of the penetrating segment 63. The PS longitudinal path 70 in the x-y plane 71 of FIG. 28A is shown in FIG. 28C, comprises an undulating line which is incomplete, being truncated 251 in a central region. The shape of penetrating segment 63 giving rise to this truncation pattern is shown in FIG. 28B, which is u-shape, viewed when the penetrating segment is pointing upwards. As the value of z increases (FIGS. 28D, 28E and 28F), the extent of truncation 251 is reduced and the line gradually becomes more complete; the PS longitudinal path 70 in FIG. 28F shows less truncation 251 in a central portion. FIGS. 28C and 28F clearly demonstrate the aforementioned change in the PS longitudinal path 70 as the value of z decreases. FIG. 28I shows the PS longitudinal path 70, at the base of the penetrating segment, which path is visible on the surface of the tampon which is complete. It is noted that the PS path also changes as z-changes in accordance to the invention i.e. the amplitude of the undulations decrease as z increases.

Undulating Impression Profile

According to one aspect of the invention, the PS longitudinal path 70 in an x-y plane becomes incomplete towards the extremity 67 of the penetrating segment 64, so as to give an undulating impression profile. The undulating shape is evident in the tampon when the groove is viewed as a y-z projection, and the groove is uppermost as depicted, for example, in FIGS. 14A to 14H. Importantly, this reflected by a PS longitudinal path 70 which is regularly interrupted in the longitudinal direction towards the extremity 67 of the penetrating segment 63. Preferably the transition from complete to incomplete path is gradual. This embodiment is exemplified in FIGS. 29A to 29I. FIG. 29A shows the position of an x-y plane 71, perpendicular to the z-axis, close to extremity of the penetrating segment 63. The PS longitudinal path 70 in the x-y plane 71 of FIG. 29A is shown in FIG. 29C, comprises an undulating line which is regularly interrupted 251, 251, 251". The shape of penetrating segment 63 giving rise to this truncation pattern is shown in FIG. 29B, which is u-shape, viewed when the penetrating segment is pointing upwards. As the value of z increases (FIGS. 29D, 29E and 29F), the extent of truncation 251, 251, 251" is reduced and the line gradually becomes more complete; the PS longitudinal path 70 in FIG. 29F shows less truncation 251, 251, 251". FIGS. 29C and 29F clearly demonstrate the aforementioned change in the PS longitudinal path 70 as the value of z decreases. FIG. 29I shows the PS longitudinal path 70, at the base of the penetrating segment, which path is visible on the surface of the tampon which is complete. It is noted that the PS path also changes as z-changes in accordance to the invention i.e. the amplitude of the undulations decrease as z increases.

Process for Manufacture

The invention further concerns a process for manufacturing the tampon of the invention. The tampons according to the present invention can be easily and rapidly manufactured by a process using a press apparatus showing press jaws with penetrating segments or cogs, such as, for instance, described in the European patent application having application number 03447303.3, in DE 1993-004304505, DE 1989-003934153 or DE 1993-004325220. Herein, the tampon blank is pressed with such pressing apparatus. A blank is generally a strip of absorbent material having acceptable absorbency and modulus of elasticity properties that is capable of absorbing and/or retaining liquid, is wound up on itself to form an essentially cylindrical tampon blank. In order to form the ribs of the tampon, the method comprises compressing the tampon blank on its outer circumferential surface, forming longitudinal grooves and a fibre core. Preferably, the fibre core has a higher degree of compression from which less compressed longitudinal ribs extend outwards. The degree of compression in the ribs is less than in tampons of the prior art, allowing the absorption of more liquid.

The process essentially comprising the steps of:
inserting an essentially cylindrical blank of absorbing material in a press comprising press jaws including penetrating segments and pressing shoulders,
pressing tampon blank in the press jaws, so that the penetrating segments penetrate the cylindrical blank around its circumference to form ribs defined by grooves and the pressing shoulders press on the circumferential surface of the ribs so-formed,
ejecting the so-formed pre-form,
subjecting the pre-form to further pressure around its total circumference, so forming a tampon.

The manufacturing method is easy, rapid and cost-effective, since material loss can be significantly reduced.

In a preferred embodiment the process for producing a tampon according to the invention comprises the steps of:
providing a tampon blank of fibrous material having a longitudinal axis;
compressing in a press the tampon blank and forming longitudinal grooves at an outer circumferential surface of the tampon whereby at least one tampon groove is defined an outer longitudinal path 2 on the surface of the tampon and an inner longitudinal path 5 below the surface of the tampon whereby the inner longitudinal path 5 is at least partly divergent from the outer longitudinal path (2) or longitudinal groove axis 7.
withdrawing said pressed tampon out of the press in a longitudinal direction of the tampon body.

In another preferred embodiment the method for producing a tampon according to the invention comprises the steps of:
providing a tampon blank of fibrous material having a longitudinal axis;
compressing in a press the tampon blank and forming longitudinal grooves at an outer circumferential surface of the tampon, wherein at least one tampon groove is defined by a plurality of inner longitudinal paths 5 below the surface of the tampon whereby the inner longitudinal paths change in the direction from the core 12 of the surface of the tampon.
withdrawing said pressed tampon out of the press in a longitudinal direction of the tampon body.

In another preferred embodiment the method for producing a tampon according to the invention comprises the steps of:
providing a tampon blank of fibrous material having a longitudinal axis;
compressing in a press the tampon blank and forming longitudinal grooves at an outer circumferential surface of the tampon, which groove is defined by an inner longitudinal path 5 across a series of x-y planes 53 of the tampon which plane is a slice perpendicular to the z-axis 53, whereby the path of the inner longitudinal path 5 in an x-y plane gradually changes as the value of z increases,
withdrawing said pressed tampon out of the press in a longitudinal direction of the tampon body.

Configurations and definitions described elsewhere in regard of the inner longitudinal path 2 and outer longitudinal path apply also here to the present method.

In another preferred embodiment, the method is as defined above, wherein said tampon blank is compressed in order to form inclined longitudinal grooves at an outer circumferential surface of the tampon which follow the path in the longitudinal direction of said tampon (i.e. along the inclined longitudinal line) of a curved line showing a hyperbolic function or an inverse hyperbolic function.

In detail, a preferably cylindrical tampon blank is introduced in the press apparatus described above.

The tampon blank is compressed by press jaws around the circumference of the tampon, such as those described above. If the penetrating segments and the pressing shoulders are fixed to separate press jaws, the tampon blank may be first pressed with the penetrating segments and subsequently with the pressing shoulders. Alternatively, the penetrating segments and the pressing shoulders may press the tampon blank simultaneously. The latter will obviously be the case when the penetrating segments and pressing shoulders are fixed to the same press jaws. In the press, the tampon blank is preferably compressed in a single pressing operation by the penetrating segments and pressing shoulders simultaneously.

The penetrating segments will preferably press the tampon blank on strips of the circumferential surface that are narrower than the strips of the circumferential surface pressed by the pressing shoulders. Preferably also, the strips pressed by the penetrating segments have an equal length and width and the strips pressed by the pressing shoulders also have an equal length and width. In this way, ribs are formed, defined by longitudinal grooves on a solid fibre core. The pressing shoulders will press on the circumference of the so formed ribs in order to obtain an essentially cylindrical form with a smaller diameter. The memory effect of the tampon blank maintains the shape of the compressed tampon form.

The tampon blank, having been pressed by the penetrating segments and pressing shoulders, forms a pre-form, which is ejected from the press. This pre-form is simultaneously subjected to final shaping downstream. This final shaping includes a radial pressure being exerted on the total circumference of the pre-form. This radial pressure has the effect that the adjacent longitudinal ribs are pressed against one another, so that the grooves are substantially closed and the circumferential surface of the tampon is substantially smooth and soft.

The tampon blank is, depending on the properties of the fibrous material used, in particular in the event of use of highly expansive fibers of irregular cross section with a strong memory effect, pressed at the temperature of the press jaws to the final shape of the tampon, in order to achieve the desired dimensional stability of the fibrous material by eliminating the memory effect of the fibers, which immediately becomes effective again on contact with bodily fluid and thus increases the expansion and absorption speed of the tampon with the least possible use of fibrous material.

It is apparent that there has been provided in accordance with the invention, a tampon that fully satisfies the objects, aims, and advantages set forth above. While the invention has been described in conjunction with specific embodiments thereof, it is evident that many alternatives, modifications, and/or variations will be apparent to those skilled in the art in the light of the foregoing description. Accordingly, it is intended to embrace all such alternatives, modifications, and variations.

In one embodiment, the essentially cylindrical blank is not surrounded by a covering, particularly when the blank tampon is made from cotton. In a preferred embodiment, the essentially cylindrical blank is at least partially surrounded by a covering. The covering is preferably not provided at the portion which will form the insertion end of the tampon. In order to improve the absorbing capacity and expansion capacity of the tampon, said covering is preferably a stretchable or elastic liquid-permeable covering.

The tampon can be provided with a withdrawal cord, according to any technique known in the art.

The tampon blank is pressed with the pressing apparatus described above. In order to form the ribs of the tampon, the method comprises compressing the tampon blank on its outer circumferential surface, forming longitudinal grooves and a fibre core. Preferably, the fibre core has a higher degree of compression from which less compressed longitudinal ribs extend outward. The degree of compression in the core is less than in tampons of the prior art, allowing the absorption of more liquid. The degree of compression can be controlled, depending on the angle of divergence of the median of groove or rib from the respective radii. Preferably, the tampon blank is compressed such that said longitudinal ribs extend outward at equal circumferential angle intervals.

In detail, a preferably cylindrical tampon blank is introduced in the press apparatus described above.

The tampon blank is compressed by press jaws, such as those described above. If the penetrating segments and the pressing shoulders are fixed to separate press jaws, the tampon blank may be first pressed with the penetrating segments and subsequently with the pressing shoulders. Alternatively, the penetrating segments and the pressing shoulders may press the tampon blank simultaneously. The latter will obviously be the case when the penetrating segments and pressing shoulders are fixed to the same press jaws. In the press, the tampon blank is preferably compressed in a single pressing operation by the penetrating segments and pressing shoulders simultaneously.

The penetrating segments will preferably press the tampon blank on strips of the circumferential surface which are narrower than the strips of the circumferential surface pressed by the pressing shoulders. Preferably also, the strips pressed by the penetrating segments have an equal length and width and the strips pressed by the pressing shoulders also have an equal length and width. In this way, ribs are formed, defined by longitudinal grooves on a solid fibre core. The pressing shoulders will press on the circumference of the so formed ribs in order to obtain an essentially cylindrical form with a smaller diameter. The memory effect of the tampon blank maintains the shape of the compressed tampon form.

The tampon blank, having been pressed by the penetrating segments and pressing shoulders, forms a preform which is ejected from the press. This preform is simultaneously subjected to final shaping downstream. This final shaping includes a radial pressure being exerted on the total circumference of the preform. This radial pressure has the effect that the adjacent longitudinal ribs are pressed against one another, so that the grooves are substantially closed and the circumferential surface of the tampon is substantially smooth and soft.

The tampon blank is, depending on the properties of the fibrous material used, in particular in the event of use being made of highly expansive fibres of irregular cross section with a strong memory effect, pressed at a temperature of the press jaws to the final shape of the tampon, in order to achieve the desired dimensional stability of the fibrous material by eliminating the memory effect of the fibres, which immediately becomes effective again on contact with bodily fluid and thus increases the expansion and absorption speed of the tampon with the least possible use of fibrous material.

Alternative Embodiments of the Invention

According to an alternative embodiment of the invention, the path of the closed entrance to a groove on the circumferential surface of the tampon (2, FIG. 30A), (i.e. the outer longitudinal path 2, FIG. 30A), describes a straight line along the body of said tampon 1, while the longitudinal path of the closed groove below the surface of the tampon (i.e. an inner longitudinal path 5, FIG. 31A) is at least partly divergent from the longitudinal groove axis 7 which is defined below.

When the inner longitudinal path 5 is at least partly divergent from the longitudinal groove axis 7 its path at least partly deviates therefrom. A divergent path may mean the inner longitudinal path 5 crosses at least once, the longitudinal groove axis 7. The inner longitudinal path 5 may be, for example, inclined to the longitudinal groove axis 7. Alternatively, it may adopt a wave-shaped (curved) pattern, a saw tooth pattern etc, having one, two or more points of inflection or crossing as mentioned above.

According to one aspect of the invention, the inner longitudinal path 5 describes the longitudinal path of the closed groove below the surface of the tampon in a plane of the tampon defined by the axes x1 and y1 axes, at a depth z1.

The longitudinal groove axis 7 for a groove, is an imaginary longitudinal line at a given depth of a groove, that is parallel to the outer longitudinal path 2, and which crosses the amplitude median 161.

In other words, the longitudinal groove axis 7 for a groove, is an imaginary longitudinal line that:

on the surface of the tampon (FIG. 30A) is aligned with the outer longitudinal path 2 described by the groove on the surface, and below the surface of the tampon (FIGS. 31A, 32A, 33A), remains parallel with the outer longitudinal path 2 of a groove, and intersects the amplitude median 111 of a groove. "Below the surface of the tampon" (FIGS. 31A, 32A, 33A) can mean a plane of the tampon defined by the x1 and y1 axes, at a depth z1.

The amplitude median 161 (FIG. 39) of a groove, may be defined as a straight line drawn on a transverse (B-B') cross-section 102 of a tampon, from the outermost point 101 of the groove, to the middle point 103 of the arc centred on said point 101, which arc is bound by sides 105, 105' that are determined by the maximum variation 106, 106' of the whole groove viewed along the longitudinal axes (A-A').

The amplitude median 161 of a groove may be defined as an imaginary line drawn on a transverse (B-B') cross-section 102 of the tampon (FIG. 39), from the outermost point 101 of a closed groove 102 to the midpoint 103 of an arc 104 centred on said point 101 and bound by two side lines 105, 105', each side line 105, 105' drawn from said point 101 through a point 108, 108' where the inner longitudinal path 5 show a minimal 106' or maximal 106 deviation in the longitudinal direction of the tampon.

The point of minimal deviation 108' can be determined by drawing one longitudinal line 107' parallel to the central (A-A') axis of the tampon, which line touches a point 106' that corresponds to the minimal amplitude of the inner longitudinal path 5 in the longitudinal direction of the tampon. Where the line 107' touches the cross-section 102 corresponds to the point 108' of minimum deviation.

The point of maximum deviation 108 can be determined by drawing one longitudinal line 107 parallel to the central (A-A') axis of the tampon, which line touches a point 106 that corresponds to the maximum amplitude of the inner longitudinal path 5 in the longitudinal direction of the tampon. Where the line 107 touches the cross-section 102 corresponds to the point 108 of minimum deviation.

The amplitude median 161 lies perpendicular to the outer longitudinal path 2. It may also coincides with the points of inflection of a groove.

The amplitude median 161 will pass through the midpoint 165 of a transverse (B-B') cross-section of the tampon where the groove is essentially directed towards the centre of the tampon (FIG. 40A). The amplitude median 161 will not pass through the midpoint 165 of a transverse (B-B') cross-section of the tampon where the groove is essentially directed away the centre of the tampon (FIG. 40A).

In another aspect, the invention relates to a method for producing a tampon, comprising the steps of:

providing a tampon blank of fibrous material having a longitudinal axis;

compressing in a press the tampon blank and forming longitudinal grooves at an outer circumferential surface of the tampon which groove is defined in a longitudinal direction by an outer path on the surface of the tampon and an inner path below the surface of the tampon whereby the path of the closed entrance to a groove on the circumferential surface of the tampon, (i.e. the outer longitudinal path 2, FIG. 30A), describes a straight line along the body of said tampon 1, while the longitudinal path of the closed groove below the surface of the tampon (i.e. an inner longitudinal path 5, FIG. 31A) is at least partly divergent from the outer longitudinal path 2 (or longitudinal groove axis 7).

withdrawing said pressed tampon out of the press in a longitudinal direction of the tampon body.

Thus present tampon may in particular characterized in that at least one tampon groove is defined by an outer longitudinal path on the surface of the tampon and an inner longitudinal path below the surface of the tampon whereby the outer longitudinal path 2 corresponds to a straight line, and the inner longitudinal path 5 is at least partly divergent from the longitudinal groove axis 7.

The divergence of the inner longitudinal path 5 may gradually increase towards the innermost point of the groove. In other words there may be an increase in the amplitude of the divergence (e.g. increase in the amplitude of a sinusoidal path) as the closed surface of the groove is viewed in planes towards the innermost point of the groove. This is shown in FIGS. 34A to 36B and elaborated below.

It can also be seen from FIGS. 34A to 36B that the shape of the groove can be defined using an x1y1z1 co-ordinate system wherein y1 corresponds to a value in an axis (y1-axis) along the longitudinal groove axis 7, z1 corresponds to a value in an axis (z1-axis 51) perpendicular to the y1-axis and which projects into the groove along the amplitude median 161, and wherein x1 corresponds to a value in an axis (x1-axis 52) which is perpendicular to said y1- and z1-axes.

When z1=0 (FIGS. 34A, 34B), the shape of the groove may be a straight line. In other words, the value of x1 is constant for any given value of y1 as reflected in the straight outer longitudinal path 2. When z1>0 (FIGS. 35A to 36B), the shape of the groove changes and diverges from the path of the longitudinal grove axis 7. This is clearly depicted in FIGS. 35A and 35B, where a slice removed from the tampon across a plane 53 defined by the x1 and y1 axes at depth z1 reveals the inner longitudinal path 5 of the groove. In FIGS. 35A and 35B, the depth z1 is approximately a fifth of the width W of the tampon (i.e. z1=0.2 W). Thus, when z1>0, the value of x1 along the y1-axis changes to provide a inner longitudinal path 5 that diverges from the longitudinal groove axis 7.

According to one embodiment of the invention, the path of a groove below the surface of the tampon is straight and inclined compared with path of the groove on the surface of the tampon (FIGS. 31A, 31B). This embodiment is also depicted in FIGS. 16A to 16C. At least one tampon groove may be defined by an outer longitudinal path 2 on the surface of the tampon and an inner longitudinal path 5 below the surface of the tampon whereby the outer longitudinal path 2 corresponds to a straight line, and the inner longitudinal path 5 corresponds to a straight line inclined to the longitudinal groove axis 7 for a groove.

In a preferred embodiment, the inner longitudinal path 5 of a groove of said tampon corresponds to a line showing the function $$x1 = y1z1a+b$$

wherein a is different from zero, b is a constant wherein y1 corresponds to a value in an axis (y1-axis) along the longitudinal groove axis 7, wherein z1 corresponds to a value in an axis (z1-axis 51) perpendicular to the y1-axis and which projects into the groove along the amplitude median 111, and wherein x1 corresponds to a value in an axis (x1-axis 52) which is perpendicular to said y1- and z1-axes.

According to one embodiment of the invention, the path of a groove below the surface of the tampon is at least partly curved compared with path of the groove on the surface of the tampon. Examples of curved line shapes include sinusoidal, wave-like, asymptotic. At least one tampon groove may be defined by an outer longitudinal path 2 on the surface of the tampon and an inner longitudinal path 5 below the surface of the tampon whereby the outer longitudinal path 2 corresponds to a straight line, and the inner longitudinal path 5 corresponds to a curved line. This embodiment is exemplified in FIGS. 32A to 33B, showing a tampon below the surface, whereby the inner longitudinal path 5 is curved. The path may have one or more points of inflection 6 through a longitudinal groove axis 7, which inflection point defines a convex part and a concave part with respect to the longitudinal groove axis 7. The terms "point of inflection", "convex part", "open convex part", "closed convex part", "concave part" have been described elsewhere.

FIG. 32A shows the instance where the inner longitudinal path 5 adopts a wave-like, sinusoidal curvature, and there are multiple points of inflection 6, 6'. FIG. 33A shows an inner longitudinal path 5 that is asymptotic having one point of inflection 6.

Figure 36B:
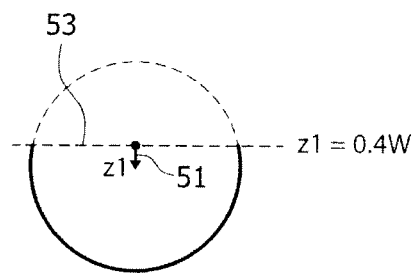

According to one aspect of the invention, the curvature increases as the value of z1 increases i.e. the depth of the groove increases. This is exemplified in FIGS. 34A to 36B. These figures which depict the inner longitudinal path 5 of the groove of the tampon across a plane 53 defined by the x1 and y1 axes, as the values of z1 increase. In FIG. 34B, the value of z1=0, giving a corresponding outer longitudinal path 2 (FIG. 34A) that is a straight line. In FIG. 35B, the value of z1 is approximately one fifth of the width W (z1=0.2 W) of the tampon, giving a giving a corresponding inner longitudinal path 5 (FIG. 35A) that is curved. In FIG. 36B, the value of z1 is approximately two fifths of the width W (z1=0.4 W) of the tampon, giving a giving a corresponding inner longitudinal path 5 (FIG. 35A) that is curved, even more so than when z1=0.2 W. Thus it is clearly seen from FIGS. 34A to 36B that the curvature of the inner longitudinal path 5 may increased as the depth of the groove increases.

In a preferred embodiment, the inner longitudinal path 5 of a groove of said tampon corresponds to a curved line showing the function $$y1 = a(x1/z1)^m$$

wherein m is an odd positive whole number which is different from 1, wherein a is different from zero, wherein y1 corresponds to a value in an axis (y1-axis) along the longitudinal groove axis 7, wherein z1 corresponds to a value in an axis (z1-axis 51) perpendicular to the y1-axis and which projects into the groove at the point of inflection 6, and wherein x1 corresponds to a value in an axis (x1-axis 52) which is perpendicular to said y1- and z1-axes.

The above-referred function is a power function wherein x1, y1 and z1 are the variables that are to be related, parameters a and m describe the relationship. The parameter a moves the values for $(x1/z1)^m$, up or down as an increase or decrease, respectively. The parameter m, determines the function's rates of growth or decay. Preferably the parameter m is a positive and odd whole number, different from zero and one and for instance 3, 5, 7, 9, etc. the parameter a is different from zero and may for instance be −6, −5, −4, −3, −2, −1, 1, 2, 3, 4, 5, 6, etc. The longitudinal grooves and/or ribs preferably extend over at least 25° to 80° of the tampons' circumference, and preferably over 30 to 45° of the tampons' circumference.

In a particularly preferred embodiment, the inner longitudinal path 5 of a groove corresponds to a curved line showing the function $y1=(x1/z1)^3$.

In alternative preferred embodiment, the inner longitudinal path 5 of a groove follows the path of a continuous hyperbolic function or to a continuous inverse hyperbolic. The term "continuous" as used herein refers to a curve or function, which extends without break or irregularity.

In a particularly preferred embodiment, the hyperbolic function corresponds to any of the following hyperbolic functions $y1=\sin h(x1)$ or $y=\tan h(x1)$ wherein y1 corresponds to a value in an axis along the inner longitudinal path 5, and wherein x1 corresponds to a value in an axis perpendicular thereto. The function $y1=\sin h(x1)$ corresponds to a hyperbolic sine of x1 (see FIG. 8A), and can also be written as $y1=\sin h(x1)=(e^{x1}-e^{-x1})/2$. The function $y1=\tan h(x1)$ corresponds to a hyperbolic tangent of x1 (see FIG. 8B), and can also be written as $y1=\sin h(x1)/\cos h(x1)$ whereby $\sin h(x1)$ is $(e^{x1}-e^{-x1})/2$ and $\cos h(x1)$ is $(ex^1+e^{-x1})/2$.

In a particularly preferred embodiment, the inverse hyperbolic function corresponds to the function $y1=\text{artan } h(x1)$, wherein y1 corresponds to a value in an axis along the inner longitudinal line 5, and wherein x1 corresponds to a value in an axis perpendicular to the inner longitudinal line 5. The function $y1=\text{artan } h(x1)$ corresponds to inverse hyperbolic tangent of x1 (see FIG. 8C).

The values for x1 and y1 in the above-indicated power or hyperbolic function may be as follows: x1 may be a value that is comprised between +½ W and −½ W and y1 may be a value that is comprised between +½ L and −½ L, z1 may be a value that is comprised between +½ W and −½ W.

According to one embodiment of the invention, the inner longitudinal path 5 of a groove below the surface of the tampon is curved compared with path of the groove on the surface of the tampon, and the inner longitudinal path 5 has only one point of inflection 6 (FIG. 33A). The point of inflection will correspond with the amplitude median 161, which inflection point 6 defines one convex part and one concave part with respect to the longitudinal groove axis 7.

In a preferred embodiment, said point of inflection is substantially located in the middle part of the tampon longitudinal body. Preferably point of inflection is located in a region covering the middle 50% of the tampon longitudinal body area. Even more preferred, this point of inflection is located about an imaginary line known as the longitudinal groove axis 7 (FIG. 33A). It is noted that it is of utmost importance in the present tampon configuration that only one point of inflection is provided in the path of the tampon grooves. Because there is only one point of inflection, the path of the grooves will undergo only one change in direction. As a consequence thereof, friction between the tampon grooves and the pressing apparatus can be considerably minimized.

In a preferred embodiment, the tampon is characterised in that the inner longitudinal path 5 corresponds to a continuous curved line, which is point symmetric in relation to said point of inflection.

In a particularly preferred embodiment, the tampon is characterised in that the inner longitudinal path 5 corresponds to a continuous curved line which does not show a point having a first derivative equal to zero. In other words, the curve describing path of inner longitudinal path 5 along the longitudinal groove axis 7 does not show a minimum and/or maximum.

The inner longitudinal path 5 corresponds to a continuous curved line, which preferably does not show any points wherein a first derivative is equal to zero. However, in an alternative embodiment, the inner longitudinal path 5 may correspond to a curved line showing one or two points which have a first derivative equal to zero. A first such point may be located in the top 25% of the tampon longitudinal body length, and for instance be located in the insertion end of the tampon. A second such point may be located in the bottom 25% of the tampon longitudinal body length, and for instance be located in the withdrawal end on the tampon. In an embodiment, a tampon is provided, wherein said curved line shows only one point which has a first derivative equal to zero, whereby a first point is located in the top 25% or the bottom 25% of the tampon longitudinal body length. In another embodiment, a tampon is provided tampon wherein said curved line shows maximally two points which has a first derivative equal to zero, whereby a first point is located in the top 25% and a second point is located in an the bottom 25% of the tampon longitudinal body length. In yet another embodiment, a tampon is provided wherein said point wherein the first derivative equal to zero is located at the top of the tampon, i.e. at −½ L, and/or at the bottom of the tampon, i.e. at +½ L.

The outer longitudinal path 2 may describe a straight line along the body of said tampon 1. According to one aspect of the invention (FIG. 37B), the outer longitudinal path 2 is parallel to the longitudinal groove axis 7 of the tampon, giving rise to tampons with a non-inclined groove appearance. In other words, the longitudinal groove axis 7 of a groove is parallel to the central axis (A-A') of the tampon.

According to another aspect of the invention, the outer longitudinal path 2 of a groove may be inclined (FIG. 38B), to the central axis (A-A') of the tampon, so producing tampons with a inclined groove appearance. In other words, the longitudinal groove axis 7 of a groove is inclined to the central axis (A-A') of the tampon.

According to one aspect of the invention, when the tampon is viewed end on (i.e. along the A-A' axis, or along arrow 33 in FIG. 37B), the distal 32 and proximal 31 end points of the outer longitudinal path 2 coincide; this arises in the case of a non-inclined surface groove, as shown in FIG. 37A.

According to another aspect of the invention, when the tampon is viewed end on (i.e. along the A-A' axis, or along arrow 34 in FIG. 38B), the distal 32 and proximal 31 end points of the outer longitudinal path 2 do not coincide; this arises in the case of an inclined surface groove, as shown in FIG. 38A. The distal and proximal end points of the line are offset. The angle of the offset, called beta1, when viewed along the A-A' axis, can be plus or minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43, 44, 45, 46, 47, 48, 49, 50, 55, 60, 65, 70, 75, 80, 85, 89, 90 deg, or a value in the range between any two of the aforementioned values, preferably 10 to 50 deg, more preferably 20 to 40, and most preferably 25 to 30 deg. It may be −10 to −50 deg, more preferably −20 to −40, and most preferably −25 to −30 deg. In the preferred range, the production process is improved in the compression and the ejection of the pressed product.

As shown in FIG. 38A, the angle of inclination can be defined according to the angle, alpha1, adopted between the outer longitudinal path 2 (or longitudinal groove axis 7) and a surface longitudinal line 4, the latter being a straight imaginary line drawn on the surface of the tampon, and which is parallel to the central axis (A-A') of the tampon. The surface longitudinal line 4 crosses the outer longitudinal path 2 in question, so creating the angle alpha1.

The value of alpha1 can be plus or minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43, 44, 45, 46, 47, 48, 49, 50, 55, 60, 65, 70, 75, 80, 85, 89, 90 deg, or a value in the range between any two of the aforementioned values, preferably 10 to 50 deg, more preferably 20 to 40, and most preferably 25 to 30 deg. It may be −10 to −50 deg, more preferably −20 to −40, and most preferably −25 to −30 deg. In the preferred range, the production process is improved in the compression and the ejection of the pressed product.

According to one aspect of the invention, the angle of inclination or the offset present in the outer longitudinal path 2 is reflected by the angle of inclination or the offset present in the inner longitudinal path 5. As already mentioned above, the longitudinal groove axis 7 for a groove, located below the surface of the tampon, may be parallel to the outer longitudinal path 2 described by the groove on the surface, and intersect the amplitude median 161. Thus, when the outer longitudinal path 2 is set an angle of inclination, the longitudinal groove axis 7 is similarly inclined. Thus, as surface layers of the tampon are peeled away, the longitudinal groove axis 7 remains parallel with the outer longitudinal path 2, but may intersect the amplitude median 161.

As further indicated below, the insertion end of the tampon may have undergone some deformation in order to have a dome shape or the like. It will be understood from the present invention that the above-indicated distal end may be integrated into the dome-like deformation of the insertion end. Likewise, as further indicated below, the withdrawal end of the tampon may also have undergone some deformation, e.g. in order to have a constricted shape. It will be understood from the present invention that also in such case the above-indicated proximal end may be integrated into the deformation of the withdrawal end.

According to one aspect of the invention the amplitude median 161 will pass through the midpoint 165 of a transverse (B-B') cross-section of the tampon where the groove is essentially directed towards the centre of the tampon (FIG. 40A). According to another aspect of the invention, the amplitude median 161 does not pass through the midpoint 165 of a transverse (B-B') cross-section of the tampon where the groove is essentially directed away the centre of the tampon (FIG. 40B).

According to one aspect of the invention, the amplitude median 161 of at least one groove follows the direction of the radius of the groove 162. According to one aspect of the invention, the amplitude median 161 of at least one groove, at least partially diverges from the radius of the groove 162. In detail, the tampon can be provided with the features as described below.

In one embodiment of the invention, an amplitude median 161 that diverges from the radius of a groove is illustrated in FIG. 41 which is a schematic illustration of a transverse (B-B') cross-section of a tampon at a point of inflection 6

(where a groove coincides with the amplitude median 161), according to the present invention. It can be seen from FIG. 41 that the amplitude median 161 of a groove does not coincide with the radius of the groove 162, but diverges therefrom.

The "radius of the groove" 162, as used herein, refers to straight radial line 162 that starts at the midpoint 165 of a transverse (B-B') cross-section of the tampon, and runs towards its circumference through the outermost (surface) point 164 of the closed groove.

The radius of a groove is illustrated in FIG. 41 as line 162.

The fictive circle 166 may be taken to be the circle centered at the midpoint 165 of the tampon in transverse (B-B') cross-section that touches the innermost point 163 of the groove in question.

According to one embodiment of the invention, the amplitude median 161 is positioned at a minimum angle (delta1) of 1, 2, 3, 4, 5, 6, 7, 8, 9, 10, 11, 12, 13, 14, 15, 16, 17, 18, 19 or 20 deg and a maximum angle of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 deg vis à vis the radius of the groove. According to one embodiment of the invention, when the amplitude median is positioned at a minimum angle of −1, −2, −3, −4, −5, −6, −7, −8, −9, −10, −11, −12, −13, −14, −15, −16, −17, −18, −19 or −20 deg and a maximum angle of −30, −31, −32, −33, −34, −35, −36, −37, −38, −39, −40, −41, −42, −43, −44, −45, −46, −47, −48, −49, −50, −51, −52, −53, −54, −55, −56, −57, −58, −59 or −60 deg vis à vis the radius of the groove 162.

According to another embodiment of the invention, when the amplitude median 161 is positioned essentially at an angle (delta1) between 1 deg and 60 deg (or −1 deg and −60 deg) vis à vis the radius of the groove 162, preferably at an angle between 1 deg and 30 deg (or −1 deg and −30 deg) and more preferably at an angle between 10 deg and 20 deg (or −10 deg and −20 deg).

The material of the tampon and the advantages the invention brings are already discussed above.

The tampons in the alternative embodiment of the invention can be easily and rapidly manufactured by a process using a press apparatus showing press jaws with penetrating segments or cogs, such as for instance described in the European patent application having application number 03447303.3. Herein, the tampon blank is pressed with such pressing apparatus. In order to form the ribs of the tampon, the method comprises compressing the tampon blank on its outer circumferential surface, forming longitudinal grooves and a fibre core. Preferably, the fibre core has a higher degree of compression from which less compressed longitudinal ribs extend outwards. The degree of compression in the ribs is less than in tampons of the prior art, allowing the absorption of more liquid.

The process essentially comprising the steps of:
inserting an essentially cylindrical blank of absorbing material in a press comprising press jaws including penetrating segments and pressing shoulders,
pressing essentially radially the tampon blank in the press jaws, so that the penetrating segments penetrate the cylindrical blank to form ribs defined by grooves and the pressing shoulders press on the circumferential surface of the ribs so-formed,
ejecting the so-formed pre-form,
subjecting the pre-form to further radial pressure on its total circumference, so forming a tampon.

The manufacturing method is easy, rapid and cost-effective, since material loss can be significantly reduced.

In a preferred embodiment the method for producing a tampon according to the invention comprises the steps of:

providing a tampon blank of fibrous material having a longitudinal axis;
compressing in a press the tampon blank and forming longitudinal grooves at an outer circumferential surface of the tampon which groove is defined in a longitudinal direction by an outer path on the surface of the tampon and an inner path below the surface of the tampon whereby
the path of the closed entrance to a groove on the circumferential surface of the tampon, (i.e. the outer longitudinal path 2, FIG. 30), describes a straight line along the body of said tampon 1, while the longitudinal path of the closed groove below the surface of the tampon (i.e. an inner longitudinal path 5, FIG. 31) is at least partly divergent from the outer longitudinal path 2 or longitudinal groove axis 7.
withdrawing said pressed tampon out of the press in a longitudinal direction of the tampon body.

The inner longitudinal path 5 may have only one point of inflection through the longitudinal groove axis 7, which inflection point defines one convex part and one concave part with respect of the line. The method may be adapted within the practices of the person skilled in the art to provide a tampon having one or more of the characteristics described above.

More in particular, in a preferred embodiment the method is as defined above, wherein said tampon blank is compressed in order to form longitudinal grooves, whereby the inner longitudinal path 5 of said groove of said tampon corresponds to a curved line showing the function $y=a(x/z)^m$ wherein m is an odd positive whole number which is different from 1,
wherein a is a constant that is different from zero,
wherein y corresponds to a value in an axis (y-axis) along the longitudinal groove axis 7,
wherein z corresponds to a value in an axis (z-axis) perpendicular to the y-axis and which projects into the groove at the amplitude median 161, and
wherein x corresponds to a value in an axis (x-axis) which is perpendicular to said y- and z-axes.

In another preferred embodiment, the method is as defined above, wherein said tampon blank is compressed in order to form inclined longitudinal grooves at an outer circumferential surface of the tampon which follow the path in the longitudinal direction of said tampon (i.e. along the inclined longitudinal line) of a curved line showing a hyperbolic function or an inverse hyperbolic function.

In detail, a preferably cylindrical tampon blank is introduced in the press apparatus described above.

The tampon blank is radially compressed by press jaws, such as those described above. If the penetrating segments and the pressing shoulders are fixed to separate press jaws, the tampon blank may be first pressed with the penetrating segments and subsequently with the pressing shoulders. Alternatively, the penetrating segments and the pressing shoulders may press the tampon blank simultaneously. The latter will obviously be the case when the penetrating segments and pressing shoulders are fixed to the same press jaws. In the press, the tampon blank is preferably compressed in a single pressing operation by the penetrating segments and pressing shoulders simultaneously.

The penetrating segments will preferably press the tampon blank on strips of the circumferential surface that are narrower than the strips of the circumferential surface pressed by the pressing shoulders. Preferably also, the strips pressed by the penetrating segments have an equal length and width and the strips pressed by the pressing shoulders also have an equal length and width. In this way, ribs are formed, defined by longitudinal grooves on a solid fibre core. The pressing shoulders will press on the circumference of the so formed ribs in order to obtain an essentially cylindrical form with a smaller diameter. The memory effect of the tampon blank maintains the shape of the compressed tampon form.

The tampon blank, having been pressed by the penetrating segments and pressing shoulders, forms a pre-form, which is ejected from the press. This pre-form is simultaneously subjected to final shaping downstream. This final shaping includes a radial pressure being exerted on the total circumference of the pre-form. This radial pressure has the effect that the adjacent longitudinal ribs are pressed against one another, so that the grooves are substantially closed and the circumferential surface of the tampon is substantially smooth and soft.

The tampon blank is, depending on the properties of the fibrous material used, in particular in the event of use of highly expansive fibers of irregular cross section with a strong memory effect, pressed at the temperature of the press jaws to the final shape of the tampon, in order to achieve the desired dimensional stability of the fibrous material by eliminating the memory effect of the fibers, which immediately becomes effective again on contact with bodily fluid and thus increases the expansion and absorption speed of the tampon with the least possible use of fibrous material.

Further Embodiments

One embodiment of the invention is a tampon for feminine hygiene having a longitudinal body showing in compressed condition a length L and a width W, whereby said tampon essentially consists of compressed absorbent fibrous material and has an outer circumferential surface which is provided with longitudinal grooves that are separated from each other by longitudinal ribs, wherein at least one tampon groove is defined by an outer longitudinal path on the surface of the tampon and an inner longitudinal path below the surface of the tampon whereby the outer longitudinal path corresponds to a straight line, and the inner longitudinal path is at least partly divergent from the longitudinal groove axis.

Another embodiment of the invention is a tampon as described above, wherein divergence of the inner path increases gradually from the surface of the tampon towards an innermost point of the groove.

Another embodiment of the invention is a tampon as described above, wherein the inner longitudinal path corresponds to a straight line inclined to the outer longitudinal path or longitudinal groove axis for a groove.

Another embodiment of the invention is a tampon as described above, wherein the inner longitudinal path corresponds to a line showing the function $$x1 = y1z1a + b$$

wherein a is different from zero, b is a constant
wherein y1 corresponds to a value in an axis (y1-axis) along the longitudinal groove axis 7,
wherein z1 corresponds to a value in an axis (z1-axis) perpendicular to the y1-axis and which projects into the groove along the amplitude median, and
wherein x1 corresponds to a value in an axis (x1-axis) which is perpendicular to said y1- and z1-axes.

Another embodiment of the invention is a tampon as described above, wherein the inner longitudinal path corresponds to a curved line.

Another embodiment of the invention is a tampon as described above, wherein the inner longitudinal path has one or more points of inflection through a longitudinal groove axis, which inflection point defines a convex part and a concave part with respect to the longitudinal groove axis.

Another embodiment of the invention is a tampon as described above, wherein the inner longitudinal path adopts a wave-like line or an asymptotic line.

Another embodiment of the invention is a tampon as described above, wherein said inner longitudinal path corresponds to a curved line showing the function $$Y1 = a(x1/z1)^m$$

wherein m is an odd positive whole number which is different from 1,
wherein a is different from zero,
wherein y1 corresponds to a value in an axis (y1-axis) along the longitudinal groove axis (7),
wherein z1 corresponds to a value in an axis (z1-axis) perpendicular to the y1-axis and which projects into the groove along the amplitude median (161), and
wherein x1 corresponds to a value in an axis (x1-axis) which is perpendicular to said y1- and z1-axes.

Another embodiment of the invention is a tampon as described above, wherein said inner path corresponds to a curved line showing the function $y1 = (1x/z1)^3$.

Another embodiment of the invention is a tampon as described above, wherein said inner path corresponds to a hyperbolic function, or an inverse hyperbolic function.

Another embodiment of the invention is a tampon as described above, wherein said function corresponds to any of the following functions, at a depth z1:

$$y1 = \sin h(x1), \text{ or}$$

$$y1 = \tan h(x1), \text{ or}$$

$$y1 = \operatorname{artan} h(x1)$$

wherein y1 corresponds to a value in an axis, y1-axis, along a longitudinal groove axis 7,
wherein x1 corresponds to a value in an axis, x1-axis, which axis is perpendicular to said x1- and z1-axes.

Another embodiment of the invention is a tampon as described above, wherein the value of x1 is comprised between $-\frac{1}{2}$ W and $+\frac{1}{2}$ W.

Another embodiment of the invention is a tampon as described above, wherein the value of y1 is comprised between $-\frac{1}{2}$ L and $+\frac{1}{2}$ L.

Another embodiment of the invention is a tampon as described above, wherein the value of z1 is comprised between 0.01 W and 0.45 W.

Another embodiment of the invention is a tampon as described above, wherein the outer longitudinal path or longitudinal groove axis is parallel to the central axis (A-A') of the tampon.

Another embodiment of the invention is a tampon as described above, wherein the outer longitudinal path or longitudinal groove axis is inclined to the central axis (A-A') of the tampon.

Another embodiment of the invention is a tampon as described above, wherein distal and proximal end points of the outer longitudinal path are offset by an angle, beta, of between 10 to 50 deg, or −10 to −50 deg.

Another embodiment of the invention is a tampon as described above, wherein an angle of inclination, alpha, adopted between the outer longitudinal path and a surface longitudinal line is between 10 to 50 deg or −10 to −50 deg, the surface longitudinal line (4) being a straight imaginary line drawn on the surface of the tampon, and which is parallel to the central axis (A-A') of the tampon.

Another embodiment of the invention is a tampon as described above, wherein an angle of inclination, alpha, adopted between a longitudinal groove axis and a surface longitudinal line is between 10 to 50 deg or −10 to −50 deg, the surface longitudinal line being a straight imaginary line drawn on the surface of the tampon, and which is parallel to the central axis (A-A') of the tampon.

Another embodiment of the invention is a tampon as described above, wherein an amplitude median of a groove of a groove, follows the direction of the radius of the groove,
  the amplitude median (161—FIG. 39) of a groove, being a straight line drawn on a transverse (B-B') cross-section (102) of a tampon, from the outermost point (101) of the groove, to the middle point (103) of an arc centred on said point (101), which arc is bound by sides (105, 105') that are determined by the maximum and minimum (106, 106') divergence of the whole groove viewed along the longitudinal axes (A-A'), and
  the radius of the groove (162) being the straight radial line (162) that starts at the midpoint (115) of a transverse (B-B') cross-section of the tampon, and runs towards its circumference through the outermost (surface) point (114) of the closed groove.

Another embodiment of the invention is a tampon as described above, wherein an amplitude median (161) of a groove, is divergent from the radius of the groove (162),
  the amplitude median (161—FIG. 40) of a groove, being a straight line drawn on a transverse (B-B') cross-section (102) of a tampon, from the outermost point (101) of the groove, to the middle point (103) of an arc centred on said point (101), which arc is bound by sides (105, 105') that are determined by the maximum and minimum (106, 106') divergence of the whole groove viewed along the longitudinal axes (A-A'), and
  the radius of the groove (162) being the straight radial line (162) that starts at the midpoint (115) of a transverse (B-B') cross-section of the tampon, and runs towards its circumference through the outermost (surface) point (114) of the closed groove.

Another embodiment of the invention is a tampon as described above, in which said amplitude median (161) is essentially at an angle between 1° and 60° or −1° and −60° vis à vis the radius (162) of that groove.

Another embodiment of the invention is a tampon as described above, in which said amplitude median (161) is essentially at an angle between 1° and 30° or −1° and −30° vis à vis the radius (162) of that groove.

Another embodiment of the invention is a tampon as described above, in which said amplitude median (161) is essentially at an angle between 10° and 20° or −10° and −20° vis à vis the radius (162) of that groove.

Another embodiment of the invention is a tampon as described above, in which the tampon is provided with a finger recess.

Another embodiment of the invention is a tampon as described above, wherein said finger recess is provided at the withdrawal end.

Another embodiment of the invention is a tampon as described above, wherein the tampon is provided with a dome shaped insertion end.

Another embodiment of the invention is a tampon as described above, in which the tampon is mushroom shaped.

Another embodiment of the invention is a tampon as described above, wherein the tampon is provided with a constricted withdrawal end.

Another embodiment of the invention is a tampon as described above, in which the tampon is provided with a conical shaped withdrawal end.

Another embodiment of the invention is a tampon as described above, having a withdrawal cord which extends from said withdrawal end.

Another embodiment of the invention is a tampon as described above, in which the ribs touch each other so as to form an essentially smooth cylindrical surface.

Another embodiment of the invention is a tampon as described above, provided with one or more markings on the surface.

Another embodiment of the invention is a tampon as described above, wherein said marking one or more of alpha numerals, graphic illustrations, patterns, solid colours and photographic illustrations.

Another embodiment of the invention is a tampon as described above, wherein said marking is information.

Another embodiment of the invention is a tampon as described above, provided with one or more chemical indicators that is capable of changing colour.

Another embodiment of the invention is a tampon as described above, wherein a chemical indicator is capable of colour change according to the presence of a disease or condition detectable by a colour change reaction.

Another embodiment of the invention is a tampon as described above, wherein a condition is anaemia and a chemical indicator detects iron or haemoglobin.

Another embodiment of the invention is a tampon as described above, wherein a condition is diabetes and a chemical indicator detects glucose.

Another embodiment of the invention is a tampon as described above, wherein a condition is a sexually transmitted disease and a chemical indicator detects antigens towards said sexually transmitted disease.

Another embodiment of the invention is a tampon as described above, wherein the tampon has a fibre core of highly compressed fibrous material and an outer circumferential surface which is provided with longitudinal ribs that extend radially outwards and that are defined by said longitudinal grooves.

Another embodiment of the invention is a tampon as described above, wherein said longitudinal ribs are at least partially relatively uncompressed compared with the fibre core.

Another embodiment of the invention is a tampon as described above, provided within an applicator.

Another embodiment of the invention is a method for producing a tampon as described above, comprising the steps of:
  providing a tampon blank of fibrous material having a longitudinal axis;
  compressing in a press the tampon blank and forming longitudinal grooves at an outer circumferential surface of the tampon which groove is defined by an outer path on the surface of the tampon and an inner path below the surface of the tampon whereby
  at least one tampon groove is defined an outer longitudinal path on the surface of the tampon and an inner longitudinal path below the surface of the tampon whereby the inner longitudinal path is at least partly divergent from the outer longitudinal path or longitudinal groove axis.
  withdrawing said pressed tampon out of the press in a longitudinal direction of the tampon body.

Another embodiment of the invention is a method as described above, wherein the divergence of the inner path increases gradually from the surface of the tampon towards the innermost point of the groove.

Another embodiment of the invention is a method as described above, wherein said inner path is as defined above.

Another embodiment of the invention is a press suitable for manufacturing of a tampon as defined above by pressing absorbing fibrous material essentially radially, comprising press jaws including penetrating segments for pressing the absorbing material essentially radially and pressing shoulders.

Another embodiment of the invention is a press as described above, wherein said the radial pressing is towards longitudinal central axis of the tampon or divergent therefrom.

It is apparent that there has been provided in accordance with the invention, a tampon that fully satisfies the objects, aims, and advantages set forth above. While the invention has been described in conjunction with specific embodiments thereof, it is evident that many alternatives, modifications, and/or variations will be apparent to those skilled in the art in the light of the foregoing description. Accordingly, it is intended to embrace all such alternatives, modifications, and variations.

What is claimed is:

1. A tampon having an insertion end, a withdrawal end and a tampon body in between whereby said tampon body essentially consists of liquid absorbing material and has an outer circumferential surface which is provided with longitudinal grooves that are separated from each other by longitudinal ribs, wherein at least one tampon groove is defined an outer longitudinal path on the surface of the tampon that diverges from the longitudinal path of the groove below the surface of the tampon, wherein the groove of a tampon is defined by a plurality of inner longitudinal paths below the surface of the tampon, the path of each inner longitudinal path being across an x-y plane at a depth z, whereby the inner longitudinal paths of at least two x-y planes are divergent, wherein the divergent paths give rise to a path length in an x-y plane that decreases as the x-y plane rises towards the surface of the tampon or wherein the divergent paths give rise to a path length in an x-y plane that increases as the x-y plane rises towards the surface of the tampon.

2. A tampon according to claim 1, wherein the tampon groove is defined by said plurality of inner longitudinal paths below the surface of the tampon, each tracing the longitudinal path of a groove at a given depth, and an outer longitudinal path on the surface of the tampon, and whereby the outer longitudinal path at least partially diverges from at least one inner longitudinal path.

3. Tampon according to claim 2 wherein at least one of the inner longitudinal paths of a groove is undulated.

4. Tampon according to claim 3, wherein at least two of said inner longitudinal paths are undulated, and the amplitudes of said undulations decrease in the direction from the core to the surface of the tampon.

5. Tampon according to claim 3, wherein at least two of said inner longitudinal paths are undulated, and the amplitudes of said undulations increase in the direction from the core to the surface of the tampon.

6. Tampon according to claim 3 wherein the frequency of said undulations decease in the direction from the core to the surface of the tampon.

7. Tampon according to claim 3 wherein the frequency of said undulations increase in the direction from the core to the surface of the tampon.

\* \* \* \* \*